United States Patent
Kiick et al.

(10) Patent No.: US 12,171,809 B2
(45) Date of Patent: Dec. 24, 2024

(54) COLLAGEN-MIMETIC PEPTIDE MEDIATED DELIVERY OF NUCLEIC ACID CARRIERS FOR EFFICIENT DELIVERY FROM COLLAGEN

(71) Applicant: University of Delaware, Newark, DE (US)

(72) Inventors: Kristi Kiick, Rising Sun, MD (US); Millicent Sullivan, Wilmington, DE (US); Morgan Urello, Gaithersburg, MD (US)

(73) Assignee: UNIVERSITY OF DELAWARE, Newark, DE (US)

( * ) Notice: Subject to any disclaimer, the term of this patent is extended or adjusted under 35 U.S.C. 154(b) by 1445 days.

(21) Appl. No.: 16/316,378

(22) PCT Filed: Jul. 18, 2017

(86) PCT No.: PCT/US2017/042645
§ 371 (c)(1),
(2) Date: Jan. 9, 2019

(87) PCT Pub. No.: WO2018/017598
PCT Pub. Date: Jan. 25, 2018

(65) Prior Publication Data
US 2020/0179490 A1 Jun. 11, 2020

Related U.S. Application Data

(60) Provisional application No. 62/363,415, filed on Jul. 18, 2016.

(51) Int. Cl.
| | |
|---|---|
| A61K 48/00 | (2006.01) |
| A61K 38/18 | (2006.01) |
| A61K 38/19 | (2006.01) |
| A61K 38/20 | (2006.01) |
| A61K 38/21 | (2006.01) |
| A61K 38/39 | (2006.01) |
| A61K 38/48 | (2006.01) |
| A61K 47/64 | (2017.01) |
| C12N 9/64 | (2006.01) |
| C12N 15/113 | (2010.01) |

(52) U.S. Cl.
CPC ............ *A61K 38/39* (2013.01); *A61K 38/18* (2013.01); *A61K 38/191* (2013.01); *A61K 38/20* (2013.01); *A61K 38/21* (2013.01); *A61K 38/4886* (2013.01); *A61K 47/6455* (2017.08); *A61K 48/00* (2013.01); *C12N 9/6491* (2013.01); *C12Y 304/24007* (2013.01); *A61K 48/0008* (2013.01); *A61K 48/0025* (2013.01); *A61K 48/0041* (2013.01); *A61K 48/005* (2013.01); *A61K 48/0075* (2013.01); *C12N 15/113* (2013.01); *C12N 2310/14* (2013.01)

(58) Field of Classification Search
CPC .... A61K 38/39; A61K 47/6455; A61K 48/00; A61K 48/0008; A61K 48/0025; A61K 48/0041; A61K 48/005; A61K 48/0075; C12N 15/113; C12N 2310/14
See application file for complete search history.

(56) References Cited

U.S. PATENT DOCUMENTS

| | | | |
|---|---|---|---|
| 5,962,427 A * | 10/1999 | Goldstein | A61P 17/06 435/325 |
| 2002/0010134 A1 | 1/2002 | Bhatnagar et al. | |
| 2009/0240001 A1 | 9/2009 | Regner | |
| 2013/0164220 A1 | 6/2013 | Yu et al. | |
| 2014/0238153 A1 | 8/2014 | Wood et al. | |
| 2015/0111308 A1 | 4/2015 | Yu et al. | |
| 2016/0008399 A1 | 1/2016 | Stephan | |
| 2016/0025669 A1 | 1/2016 | Sun et al. | |

OTHER PUBLICATIONS

International Search Report for PCT Application No. PCT/US2017/042645, mailed Nov. 21, 2017 by Lee W. Young.
Urello et al., J. Mater. Chem. B, 2:8174-85 (2014).
Wang et al., J. Am. Chem. Soc., 127:4130-1 (2005).
International Preliminary Report on Patentability for International Application No. PCT/US2017/042645, dated Jan. 22, 2019, 11 pages.

* cited by examiner

*Primary Examiner* — J. E. Angell
(74) *Attorney, Agent, or Firm* — Buchanan Ingersoll & Rooney PC

(57) ABSTRACT

The present invention provides a composition for delivering a polynucleotide into cells via a polyplex. The polyplex comprises the polynucleotide and a polymer. The composition comprises the polyplex, a collagen-mimetic peptide (CMP) and collagen fragments. The CMP is bound to the polyplex and the collagen fragments. Also provided are the uses of the composition in methods of delivering a polynucleotide into cells as well as methods of improving wound healing in a subject, enhancing cell proliferation in a subject, enhancing production of extracellular matrix by cells in a subject and/or enhancing cell migration by cells in a subject.

17 Claims, 15 Drawing Sheets
Specification includes a Sequence Listing.

a)

b)

c)

d)

a)

b)

COLLAGEN-MIMETIC PEPTIDE MEDIATED DELIVERY OF NUCLEIC ACID CARRIERS FOR EFFICIENT DELIVERY FROM COLLAGEN

CROSS-REFERENCE TO RELATED APPLICATION

This application is a U.S. national phase of International Application No. PCT/US2017/042645, filed Jul. 18, 2017 claiming the benefit of U.S. Provisional Application No. 62/363,415 filed Jul. 18, 2016, the contents of which are incorporated herein by reference In their entireties for all purposes.

REFERENCE TO U.S. GOVERNMENT SUPPORT

This invention was made with government support under 1159466 awarded by the National Science Foundation. The United States has certain rights in the invention.

FIELD OF THE INVENTION

The invention relates generally to collagen-mimetic peptide (CMP) mediated delivery of nucleic acid carriers.

BACKGROUND OF THE INVENTION

Collagen-mimetic peptides (CMPs), consisting of glycine-proline-hydroxyproline/proline tripeptide motifs, have been widely demonstrated to have a unique affinity for natural collagen. The targeted binding is attributed to a triple helix hybridization process between the CMP and natural collagen and has already been utilized to robustly modify collagen, both in vivo and in vitro, with a myriad of non-nucleic acid cargoes such as growth factors (GFs). A CMP-based method for tunable, cell-mediated gene delivery from collagen scaffolds in in vitro systems has recently been reported. (Urello et al., J. Mater. Chem. B, 2014, 2, 8174-85). However, successful in vivo delivery and expression of genes via collagen-CMP hybridization with biological effects have not been reported. Improved gene carriers for in vivo applications are critical because in vitro gene delivery systems typically perform very poorly in vivo due to off-target effects and limited stability. Off-target delivery can cause immune responses and may induce gene expression in undesirable locations. Meanwhile, gene carriers with limited stability may either aggregate or disassemble, leading to a lack of the desired gene activity. Thus, there remains a need for a suitable in vivo CMP-mediated gene delivery method with desirable biological effects.

SUMMARY OF THE INVENTION

The present invention relates to collagen-mimetic peptide (CMP) mediated delivery of nucleic acid carriers and their uses and preparation.

A method of delivering a polyplex into cells is provided. The cells are in a subject. The polyplex comprises at least one polymer and at least one polynucleotide. The method comprises administering an effective amount of a composition to the cells. The composition comprises at least one collagen-mimetic peptide (CMP), the polyplex and collagen or fragments thereof. The at least one CMP is bound to the polyplex. The at least one CMP is bound to the collagen or fragments thereof.

According to the delivery method, the polynucleotide may be DNA. The polynucleotide may be RNA.

According to the delivery method, the at least one CMP may be bound to the polyplex via a covalent linkage. The at least one CMP may be bound to the polyplex via a noncovalent linkage.

When the at least one polynucleotide encodes at least one protein, the delivery method may further comprise expressing the at least one protein in the cells.

When the cells express at least one protein and the at least one polynucleotide encodes at least one silencing RNA capable of suppressing expression of the at least one protein, the delivery method may further comprise suppressing the expression of the at least one protein in the cells.

According to the delivery method, the cells may be at a wound in the subject.

The delivery method may further comprise enhancing proliferation of the cells.

The delivery method may further comprise enhancing production of extracellular matrix by the cells.

The delivery method may further comprise enhancing migration of the cells.

A method of improving wound healing in a subject is provided. The method comprises administering an effective amount of a composition to cells at a wound in the subject. The composition comprises at least one collagen-mimetic peptide (CMP), a polyplex and collagen or fragments thereof. The polyplex comprises at least one polymer and at least one polynucleotide. The at least one CMP is bound to the polyplex. The at least one CMP is bound to the collagen or fragments thereof. As a result, the wound healing is improved.

When the at least one polynucleotide encodes at least one protein, the method of improving wound healing may further comprise expressing the at least one protein in the cells.

When the cells express at least one protein and the at least one polynucleotide encodes at least one silencing RNA capable of suppressing expression of the at least one protein, the method of improving wound healing may further comprise suppressing the expression of the at least one protein in the cells.

A method of enhancing proliferation of cells in a subject is provided. The method comprises administering an effective amount of a composition to the cells. The composition comprises at least one collagen-mimetic peptide (CMP), a polyplex and collagen or fragments thereof. The polyplex comprises at least one polymer and at least one polynucleotide. The at least one CMP is bound to the polyplex. The at least one CMP is bound to the collagen or fragments thereof. As a result, proliferation of the cells is enhanced. The cells may be at a wound in the subject.

When the at least one polynucleotide encodes at least one protein, the method of enhancing cell proliferation may further comprise expressing the at least one protein in the cells. The at least one protein may comprise two or more proteins. The at least one protein may comprise at least one growth factor. The at least one growth factor may comprise two or more growth factors. Each of the at least one growth factors may be selected from the group consisting of epidermal growth factor (EGF), fibroblast growth factor (FGF), hepatocyte growth factor (HGF), insulin-like growth factor (IGF), keratinocyte growth factor (KGF), platelet-derived growth factor (PDGF), transforming growth factor (TGF), transforming growth factor-β (TGF-β), transforming growth factor-α (TGF-α) and vascular endothelial growth factor (VEGF). The at least one growth factor may comprise platelet-derived growth factor-BB (PDGF-BB).

When the cells express at least one protein and the at least one polynucleotide encodes at least one silencing RNA capable of suppressing expression of the at least one protein, the method of enhancing cell proliferation may further comprise suppressing the expression of the at least one protein in the cells. The at least one protein may comprise two or more proteins. The at least one protein may comprise at least one inflammatory cytokine. The at least one inflammatory cytokine may be selected from the group consisting of the interleukin family of proteins, the interferon family of proteins, and tumor necrosis factor-α (TNF-α).

A method of enhancing production of extracellular matrix (ECM) by cells in a subject is provided. The method comprises administering an effective amount of a composition to the cells. The composition comprises at least one collagen-mimetic peptide (CMP), a polyplex and collagen or fragments thereof. The polyplex comprises at least one polymer and at least one polynucleotide. The at least one CMP is bound to the polyplex. The at least one CMP is bound to the collagen or fragments thereof. As a result, production of extracellular matrix by the cells is enhanced. The cells may be at a wound in the subject.

When the at least one polynucleotide encodes at least one protein, the method of enhancing ECM production may further comprise expressing the at least one protein in the cells. The at least one protein may comprise two or more proteins. The at least one protein may comprise at least one growth factor. The at least one growth factor may comprise two or more growth factors. Each of the at least one growth factor may be selected from the group consisting of epidermal growth factor (EGF), fibroblast growth factor (FGF), hepatocyte growth factor (HGF), insulin-like growth factor (IGF), keratinocyte growth factor (KGF), platelet-derived growth factor (PDGF), transforming growth factor (TGF), transforming growth factor-β (TGF-β), transforming growth factor-α (TGF-α) and vascular endothelial growth factor (VEGF). The at least one growth factor may comprise platelet-derived growth factor-BB (PDGF-BB).

When the cells express at least one protein and the at least one polynucleotide encodes at least one silencing RNA capable of suppressing expression of the at least one protein, the method of enhancing ECM production may further comprise suppressing the expression of the at least one protein in the cells. The at least one protein may comprise two or more proteins. The at least one protein may comprise at least one inflammatory cytokine. The at least one inflammatory cytokine may be selected from the group consisting of the interleukin family of proteins, the interferon family of proteins, and tumor necrosis factor-α (TNF-α).

A method of enhancing migration of cells in a subject is provided. The method comprises administering an effective amount of a composition to the cells, wherein the composition comprises at least one collagen-mimetic peptide (CMP), a polyplex and collagen or fragments thereof. The polyplex comprises at least one polymer and at least one polynucleotide. The at least one CMP is bound to the polyplex. The at least one CMP is bound to the collagen or fragments thereof. As a result, migration by the cells is enhanced. The cells may be at a wound in the subject.

When the at least one polynucleotide encodes at least one protein, the method of enhancing cell migration may further comprise expressing the at least one protein in the cells. The at least one protein may comprise two or more proteins. The at least one protein may comprise at least one growth factor. The at least one growth factor may comprise two or more growth factors. Each of the at least one growth factor may be selected from the group consisting of epidermal growth factor (EGF), fibroblast growth factor (FGF), hepatocyte growth factor (HGF), insulin-like growth factor (IGF), keratinocyte growth factor (KGF), platelet-derived growth factor (PDGF), transforming growth factor (TGF), transforming growth factor-β (TGF-β), transforming growth factor-α (TGF-α) and vascular endothelial growth factor (VEGF). The at least one growth factor may comprise platelet-derived growth factor-BB (PDGF-BB).

When the cells express at least one protein and the at least one polynucleotide encodes at least one silencing RNA capable of suppressing expression of the at least one protein, the method of enhancing cell migration may further comprise suppressing the expression of the at least one protein in the cells. The at least one protein may comprise two or more proteins. The at least one protein may comprise at least one inflammatory cytokine. The at least one inflammatory cytokine may be selected from the group consisting of the interleukin family of proteins, the interferon family of proteins, and tumor necrosis factor-α (TNF-α).

According to any one of the methods of the present invention, the composition may be in the form of a gel, film, patch, or sponge. The composition may further comprise an extracellular matrix (ECM) component selected from the group consisting of fibrin, fibronectin, laminins, ECM proteoglycans, ECM glycosaminoglycans and combinations thereof. The composition may further comprise a matrix metalloproteinase (MMP). The MMP may be collagenase.

According to any one of the methods of the present invention, each of the at least one CMP may be (GPP)$_3$GPRGEKGERGPR(GPP)$_3$GPCCG (SEQ ID NO: 3) or (GPO)$_4$GEKGER(GPO)$_4$GGCG (SEQ ID NO: 4). O is hydroxyproline.

According to any one of the methods of the present invention, the at least one polymer may comprise polyethylenimine (PEI).

According to any one of the methods of the present invention, the collagen or fragments thereof may be selected from the group consisting of Type I collagen, Type II collagen, Type III collagen, Type IV collagen, Type V collagen, and combinations thereof. The collagen or fragments thereof may be networked. The collagen or fragments thereof may be insoluble.

A composition for delivering a polyplex into cells is provided. The polyplex comprises at least one polymer and at least one polynucleotide. The composition comprises at least one collagen-mimetic peptide (CMP), the polyplex and collagen fragments. The at least one CMP is bound to the polyplex. The at least one CMP is bound to the collagen fragments. The cells may be in a subject.

The polynucleotide in the composition may be DNA. The polynucleotide in the composition may be RNA.

The at least one CMP in the composition may be bound to the polyplex via a covalent linkage. The at least one CMP may be bound to the polyplex via a noncovalent linkage.

The at least one polynucleotide in the composition may encode at least one protein. The at least one protein may comprise two or more proteins. The at least one protein may comprise at least one growth factor. The at least one growth factor may comprise two or more growth factors. Each of the at least one growth factor may be selected from the group consisting of epidermal growth factor (EGF), fibroblast growth factor (FGF), hepatocyte growth factor (HGF), insulin-like growth factor (IGF), keratinocyte growth factor (KGF), platelet-derived growth factor (PDGF), transforming growth factor (TGF), transforming growth factor-β (TGF-β), transforming growth factor-α (TGF-α) and vascular endothelial growth factor (VEGF). The at least one growth factor may comprise platelet-derived growth factor-BB (PDGF-BB).

When the cells express at least one protein, the at least one polynucleotide in the composition may encode at least one silencing RNA capable of suppressing expression of the at least one protein. The at least one protein may comprise at least one inflammatory cytokine. The at least one inflammatory cytokine may be selected from the group consisting of the interleukin family of proteins, the interferon family of proteins, and tumor necrosis factor-α (TNF-α).

The composition may be in the form of a gel, film, patch or sponge.

The composition may further comprise an extracellular matrix (ECM) component selected from the group consisting of fibrin, fibronectin, laminins, ECM proteoglycans, ECM glycosaminoglycans and combinations thereof.

The composition may further comprise a matrix metalloproteinase (MMP). The MMP may be collagenase.

Each of the at least one CMP in the composition may be (GPP)$_3$GPRGEKGERGPR(GPP)$_3$GPCCG (SEQ ID NO: 3) or (GPO)$_4$GEKGER(GPO)$_4$GGCG (SEQ ID NO: 4).

The at least one polymer in the composition may comprise polyethylenimine (PEI).

The collagen fragments in the composition may be fragments of collagen selected from the group consisting of Type I collagen, Type II collagen, Type III collagen, Type IV collagen, Type V collagen, and combinations thereof. The collagen fragments may be insoluble. The collagen fragments may be networked.

* denotes a statistically-significant difference (p<0.05) relative to unmodified polyplex samples.

Figure 11:
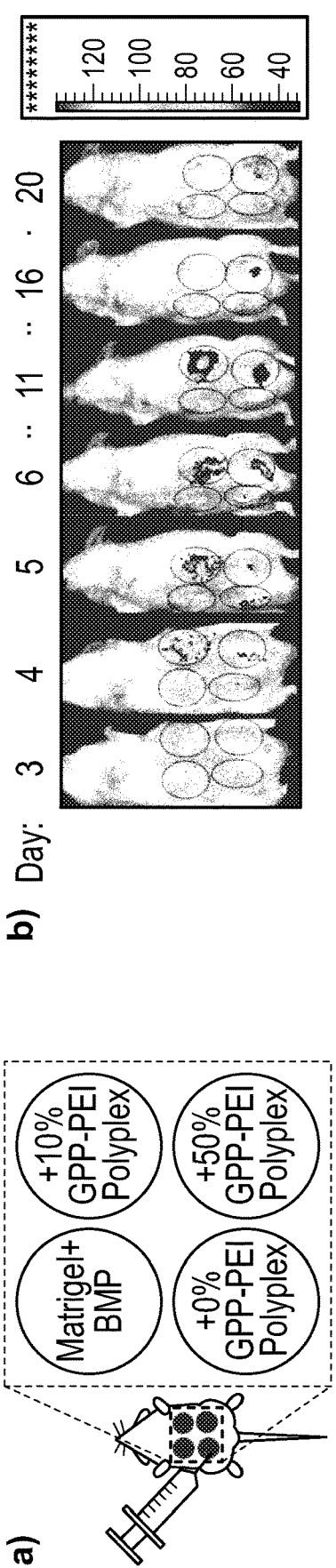
Figure 11:
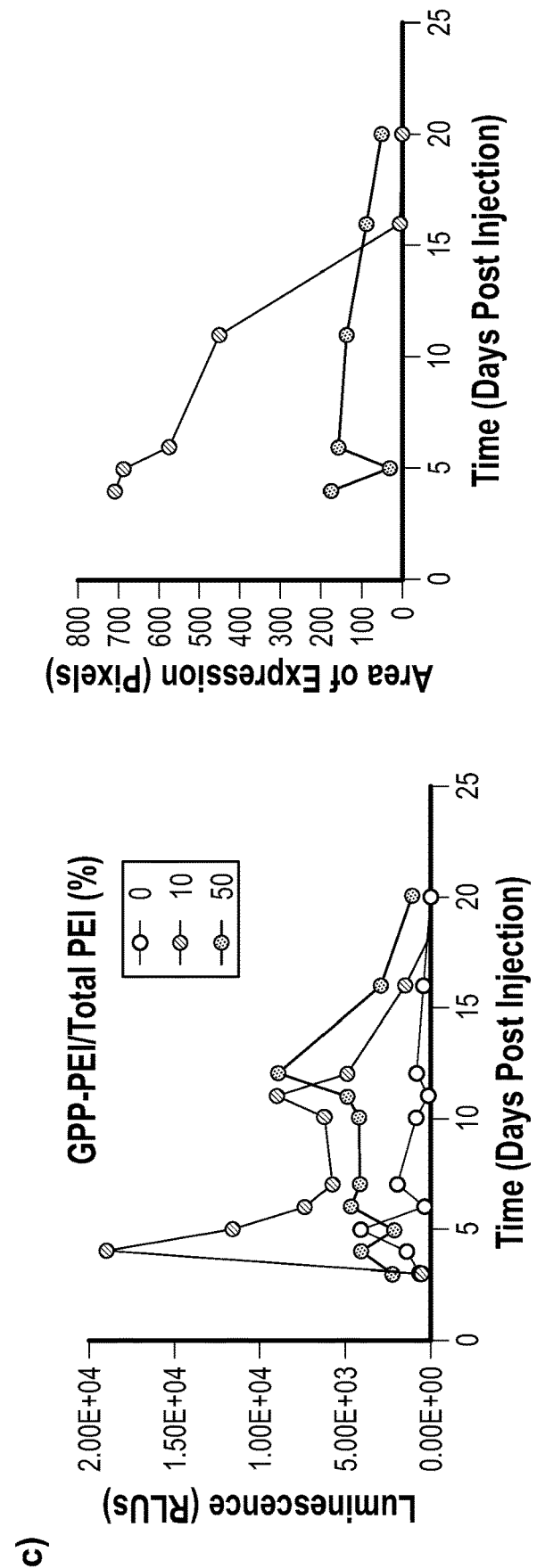
Figure 11:
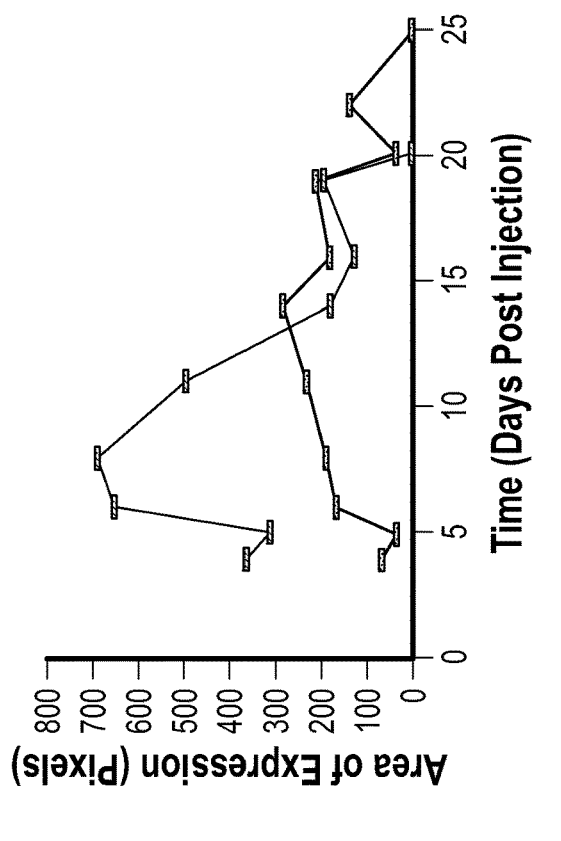

FIG. 11 shows in vivo application of CMP-modified polyplex. a) Schematic indicating the location and contents of each subcutaneous pellet on the abdomens of CD-1 mice. Each solution contained MATRIGEL, BMP-2, and polyplex where indicated, and the solutions formed visible pellets immediately after injection. DNA encoded for a membrane bound form of Metridia Luciferase to permit in vivo imaging. b) In vivo images of a representative mouse at various time points post injection, taken using an IVIS (Exposure: 5 s, Binning: Large, f/stop: 1) indicating luminescence over a maximum period of 20 d. c) Quantification of transgene expression and the area over which expression was identified in a representative mouse. d) The median value of transgene expression and the area over which expression is detected within replicates. This study was replicated in four mice (FIG. 13).

Figure 12:
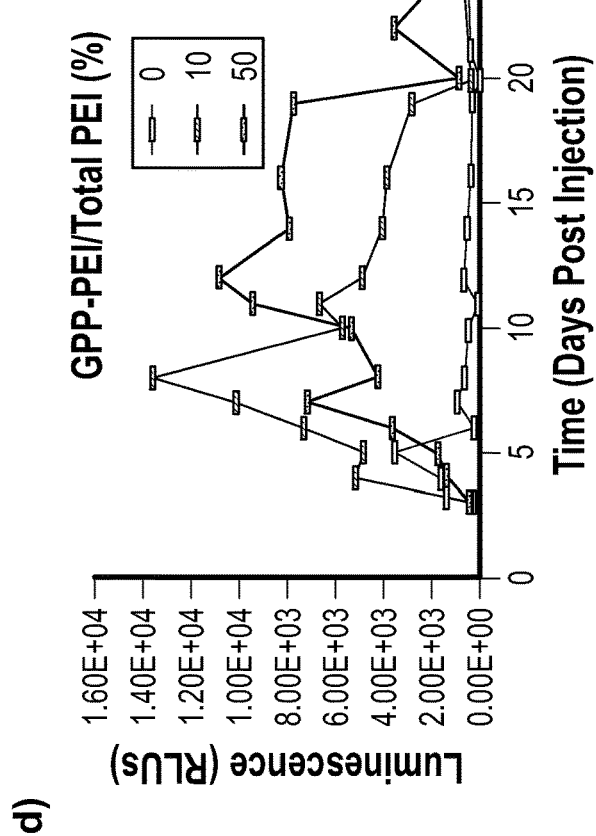
Figure 12:
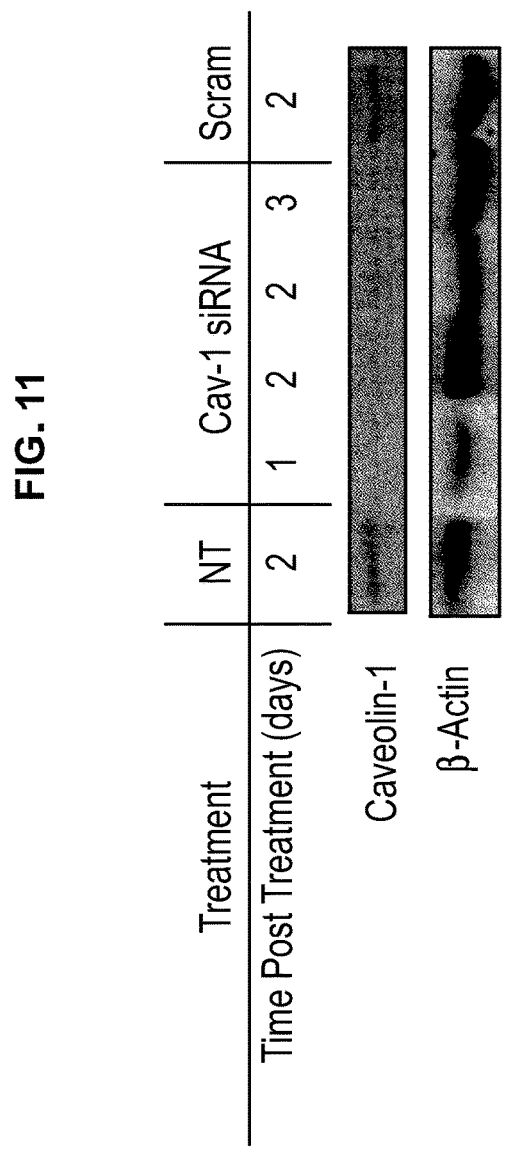

FIG. 12 shows caveolin-1 silencing. The extent of caveolin-1 silencing post treatment was assessed using a Western blot at different time points after treatment.

Figure 13:
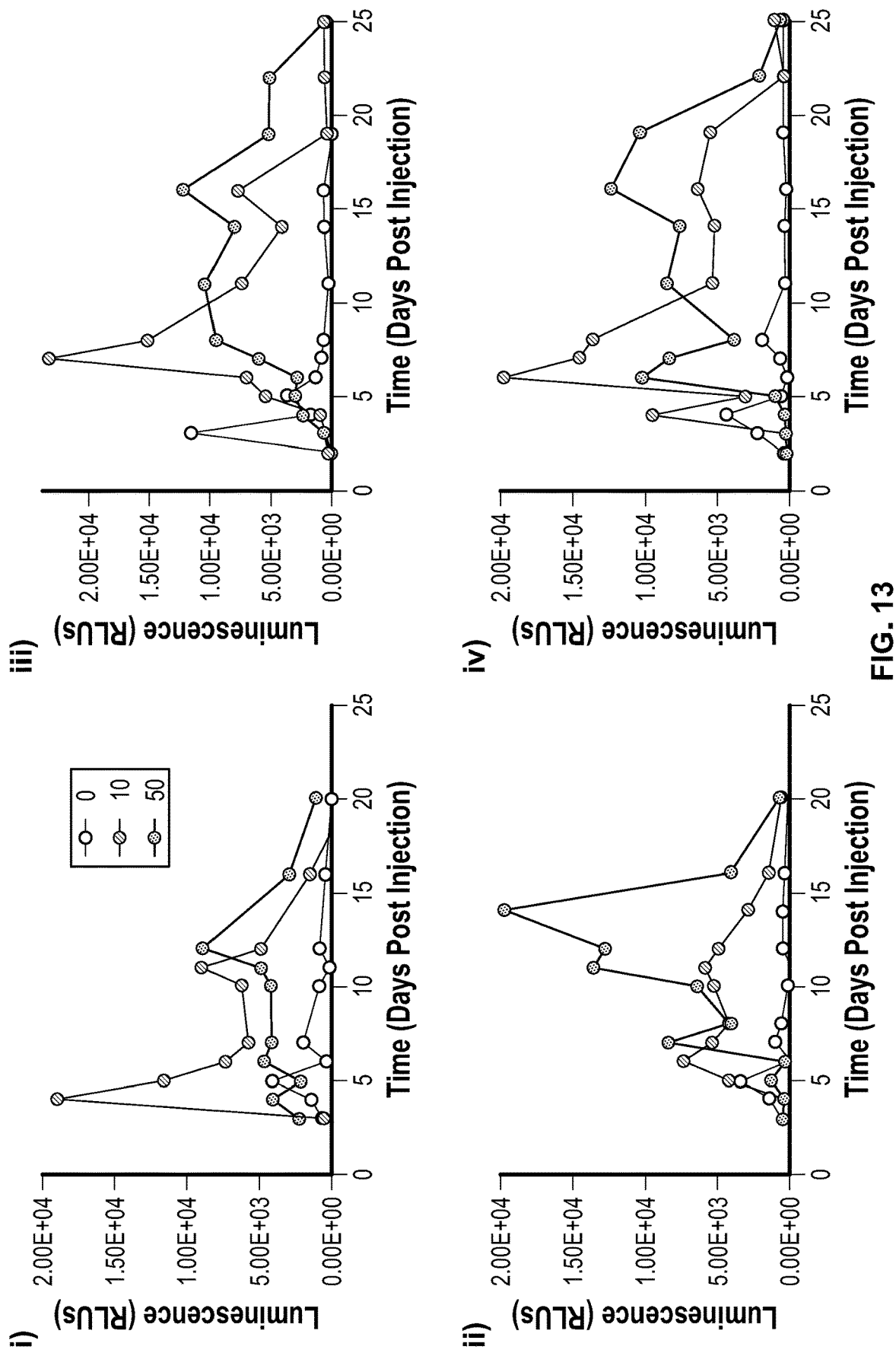

FIG. 13 shows additional replicates in the in vivo expression model. The murine ECM-depot model was replicated in multiple mice (n=4). Quantitative analysis of luciferase expression in four mice is shown in panels (i), (ii), (iii) and (iv), reflecting the expression profiles and the trends facilitated by CMP-incorporation.

Figure 14:
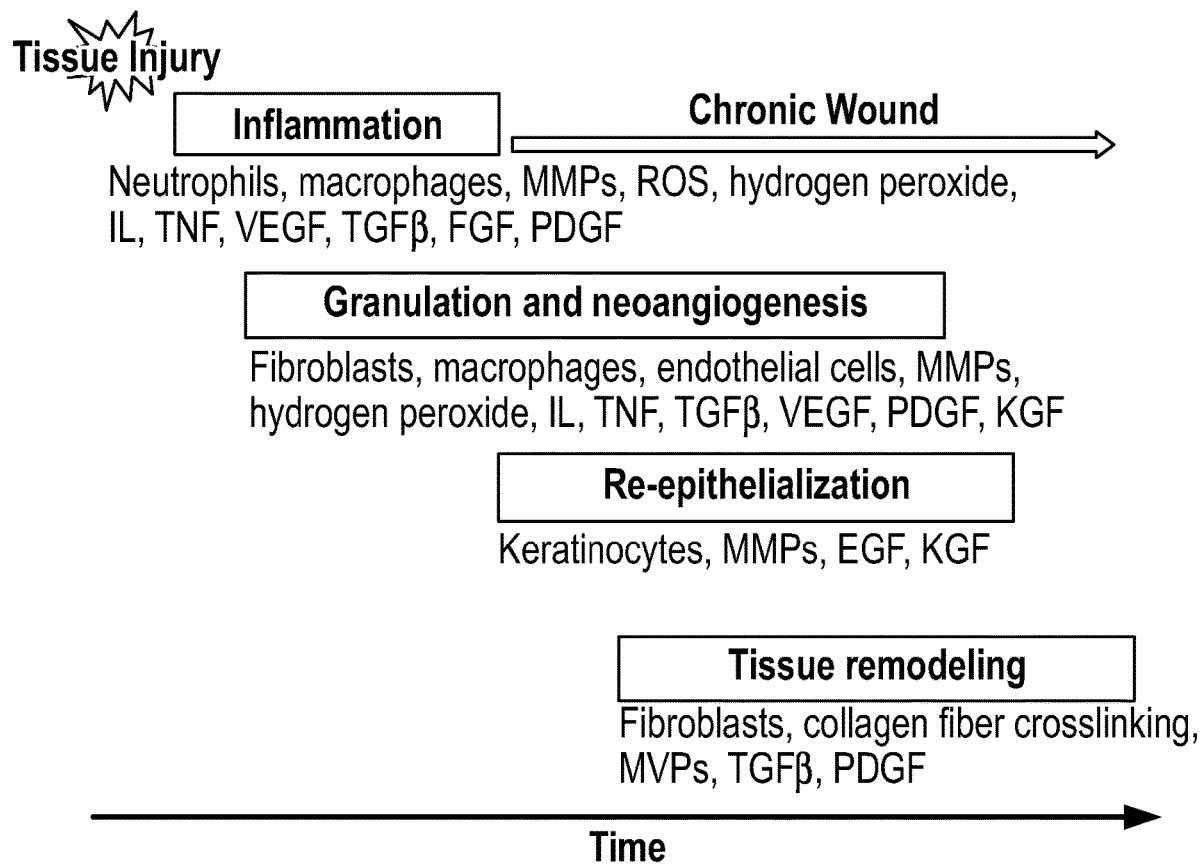

FIG. 14 shows a summary of vital healing factors that are needed during the 4-step healing process. a) A timeline outlines when the vital healing factors (GFs, cytokines, and other healing components) are involved in each step of wound repair. b) A table identifying the processes the vital healing factors mediate. Notably, individual factors are required for differing time periods depending on their roles. The majority of processes underlying repair require multiple integral factors.

Figure 15:
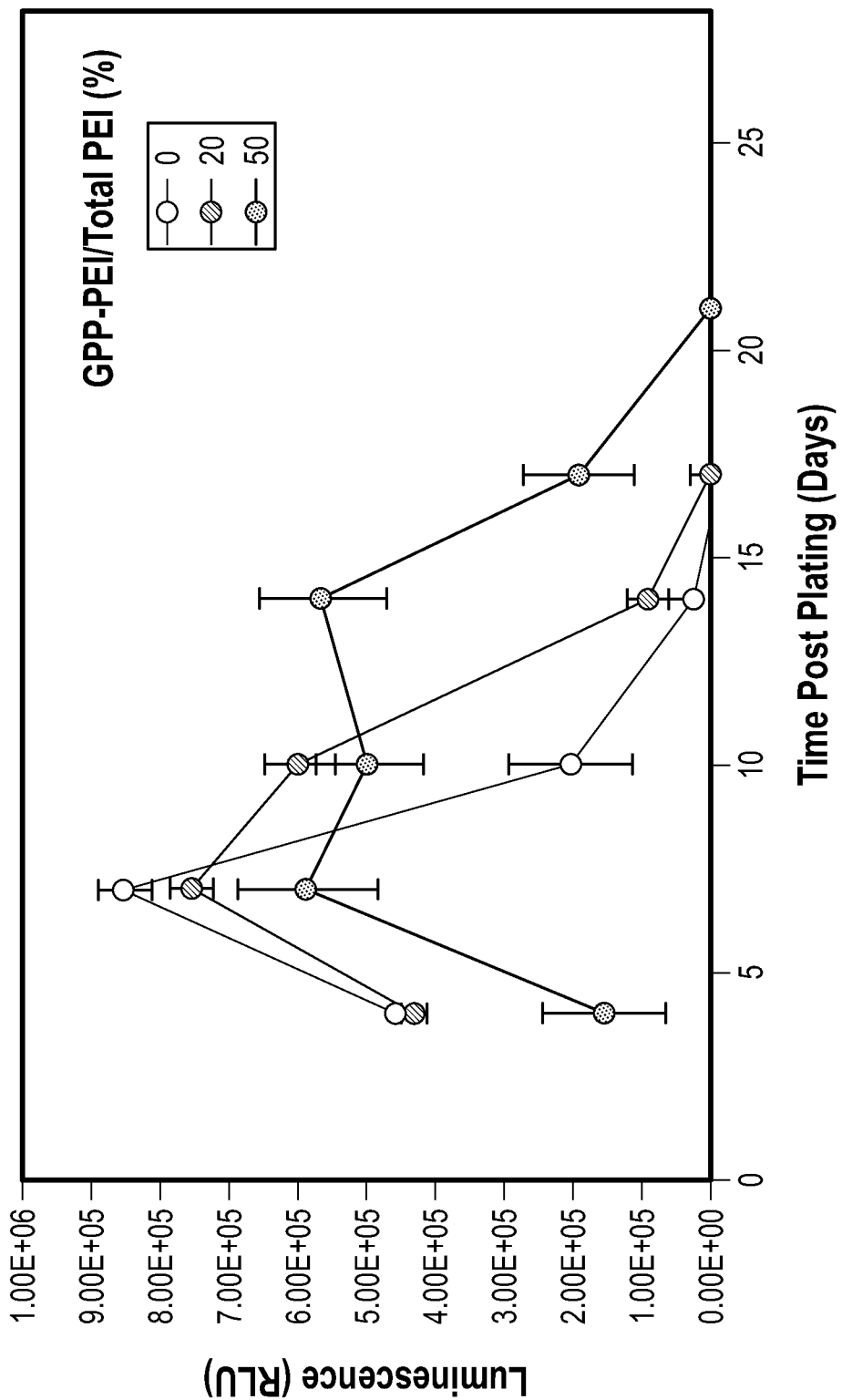

FIG. 15 shows the expression of GLuc facilitated by collagen/fibrin co-gels. Expression of GLuc was assessed via detection of luminescence in conditioned media replaced at each time point. Each set of data points represents the mean±standard deviation for a total of 3 separately prepared and analysed samples.

Figure 16:
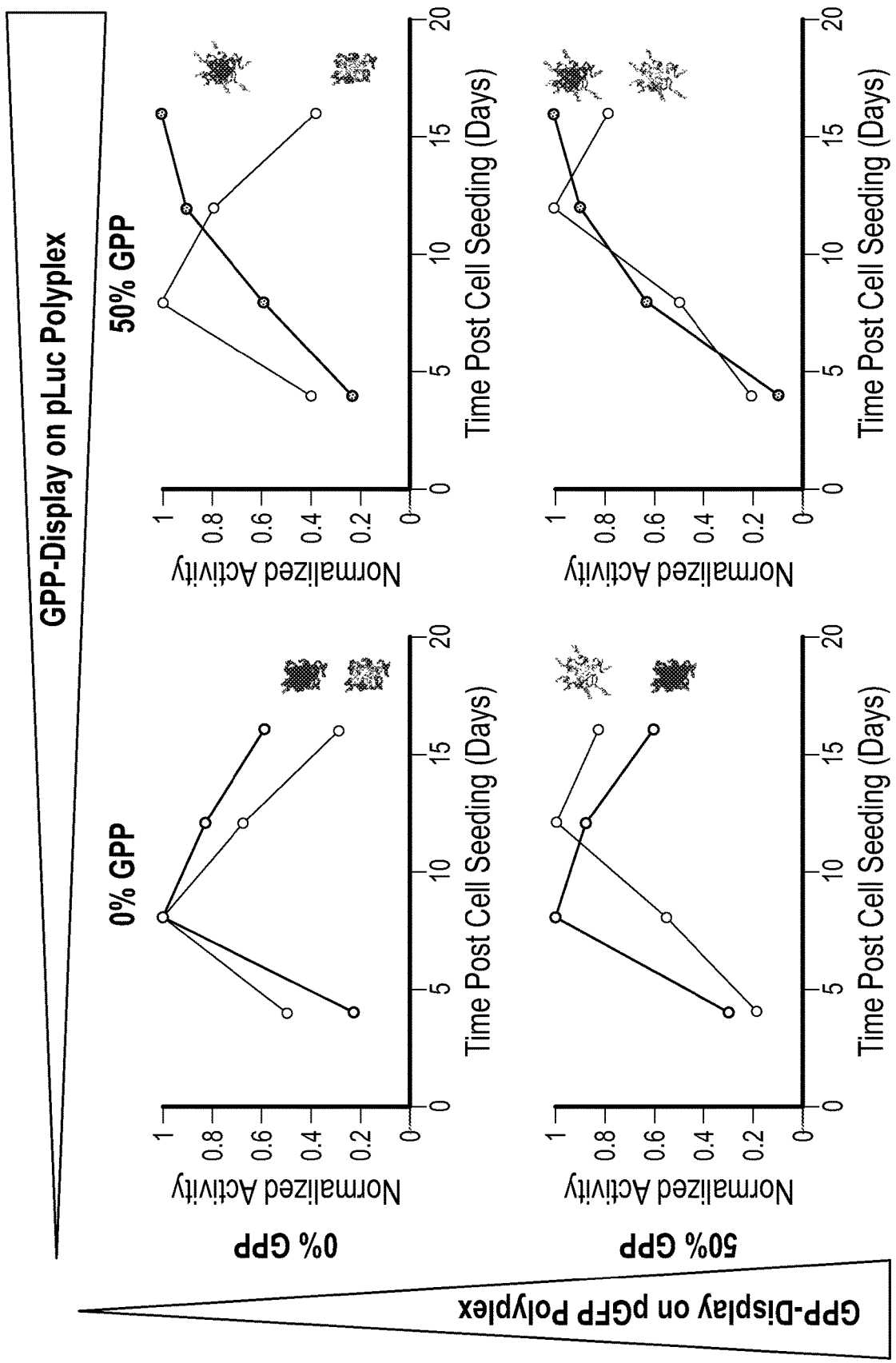

FIG. 16 shows tailored gene delivery/expression of GFP (circles) and GLuc (triangles) in collagen/fibrin co-gels. The effect of different levels of GPP-modification on GLuc and GFP expression was assessed via detection of luminescence and fluorescence respectively. To compare the expression, readings were normalized by the maximum luminescence or fluorescence readings. Each data point represents the mean±standard deviation for a total of 3 separately prepared and analysed samples.

Figure 17:
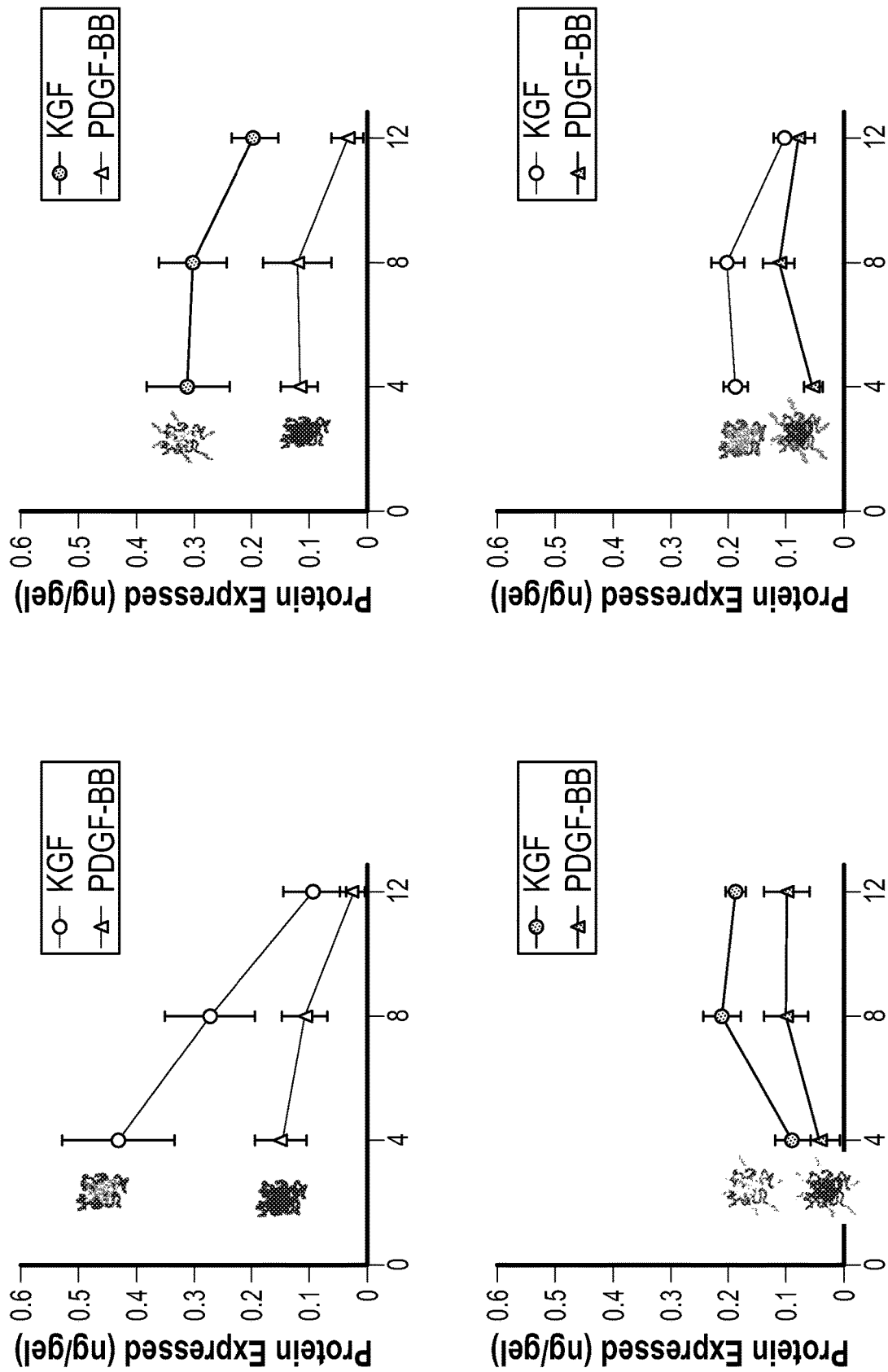

FIG. 17 shows tailored gene delivery/expression of GFs in collagen/fibrin co-gels via varying CMP display. The expression of PDGF-BB (triangles) and KGF (circles) was monitored within the same samples via ELISA. Empty markers indicate the application of unmodified polyplex and black markers indicate the application of 50% GPP-PEI modified polyplex. The data represent the mean+/−standard deviation of 3 separately prepared and analyzed samples.

Figure 18:
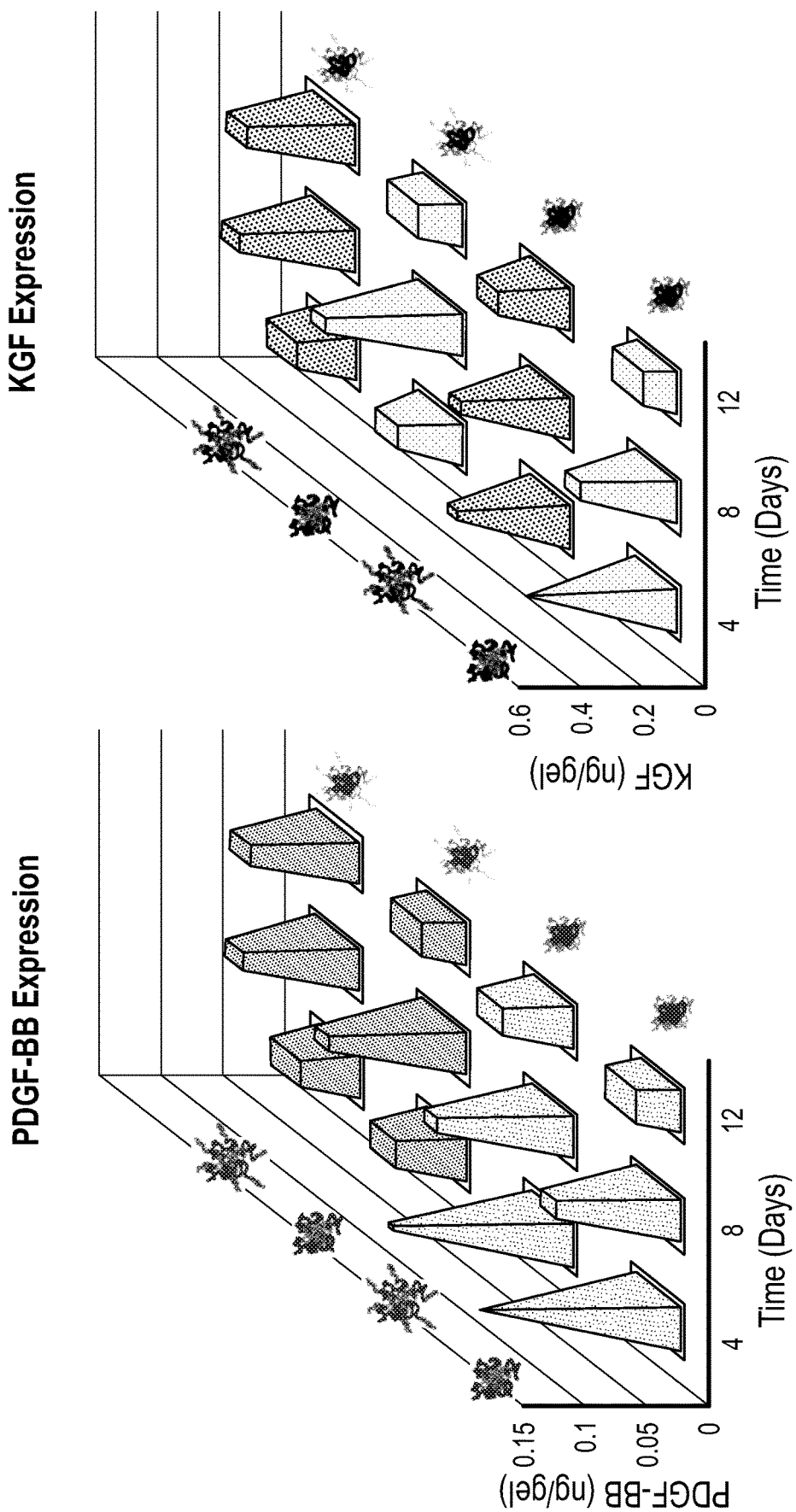

FIG. 18 shows the expression of PDGF-BB and KGF that was monitored within the same samples via ELISA. The data represent the mean+/−standard deviation of 3 separately prepared and analyzed samples.

DETAILED DESCRIPTION OF THE INVENTION

The present invention provides a collagen-mimetic peptide (CMP) mediated in vivo delivery method for polyplexes carrying nucleic acids, including genes encoding desirable proteins such as growth factors, as well as the CMP/polyplex/collagen compositions.

A composition for delivering a polyplex into cells is provided. The polyplex comprises at least one polymer and at least one polynucleotide. The composition comprises at least one collagen-mimetic peptide (CMP), the polyplex and collagen fragments. The CMP is bound to the polyplex. The CMP is also bound to the collagen fragments. The collagen fragments may be networked.

The cells may be any types of cells. Examples of the cells include fibroblast cells, mesenchymal stem cells, macrophages, and keratinocytes. The cells may be in a subject. In some embodiments, the cells are at a wound in the subject.

The term "subject" used herein refers to a mammal, for example, a mouse or human. In some embodiments, the subject is a patient having a wound.

The term "collagen fragments" used herein refers to any segment of collagen protein that is released by degradation of collagen gel, collagen network, collagen film, collagen sponge, or another type of collagen. The collagen fragments may be fragments of any collagen. The collagen may be selected from the group consisting of Type I collagen, Type II collagen, Type III collagen, Type IV collagen, Type V collagen, and combinations thereof. The collagen fragments may be insoluble in, for example, water. The collagen fragments may be prepared by digesting collagen with a protease.

The protease may be metalloproteinase (MMP). In one embodiment, the collagen fragments are obtained by digesting collagen with collagenase.

The term "networked" used herein refers to one or more collagen protein molecules that are covalently or non-covalently linked together comprising one or more linked collagen molecules.

The CMP may be any peptide that is capable of binding collagen or collagen fragments. The CMP may be GPP ((GPP)$_m$GPRGEKGERGPR(GPP)$_n$GPCCG, wherein the sum of m and n is 4 or more (SEQ ID NO: 1)), GPO ((GPO)$_m$GEKGER(GPO)$_n$GGCG, wherein the sum of m and n is 6 or more (SEQ ID NO: 2)), or a combination thereof.

The CMP may have the sequence of (GPP)$_3$GPRGEKGERGPR(GPP)$_3$GPCCG (SEQ ID NO: 3) or (GPO)$_4$GEKGER(GPO)$_4$GGCG (SEQ ID NO: 4). The CMP may have the sequence (GPP)$_m$, wherein m is 10 or more. The CMP may have the sequence (GPO)$_m$, wherein m is 6 or more. The CMP may include other cell binding sequences, for example, GEKGER (SEQ ID NO: 5) or GFOGER (SEQ ID NO: 6). O is hydroxyproline.

The CMP may be bound to the polyplex via a covalent linkage or a noncovalent linkage.

The polynucleotide in the polyplex may be DNA, RNA or a combination thereof. The polynucleotide may encode at least one protein, for example, two or more proteins. For example, the encoded proteins may comprise one growth factor or two or more growth factors. The growth factor may be selected from the group consisting of epidermal growth factor (EGF), fibroblast growth factor (FGF), hepatocyte growth factor (HGF), insulin-like growth factor (IGF), keratinocyte growth factor (KGF), platelet-derived growth factor (PDGF), transforming growth factor (TGF), transforming growth factor-β (TGF-β), transforming growth factor-α (TGF-α) and vascular endothelial growth factor (VEGF). In one embodiment, the polynucleotide encodes platelet-derived growth factor-BB (PDGF-BB).

The polynucleotide may encode at least one silencing RNA capable of suppressing expression of at least one protein, for example, two or more proteins. For example, the proteins may comprise one, two or more inflammatory cytokines. The inflammatory cytokine may be selected from the group consisting of the interleukin family of proteins, the interferon family of proteins, and tumor necrosis factor-α (TNF-α).

The polymer in the polyplex may be any polymer suitable for carrying a polynucleotide. For example, the polymer may comprise polyethylenimine (PEI).

The composition may further comprise an extracellular matrix (ECM) component. The ECM component may be fibrin, fibronectin, laminins, ECM proteoglycans, ECM glycosaminoglycans or a combination thereof.

The composition may further comprise a protease. The protease may be a matrix metalloproteinase (MMP). The MMP may be collagenase.

The composition may be in any form. The composition may be in the form of a gel, film, patch or sponge. The composition may be a collagen-based dressing.

The term "collagen-based dressing" as used herein refers to any composition comprising collagen that can be topically applied, such as to the surface of a wound. A collagen-based dressing may be in the form of a gel, film, patch, or sponge. The collagen-based dressing according to the present invention has the potential to improve and/or accelerate wound repair. This dressing offers the same benefits of current FDA-approved, collagen-based dressings with the additional advantage of being able to facilitate tailorable nanostructure delivery via CMP modification. Varying CMP display has the capacity to tailor both the extent and duration of nanostructure delivery from collagen-based dressings. Furthermore, the use of mixtures of nanostructures with different amounts of CMPs can be used to create complex delivery profiles, and it also can be utilized to deliver a diverse range of nanostructure cargoes at their respective, optimized dosages. The serum-stable, reversible nature of CMP/collagen hybridization also has been demonstrated to encourage both localized delivery of nanostructure cargoes as well as cellular association/endocytic uptake of nanostructures through continued association with collagen/collagen fragments, which is vital when delivering certain nanostructures. CMP design via the inclusion of integrin-binding sequences/charged amino acids also has been shown to engage cells. Additionally, unlike previous delivery methods, CMP modification may have the ability to further promote localized delivery post-release from the dressing via hybridization with the surrounding collagen-rich tissues.

Varying the display of CMPs on DNA-carrying nanostructures, such as polyethylenimine (PEI)-DNA polyplexes, has the capacity to tailor release/retention of DNA and improve overall gene transfer activity. In contrast, most previous studies involving CMPs have employed CMPs to bind to collagen for labeling with dyes or other detectable agents. No prior studies by others have reported the modification of polyplexes with CMPs, especially for in vivo delivery of nucleic acids into cells. Furthermore, CMP modification allows the stable integration of nanostructures into a biomaterial which has been demonstrated to reduce required dosages of included therapeutic agents relative to bolus delivery, and also reduces immunogenic/off-target responses and enhances overall transfection efficiencies; these characteristics are vital for the creation of practical, non-viral DNA technologies that are comparable to but potentially safer than the current standard use of viral DNA. CMP/collagen-mediated delivery also is distinguished by the ability of the CMPs to act as a multipurpose tool mediating delivery from collagen, facilitating cellular uptake, and encouraging continued localization in a tissue or body site through prolonged association with collagens, unlike most delivery methods which rely on encapsulation, non-specific biomaterial-therapeutic interactions, and/or multiple/complex technologies to achieve a similar effect. Enhancements in DNA/collagen activity have been observed in an in vitro wound model, in which CMP-mediated increases in PDGF-BB expression enhanced wound closure rates (see Example 1). Enhancements in DNA/collagen activity were shown to translate in an in vivo model, in which CMP modification enabled localized transgene expression for 10-fold longer time periods with average expression levels that were up to 2-orders of magnitude higher (see Example 2). Successful translation to an in vivo model was a marked achievement as the majority of gene delivery methods fail to transfer genes efficiently in vivo.

A collagen-based dressing of the present invention provides numerous advantages. First, the collagen-based dressing tailors nanostructure release/retention and promotes localized, cell-triggered delivery of nanostructure cargoes from collagen-containing scaffolds through CMP-collagen hybridization. Collagen-mimetic peptides, consisting of glycine-proline-hydroxyproline/proline tripeptide motifs, have been widely demonstrated to have a unique affinity for natural collagen. The targeted binding is attributed to a triple helix hybridization process between the CMP and natural collagen and has already been utilized to robustly modify collagen, both in vivo and in vitro, with a myriad of cargoes including growth factors (GFs). We have successfully utilized collagen-CMP hybridization to modify collagen with nucleic acids and to tailor release of nanostructures containing nucleic acids through both varying the amount of CMP displayed on cargoes (Examples 1 and 2) and utilizing mixtures of nanostructure cargoes modified to different extents (Examples 1 and 3). CMP/polyplex/collagens have been shown to sequester active gene constructs for over a month, a relevant time frame for wound healing; preserve gene transfer activity in the presence of serum proteins such as DNases; and stimulate DNA release and gene activation in response to cell-triggered collagen remodeling (Example 2). Control over gene transfer kinetics has been demonstrated in vitro and in an in vivo tissue repair model. The in vivo results strongly suggest CMP modification can also encourage localized delivery post release via association with surrounding collagen-rich tissues (Example 2). Also, the collagen-based dressing enhances cellular association/uptake via stable collagen/collagen fragment association and integration of delivery with collagen turnover (Example 2). The dressing introduces an innovative strategy to improve control over the dynamics and localization of cargo delivery by harnessing extracellular matrix/collagen turnover/remodeling to synchronize nanostructure cargo release and expression with wound repair cascades. While previous articles have discussed the capacity of cationic CMPs to promote DNA condensation, cellular uptake, and enhanced transfection, the present invention utilizes CMPs as both a tool to mediate release/localization and as a ligand to promote cellular uptake through continued association with collagen fragments rich with integrin binding sites. The introduction of integrin binding sequences into the CMP sequence has been incorporated to further promote cellular uptake and gene expression. CMP modification also appears to promote encapsulation/sustained linkage between nanostructures and collagen fragments, and this sustained linkage appears to direct intracellular delivery (Example 2).

The composition of the present invention may be prepared by stably integrating CMP-modified nucleic acid carriers into a variety of bioactive, collagen-containing scaffolds, including MATRIGEL and collagen/fibrin glues. In turn, nucleic acid-modified scaffolds facilitate cell-mediated delivery of nucleic acids via collagen-remodeling pathways in a highly tailorable manner through variation of CMP sequence and display on the carriers. Subsequently, efficient and controlled nucleic acid delivery can be used to up- or down-regulate protein expression.

A method of delivering a polyplex into cells is provided. The cells are in a subject. The polyplex comprises at least one polymer and at least one polynucleotide. The method comprises administering an effective amount of a composition to the cells. The composition comprises at least one collagen-mimetic peptide (CMP), the polyplex and collagen or fragments thereof. The CMP is bound to the polyplex. The CMP may be bound to the polyplex via a covalent linkage or a noncovalent linkage. The CMP is also bound to the collagen or fragments thereof. The polynucleotide may be DNA, RNA or a combination thereof.

When the polynucleotide encodes at least one protein, the delivery method may further comprise expressing the at least one protein in the cells. The at least one protein may comprise one, two or more growth factors. The growth factor may be selected from the group consisting of epidermal growth factor (EGF), fibroblast growth factor (FGF), hepatocyte growth factor (HGF), insulin-like growth factor (IGF), keratinocyte growth factor (KGF), platelet-derived growth factor (PDGF), transforming growth factor (TGF), transforming growth factor-β (TGF-β), transforming growth factor-α (TGF-α) and vascular endothelial growth factor (VEGF). In one embodiment, the polynucleotide encodes platelet-derived growth factor-BB (PDGF-BB).

When the cells express at least one protein and the at least one polynucleotide encodes at least one silencing RNA capable of suppressing expression of the at least one protein, the delivery method may further comprise suppressing the expression of the at least one protein in the cells. The at least one protein may comprise one, two or more inflammatory cytokines. The inflammatory cytokine may be selected from the group consisting of the interleukin family of proteins, the interferon family of proteins, and tumor necrosis factor-α (TNF-α).

The cells may be at a wound in the subject. The method may further comprise enhancing proliferation of the cells. The method may further comprise enhancing production of extracellular matrix by the cells. The method may further comprise enhancing migration of the cells.

A method of improving wound healing in a subject is provided. The method comprises administering an effective amount of a composition to cells at a wound in the subject and expressing at least one protein in the cells. The composition comprises at least one collagen-mimetic peptide (CMP), a polyplex, and collagen or fragments thereof. The polyplex comprises at least one polymer and at least one polynucleotide. The CMP is bound to the polyplex. The CMP is also bound to the collagen or fragments thereof. The improvement of wound healing may be detected by measuring a reduction in the total wound area and/or by measuring any improvement in the wound histology indicating, for example, a feature of a more normal tissue structure such as angiogenesis and/or formation of a granulation tissue.

When the polynucleotide encodes the at least one protein, the method of improving wound healing may further comprise expressing the at least one protein in the cells. The at least one protein may comprise one, two or more growth factors. The growth factor may be selected from the group consisting of epidermal growth factor (EGF), fibroblast growth factor (FGF), hepatocyte growth factor (HGF), insulin-like growth factor (IGF), keratinocyte growth factor (KGF), platelet-derived growth factor (PDGF), transforming growth factor (TGF), transforming growth factor-β (TGF-β), transforming growth factor-α (TGF-α) and vascular endothelial growth factor (VEGF). In one embodiment, the polynucleotide encodes platelet-derived growth factor-BB (PDGF-BB).

When the cells express at least one protein and the at least one polynucleotide encodes at least one silencing RNA capable of suppressing expression of the at least one protein, the method of improving wound healing may further comprise suppressing the expression of the at least one protein in the cells. The at least one protein may comprise one, two or more inflammatory cytokines. The inflammatory cytokine may be selected from the group consisting of the interleukin family of proteins, the interferon family of proteins, and tumor necrosis factor-α (TNF-α).

A method of enhancing proliferation of cells in a subject is provided. The method comprises administering an effective amount of a composition to the cells and expressing at least one protein in the cells. The composition comprises at least one collagen-mimetic peptide (CMP), a polyplex and collagen or fragments thereof. The polyplex comprises at least one polymer and at least one polynucleotide. The CMP is bound to the polyplex. The CMP is also bound to the collagen or fragments thereof. The enhancement of cell proliferation may be monitored by an assay such as the Alamar Blue assay.

When the polynucleotide encodes the at least one protein, the method of enhancing cell proliferation may further comprise expressing the at least one protein in the cells. The at least one encoded protein may comprise one, two or more growth factors. The growth factor may be selected from the group consisting of epidermal growth factor (EGF), fibroblast growth factor (FGF), hepatocyte growth factor (HGF), insulin-like growth factor (IGF), keratinocyte growth factor (KGF), platelet-derived growth factor (PDGF), transforming growth factor (TGF), transforming growth factor-β (TGF-β), transforming growth factor-α (TGF-α) and vascular endothelial growth factor (VEGF). In one embodiment, the polynucleotide encodes platelet-derived growth factor-BB (PDGF-BB).

When the polynucleotide encodes the at least one silencing RNA capable of suppressing expression of the at least one protein, the method of enhancing cell proliferation may further comprise suppressing the expression of the at least one protein in the cells. The at least one protein may comprise one, two or more inflammatory cytokines. The inflammatory cytokine may be selected from the group consisting of interleukin family of proteins, interferon family of proteins, and tumor necrosis factor-α (TNF-α).

A method of enhancing production of extracellular matrix (ECM) by cells in a subject is provided. The method comprises administering an effective amount of a composition to the cells and expressing at least one protein in the cells. The composition comprises at least one collagen-mimetic peptide (CMP), a polyplex and collagen or fragments thereof. The polyplex comprises at least one polymer and at least one polynucleotide. The CMP is bound to the polyplex. The CMP is also bound to the collagen or fragments thereof. The enhancement of ECM production may be monitored by an assay such as a quantitative polymerase chain reaction (qPCR), Western blotting, or immunostaining.

When the polynucleotide encodes the at least one protein, the method of enhancing ECM production may further comprise expressing the at least one protein in the cells. The at least one encoded protein may comprise one, two or more growth factors. The growth factor may be selected from the group consisting of epidermal growth factor (EGF), fibroblast growth factor (FGF), hepatocyte growth factor (HGF), insulin-like growth factor (IGF), keratinocyte growth factor (KGF), platelet-derived growth factor (PDGF), transforming growth factor (TGF), transforming growth factor-β (TGF-β), transforming growth factor-α (TGF-α) and vascular endothelial growth factor (VEGF). In one embodiment, the polynucleotide encodes platelet-derived growth factor-BB (PDGF-BB).

When the cells express at least one protein and the at least one polynucleotide encodes at least one silencing RNA capable of suppressing expression of the at least one protein, the method of enhancing ECM production may further comprise suppressing the expression of the at least one protein in the cells. The at least one protein may comprise one, two or more inflammatory cytokines. The inflammatory cytokine may be selected from the group consisting of interleukin family of proteins, interferon family of proteins, and tumor necrosis factor-α (TNF-α).

A method of enhancing migration of cells in a subject is provided. The method comprises administering an effective amount of a composition to the cells and expressing at least one protein in the cells. The composition comprises at least one collagen-mimetic peptide (CMP), a polyplex and collagen or fragments thereof. The polyplex comprises at least one polymer and at least one polynucleotide. The CMP is bound to the polyplex. The CMP is also bound to the collagen or fragments thereof. The enhancement of cell migration may be monitored by an assay such as a scratch migration assay.

When the polynucleotide encodes the at least one protein, the method of enhancing cell migration may further comprise expressing the at least one protein in the cells. The at least one encoded protein may comprise one, two or more growth factors. The growth factor may be selected from the group consisting of epidermal growth factor (EGF), fibroblast growth factor (FGF), hepatocyte growth factor (HGF), insulin-like growth factor (IGF), keratinocyte growth factor (KGF), platelet-derived growth factor (PDGF), transforming growth factor (TGF), transforming growth factor-(TGF-β), transforming growth factor-α (TGF-α) and vascular endothelial growth factor (VEGF). In one embodiment, the polynucleotide encodes platelet-derived growth factor-BB (PDGF-BB).

When the cells express at least one protein and the at least one polynucleotide encodes at least one silencing RNA capable of suppressing expression of the at least one protein, the method of enhancing cell migration may further comprise suppressing the expression of the at least one protein in the cells. The at least one protein may comprise one, two or more inflammatory cytokines. The inflammatory cytokine may be selected from the group consisting of interleukin family of proteins, interferon family of proteins, and tumor necrosis factor-α (TNF-α).

According to the method of delivering a polyplex into cells, improving wound healing, enhancing proliferation by cells, enhancing production of extracellular matrix by cells, or enhancing migration of cells, the composition may be in the form of a gel, film, patch, or sponge. The composition may further comprise an extracellular matrix (ECM) component. The ECM component may be selected from the group consisting of fibrin, fibronectin, laminins, ECM proteoglycans, ECM glycosaminoglycans and combinations thereof. The composition may further comprise a matrix metalloproteinase (MMP). The MMP may be collagenase. The CMP may be GPP ((GPP)$_m$GPRGEKGERGPR(GPP)$_n$GPCCG, wherein the sum of m and n is 4 or more (SEQ ID NO: 1)), GPO ((GPO)$_m$GEKGER(GPO)$_n$GGCG, wherein the sum of m and n is 6 or more (SEQ ID NO: 2)), or a combination thereof. The CMP may have the sequence of (GPP)$_3$GPRGEKGERGPR(GPP)$_3$GPCCG (SEQ ID NO: 3) or (GPO)$_4$GEKGER(GPO)$_4$GGCG (SEQ ID NO: 4). The CMP may have the sequence (GPP)$_m$, wherein m is 10 or more. The CMP may have the sequence (GPO)$_m$, wherein m is 6 or more. The CMP may include other cell binding sequences, for example, GEKGER (SEQ ID NO: 5) or GFOGER (SEQ ID NO: 6). O is hydroxyproline. The polymer may comprise polyethylenimine (PEI). The collagen may be selected from the group consisting of Type I collagen, Type II collagen, Type III collagen, Type IV collagen, Type V collagen, and combinations thereof. The collagen or fragments thereof may be networked. The collagen or fragments thereof may be insoluble in, for example, water.

The term "an effective amount" as used herein refers to an amount of a composition required to achieve a stated goal (e.g., delivering a polyplex into cells, improving wound healing, enhancing proliferation by cells, enhancing production of extracellular matrix by cells, or enhancing migration of cells). The effective amount of the composition may be selected to achieve the stated goal, with one or multiple doses of the composition. The effective amount of the composition comprising a CMP, a polyplex and collagen or fragments thereof may vary depending upon the stated goals, the physical characteristics of the subject, the existence of related or unrelated medical conditions, the nature of the CMP, polyplex and/or collagen or fragments thereof, the composition, the means of administering the composition to the subject, and the administration route. A specific dose for a given subject may generally be set by the judgment of a physician. The composition may be administered to the subject in one or multiple doses.

The term "about" as used herein when referring to a measurable value such as an amount, a percentage, and the like, is meant to encompass variations of ±20% or ±10%, more preferably ±5%, even more preferably ±1%, and still more preferably ±0.1% from the specified value, as such variations are appropriate.

Example 1. Integration of Growth Factor Gene Delivery with Collagen-Triggered Wound Repair Cascades Using Collagen-Mimetic Peptides Growth factors (GFs) play vital roles in wound repair. Many GF therapies have reached clinical trials, but success has been hindered by safety concerns and a lack of efficacy. Previously, we presented an approach to produce protein factors in wound beds through localized gene delivery mediated by biomimetic peptides. Modification of polyethylenimine (PEI) DNA polyplexes with collagen-mimetic peptides (CMPs) enabled tailoring of polyplex release/retention and improved gene transfer activity in a cell-responsive manner. In this work, CMP-mediated delivery from collagen was shown to improve expression of platelet-derived growth factor-BB (PDGF-BB) and promote a diverse range of cellular processes associated with wound healing, including proliferation, extracellular matrix production, and chemotaxis. Collagens were pre-exposed to physiologically-simulating conditions (complete media, 37° C.)

for days to weeks prior to cell seeding to simulate the environment within typical wound dressings. In cell proliferation studies, significant increases in cell counts were demonstrated in collagen gels containing CMP-modified polyplex vs. unmodified polyplex, and these effects became most pronounced following prolonged pre-incubation periods of greater than a week. Collagen containing CMP-modified polyplexes also induced a 2-fold increase in gel contraction as well as enhanced directionality and migratory activity in response to cell-secreted PDGF-BB gradients. While these PDGF-BB-triggered behaviors were observed in collagens containing unmodified polyplexes, the responses withstood much longer preincubation periods in CMP-modified polyplex samples (10 d vs. <5 d). Furthermore, enhanced closure rates in an in vitro wound model suggested that CMP-based PDGF-BB delivery may have utility in actual wound repair and other regenerative medicine applications.

Introduction

Identification of the growth-promoting activities of the secreted, signaling proteins known as growth factors (GFs) has inspired much anticipation about their potential in tissue repair applications, particularly in refractory wounds and other hard-to-heal tissues. These multifunctional and potent proteins play fundamental roles in a range of regenerative activities including regulation of cellular proliferation, chemotaxis, and extracellular matrix synthesis, with their activity often recognizable in the picomolar range. For example, altered cell phenotypes and an aberrant extracellular environment in chronic wounds are factors recognized to reduce GF production, stability, accessibility, and activity, further complicating the already intricate reparative processes. Accordingly, multiple preclinical studies and industry sponsored trials have examined the efficacy of topical and sustained release GF formulations in chronic wounds. In 1997, Becaplermin/REGRANEX (Systagenix; Skipton, UK), a topical platelet-derived growth factor-BB (PDBF-BB) gel, became the first successful, FDA-approved growth factor treatment for the treatment of diabetic foot ulcers (DFUs); however, existing GF therapies exhibit only modest clinical utility overall. Based on clinical trials, the FDA concluded that topically-applied PDGF-BB increased the number of healed DFU patients by less than 10%, and while the application of PDGF-BB has been shown to augment wound repair in several human studies, many were never published due to a lack of efficacy. Clinical failure has largely been blamed on incompatibilities of traditional GF therapies with the hostile, irregular chronic wound environment that limits GF penetration into the wound bed, causes rapid GF degradation due to elevated protease activation, and decreases cellular responses to GFs. Accordingly, extraphysiological, repetitive doses are typically required to achieve therapeutic effects. These dosing regimens increase the danger of GF toxicity, elevate treatments costs, and elevate the risk of substantial off-target effects or even oncogenic responses. New approaches for creating healthy, GF-rich wound beds are essential.

Based on the need for improved wound therapies, promising alternatives include GF gene delivery and the application of biocompatible matrices that can regulate multiple aspects of cell behavior through controlled presentation of extracellular cues. GF gene therapies offer exciting potential benefits for improved GF delivery due to their ability to foster localized, on-demand GF production within the wound bed. In particular, gene-based approaches to GF delivery better mimic endogenous repair responses by allowing host cells to orchestrate sustained GF expression, microlocalization, and activity, which are essential in chronic wound repair due to extended healing over months, spatiotemporal heterogeneity, and elevated protease activation. Because of these characteristics, GF gene therapies have exhibited increased efficacy in experimental wound models as compared with topical delivery approaches, with the capacity to achieve similar healing responses with orders of magnitude less GF (e.g. ~2000-fold less GF expression than a typical topically-applied dose). These observed dosage reductions coupled with the spatiotemporal control achievable via promoter choice/vector design suggest that gene therapies may have exciting potential to create controllable, more effective, and less toxic approaches to deliver GFs. While clinical data on GF gene therapies are limited, localized gene therapy approaches show promise for improved safety and efficacy, and are amongst the most rapidly advancing gene therapies in clinical trials for diseases such as ocular disorders.

In terms of delivery regimens, therapeutic DNA has been incorporated into biomaterial matrices designed to mediate, prolong, and enhance gene transfer while reducing potential off-target and/or immune responses. In addition to providing enhanced gene stability and improved control over release, gene activated matrices (GAMs) provide a permissive environment that promotes cellular ingrowth, increases tissue deposition, triggers in situ production of GFs, and enhances cell health. In fact, the application of collagen-based artificial skins, such as APLIGRAF (Organogenesis) and DERMAGRAFT (Advanced Biohealing), has been shown to enhance chronic wound repair even in the absence of incorporated GFs; however, the incidence of complete closure after a therapeutic trial with engineered skin remained close to 50%, highlighting the need for improved bioactivity. The synergistic effects in wound repair between biomaterials and GF-encoding genes have been demonstrated in numerous studies, such as when collagen-embedded PDGF-B DNA was shown to increase the formation of new granulation tissue by up to 52% and re-epithelization by up to 34%, as compared to collagen alone, in a dermal ulcer model in rabbits. The same materials stimulated a more than 4-fold increase in cell repopulation over a 10-day period in an ex vivo human gingival defect repair model.

Additional studies demonstrate the clear advantages for natural and synthetic GAMs in controlling gene transfer efficacy, with some approaches reporting detectable gene expression in vivo over a few weeks via diffusion- and/or degradation-controlled retention/release of entrapped plasmids or polyplexes. Furthermore, improvements in spatial and temporal control over the delivery of DNA from GAMs have been achieved through the immobilization of DNA onto scaffolds through better defined interactions, such as biotin-avidin or antigen-antibody binding. For instance, biotinylation of PEI DNA polyplexes increased retention onto avidin-modified collagen by as much as 30%, resulting in a 2-fold increase in transfection efficiency compared to that observed in collagen encapsulating unmodified PEI DNA polyplexes. However, while current gene-based therapeutics are very promising, they often have failed in translation due to continued concerns of off-target and immune responses, as well as inefficiencies in gene transfer efficacy in protein/serum-rich environments. Moreover, the majority of existing GAM technologies are unfit for many tissue repair applications due to the complexity of the healing process, which can involve extended healing periods over months and multiple out-of-phase healing cascades occurring simultaneously within repair sites.

In our prior studies, a novel approach with the potential to overcome these issues through application of collagen-mimetic peptides (CMPs) in gene delivery was demonstrated. CMPs have a natural affinity for collagen driven by a reversible strand-invasion process that can be tailored with relative ease by altering CMP sequence and molecular weight. This unique ability has been exploited to modify extracted collagens in vitro, as well as to target and bind remodeling collagens in vivo, using various CMP-linked cargoes such as GFs. Our labs were the first to use CMPs to modify collagen with DNA. Specifically, CMP display on DNA-polyethylenimine (PEI) polyplexes was shown to have the capacity to improve control over both the extent and duration of gene expression in vitro. Through varying CMP display, DNA in vitro release/retention was tailored for over a month, two times longer than the retention/release periods of unmodified polyplexes. CMP modification also maintained polyplex activity in serum-supplemented media for up to 2 weeks, in contrast with most gene delivery approaches which report losses to nuclease degradation within hours. Additionally, we demonstrated the novel ability to "hijack" collagen remodeling, a process that occurs in excess in the protease-rich chronic wound environment. Whereas previous studies have utilized proteolytically-sensitive materials to synchronize cell invasion with therapeutic release, the reversible, serum-stable nature of the CMP-collagen interaction allowed for continued association with collagen fragments, confirmed through colocalization microscopy studies. The alteration in polyplex composition resulted in enhanced polyplex activity linked to an increased capacity to preserve DNA integrity in the presence of serum and an increase in caveolar uptake, a pathway linked to high efficiency gene transfer. Furthermore, the benefits of using collagen remodeling as a driver for gene release and activity were confirmed in a more complicated, in vivo model in which transgene expression was localized and extended from 3 to over 20 days (see Example 2). This versatile approach, which capitalizes on collagen remodeling, has the potential to efficiently augment any collagen-containing device with gene expression and has tremendous potential for overcoming non-viral gene delivery obstacles in multiple regenerative medicine applications.

In this work, our objective was to demonstrate the benefits of CMP gene delivery for GF expression during wound healing. For this purpose, we chose PDGF-BB as a target GF due to its well established ability to effect a diverse range of cellular processes associated with wound healing, including proliferation, extracellular matrix production, and chemotaxis. Our studies demonstrated that CMP display on PEI polyplexes encoding PDGF-B significantly enhanced polyplex activity, even after prolonged exposure to physiologically-simulating conditions mimicking the wound environment. PDGF-BB levels were up to 4-fold greater in CMP-modified samples, vs. unmodified samples, and maintained up to a 3-fold increase in expression even after the gene-modified collagen scaffolds were exposed to serum for 7 days at 37° C. Various desirable cell repair behaviors were also enhanced by CMP modification. Cell counts were increased by up to 75% in CMP scaffolds, and CMP-induced differences in proliferation remained significant even after a 10-day serum preincubation. Collagen remodeling and cell migration were also enhanced by CMPs, as highlighted through collagen contraction assays and cell migration studies. Moreover, we demonstrated promising capacity for the CMP-modified DNA/collagen gels in wound scaffold applications, based on increased cell densities and accelerated migration in collagen-based, 3-D wound models. Defects treated with CMP-modified collagens reached approximately 90% wound closure after 10 days of treatment, whereas wound closure never exceeded 40% using scaffolds containing unmodified polyplex. Moreover, collagen scaffolds supplemented with recombinant PDGF-BB (rPDGF-BB) at levels comparable to the maximum expression levels exhibited no differences in cell invasion/proliferation from collagen alone; in fact, rPDGF-BB levels had to be increased by an order of magnitude to achieve similar bioactivity as in CMP-modified scaffolds. The increase in gene stability and improved expression associated with CMP-based gene delivery may translate in vivo, aiding in multiple aspects of wound repair. Furthermore, our findings stress the advantages of GF gene therapies for providing substantial reductions in GF exposure and thereby reducing concerns with both cost and safety. These advantages highlight the potential of CMP-triggered gene delivery to enhance numerous collagen-based materials through improved non-viral gene delivery regimens.

Material and Methods

Materials

Type I bovine collagen was purchased from Advanced BioMatrix (San Diego, CA) and pCMV-PDGF-B plasmid was purchased from Origene Technologies, Inc. (Rockville, MD). pDNA was amplified in NEB 5-α electrocompetent *E. coli* purchased from New England Biolabs and purified from bacterial culture using a Qiagen Megaprep Kit (Valencia, CA), following the manufacturer's protocols. The Mouse/Rat PDGF-BB Quantikine enzyme-linked immunosorbent assay (ELISA) kit was purchased from R&D Systems (Minneapolis, MN). Fmoc-protected amino acids were purchased from Anaspec (Fremont, CA). H-Rink amide CHEMMATRIX resin was purchased from PCAS Biomatrix (Quebec, Canada). O-Benzotriazole-N,N,N',N'-tetramethyl-uronium-hexafluoro-phosphate (HBTU) was purchased from Novabiochem (San Diego, CA). High performance liquid chromatography (HPLC)-grade N,N-dimethyl formamide (DMF), acetonitrile, trifluoroacetic acid (TFA), CELL-TRACKER Deep Red, and cell culture reagents, including Dulbecco's modified Eagle's medium (DMEM), Dulbecco's phosphate buffered saline (PBS), penicillin-streptomycin (P/S), and trypsin were purchased from Fisher Scientific (Fairlawn, NJ). Fetal bovine serum (FBS) was purchased from Corning (Manassas, MA). Collagenase I was purchased from Worthington Biochemical Corp (Lakewoord, NJ). Piperidine, 4-methylmorpholine, all cleavage cocktail components, and branched PEI (25 kDa) were purchased from Sigma-Aldrich (St. Louis, MO). The ORIS cell migration assay kit was purchased from Platypus Technologies (Madison, WI).

Preparation of Modified Collagen Gels

The CMP [GPP: (GPP)$_3$GPRGEKGERGPR(GPP)$_3$ (SEQ ID NO: 3)] used in prior studies was synthesized using Fmoc solid phase peptide synthesis and purified using reverse phase-HPLC. GPP was conjugated to PEI using Michael-type addition chemistry and the conjugate (GPP-PEI) was used to prepare GPP-modified polyplexes as previously described (Urello et al., *Journal of Materials Chemistry B.* 2014; 2(46):8174-8185). Using a variation of well-established polyplex formation protocols, equivolumetric solutions of PEI and DNA in 20 mM HEPES buffer (pH 6.0) were mixed to produce a final solution with an amine to phosphate ratio (N:P) ratio of 10. To incorporate GPP, the GPP-PEI conjugate was preincubated at 50° C. for 30 minutes to prevent triple-helical hybridization of GPP, and a specified percent of PEI used to create the polyplex was replaced with the GPP-PEI. Collagen gels with GPP-immobilized or encapsulated unmodified polyplexes were prepared by re-suspending dehydrated polyplex in neutralized type I bovine collagen-solution (4 mg/mL, pH 7.4) as previously described (Urello et al., *Journal of Materials Chemistry B*. 2014; 2(46):8174-8185). After a 3 h incubation on ice to allow bubbles to settle and enable GPP-collagen hybridization, the solution was allowed to gel overnight at 37° C.

Quantification of PDGF-BB Expression in Modified Collagens DNA/collagen gels were prepared with 500 µL of DNA/collagen solution in 8 well plates (0.8 cm$^2$ surface area/well). Gels were incubated at 37° C. overnight to allow gelation, after which 200 µL of complete medium (DMEM with 10% FBS and 1% P/S) was added. The gels were then preincubated in complete medium at 37° C. and 5% $CO_2$ for a specified time period ranging from 0 to 14 days to simulate physiological conditions. MMPs and other wound-relevant proteases were purposefully excluded from the pre-treatment step based on wound environment studies that demonstrate localization of proteases in the expressing cells' microenvironment coinciding with the wound edge or adjacent tissues. Subsequently, gels were washed with PBS and DMEM and 20,000 NIH/3T3 cells were seeded per well. Cells were cultured under the same conditions as the pre-incubation. After a 4-day culture, a sandwich ELISA and a direct ELISA were used to determine PDGF-BB concentrations in the conditioned media and in the gels, respectively. PDGF-BB remaining in the gels was recovered through a 72-hour incubation with 500 µL of extraction buffer (10 mg/ml heparin, 2% BSA, 2M sodium chloride, and 0.01% Triton-X in phosphate buffered saline) at 4° C. Released PDGF-BB was quantified using a commercially available Quantikine ELISA kit in a 96-well plate format, according to manufacturer's instructions. A seven-point standard curve was used to quantify the concentrations, spanning a range from 0 to 2000 ng/mL PDGF-BB. Each sample was read twice with a Glomax Multimodal Plate reader (Sigma), and the average of the two readings was used to calculate the concentration of PDGF-BB in the sample. PDGF-BB still remaining in the gel was quantified through use of a direct ELISA. After removal of the extraction buffer, the gels were gently washed twice with PBST (PBS supplemented with 0.05% Tween-20, 5 minutes per wash) and incubated with the anti-mouse/rat PDGF-BB antibody conjugate supplied in the Quantikine ELISA kit (antibody specific for PDGF-BB conjugated to horseradish peroxidase [HRP]) for 2 h at room temperature. Following two 5-minute PBST washes, 300 µL of a 1:1 solution of color reagent A (hydrogen peroxide) and color reagent B (tetramethylbenzidine) were added. Colored solution was removed from each gel after 30 min and a stop solution was added. The Glomax Multimodal Plate reader (Sigma) was then used as described above to determine PDBF-BB concentrations using solutions collected from an empty collagen control gel as a background measurement.

Quantification of Proliferation

DNA/collagen gels were prepared and preincubated for periods ranging from 0 to 14 days as described above. Four days after seeding cells (20,000 NIH/3T3 cells per well), gels/cells were imaged using a Leica DMI6000 B inverted microscope (Wetzlar, Germany), and image analysis tools in ImageJ (National Institutes of Health) were used to count the number of cells per field of view. Cells were subsequently recovered from the gels through use of a collagenase (0.1 U/mL PBS)/Dispase® (0.8 U/mL PBS) digestion solution, as well as gentle pipetting to break the gel apart. After a 45-minute digestion at 37° C., the total cell count was determined using a hemocytometer and compared to the number of cells initially seeded. Samples were analyzed at 4 days to provide time for cellular invasion, transfection, and proliferation while excluding the effects of cellular confluency on cellular behavior.

Contraction Assay

DNA/collagen gels were prepared and preincubated as described above. After a 0- to 10-day preincubation, 20,000 cells were seeded onto the gels. Three days after seeding the cells, gel height was determined by analyzing images taken of the gels with a camera, using a ruler tool in ImageJ. To account for gel irregularities, the gel height for a given gel was determined by averaging the heights measured at 5 set-points in the gel (one point at the center of gel; 2 points at the gel edges, and 2 points equidistant from the prior points). The average gel height reported for each sample was based upon the average of individual gel heights from 5 different samples.

Collagen Bi-Layer Cellular Migration Study

Figure 1:
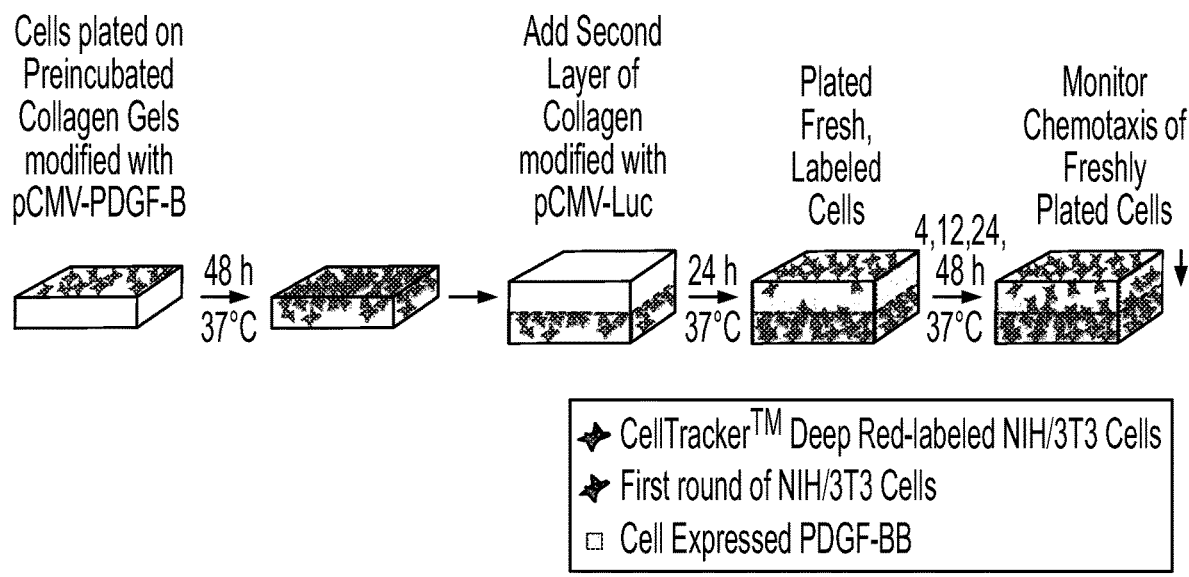
FIG. 1 shows schematic of a collagen bi-layer migration study. NIH/3T3 cells were seeded onto a layer (layer 1) of collagen containing polyplex encoding for platelet-derived growth factor-BB (PDGF-BB). Layer 1 was preincubated in complete culture media containing 10% serum prior to cell plating. After a 48 hr culture of the cells on layer 1, a second layer (layer 2) of collagen (containing pCMV-Luc) was added. Twenty-four hours after the addition of layer 2, additional NIH/3T3 cells were plated on top of layer 2 and migration in response to the cell-expressed PDGF-BB (in layer 1) was monitored.

Layered DNA/collagen gels containing a gradient in cell-expressed PDGF-BB were produced through a multi-step procedure (FIG. 1). First, 200 µL DNA/collagen gels containing PDGF-B-encoding polyplexes were prepared and preincubated in complete media [(10% FBS, 1% P/S) at 37° C. and 5% $CO_2$], as described, to simulate physiological conditions. After a 0- to 10-day preincubation period, 20,000 NIH/3T3 cells were seeded onto the collagen gels and cultured for 2 days under the same conditions as the preincubation to allow cell invasion and transfection. Media was subsequently removed from the gels and a second layer of collagen containing luciferase-encoding polyplex (100 µL of collagen/DNA solution) was added atop each cellularized gel. Following gelation at 37° C. for 2 h, complete media was added to the bi-layer collagen gels. After allowing an additional 24 h for a gradient in PDGF-BB expression to form, 5,000 fresh NIH/3T3 cells (labeled with CELL-TRACKER Deep Red) were plated onto each gel. These cells were pre-labeled with the CELLTRACKER Deep Red dye via the manufacturer's protocol to enable rapid tracking of cell migration, and the cells were plated at a low density (~6,250 cells/cm$^2$) to minimize the effects of cell-induced contraction. A 75% reduction in cell seeding densities lessened contraction in collagen gel height from approximately 16% to 5% over 48 h (data not shown) and migration was monitored using a Leica DMI6000 B inverted microscope (Wetzlar, Germany). All image analysis was performed using ImageJ.

In Vitro Wound Model

3-D in vitro defect wounds were constructed using an ORIS cell migration assay kit. A physical "stopper" barrier was placed in the center of each well of a 96-well plate. 20 µL of collagen solution containing 100,000 NIH/3T3 cells/ mL were added to either side of the stopper (total of 40 µL per well) to ensure the collagen/cell mixture was spread evenly around the stopper. After allowing gelation at 37° C. for 1 h, the stopper was removed, creating uniform, cell-free defects at the center of each well (diameter=2 mm). 20 µL of DNA/collagen solution encoding PDGF-B, prepared as described previously, was immediately added to the defect. In the 20%/50% GPP-modified polyplex samples a ratio of 8:2 (mass of DNA in the 20% vs. 50% GPP-modified polyplex) was used. After allowing gelation to occur for 1 h at 37° C., complete media was added atop each gel and cell invasion into each defect was monitored via Calcein AM staining (5 µM Calcein AM in Opti-MEM). Defect/wound "closure" was analyzed using the thresholding function in the ImageJ MRI Wound Healing Tool (NIH), with the new wound edge defined as the point when the average cell density/fluorescence in the defect matched the average cell density/fluorescence in the area surrounding the defect. Percent wound closure was defined as the fractional area of the defect that has the same cell density as the area surrounding the defect.

Results

Quantification of PDGF-BB Expression in Modified Collagens

Figure 2:
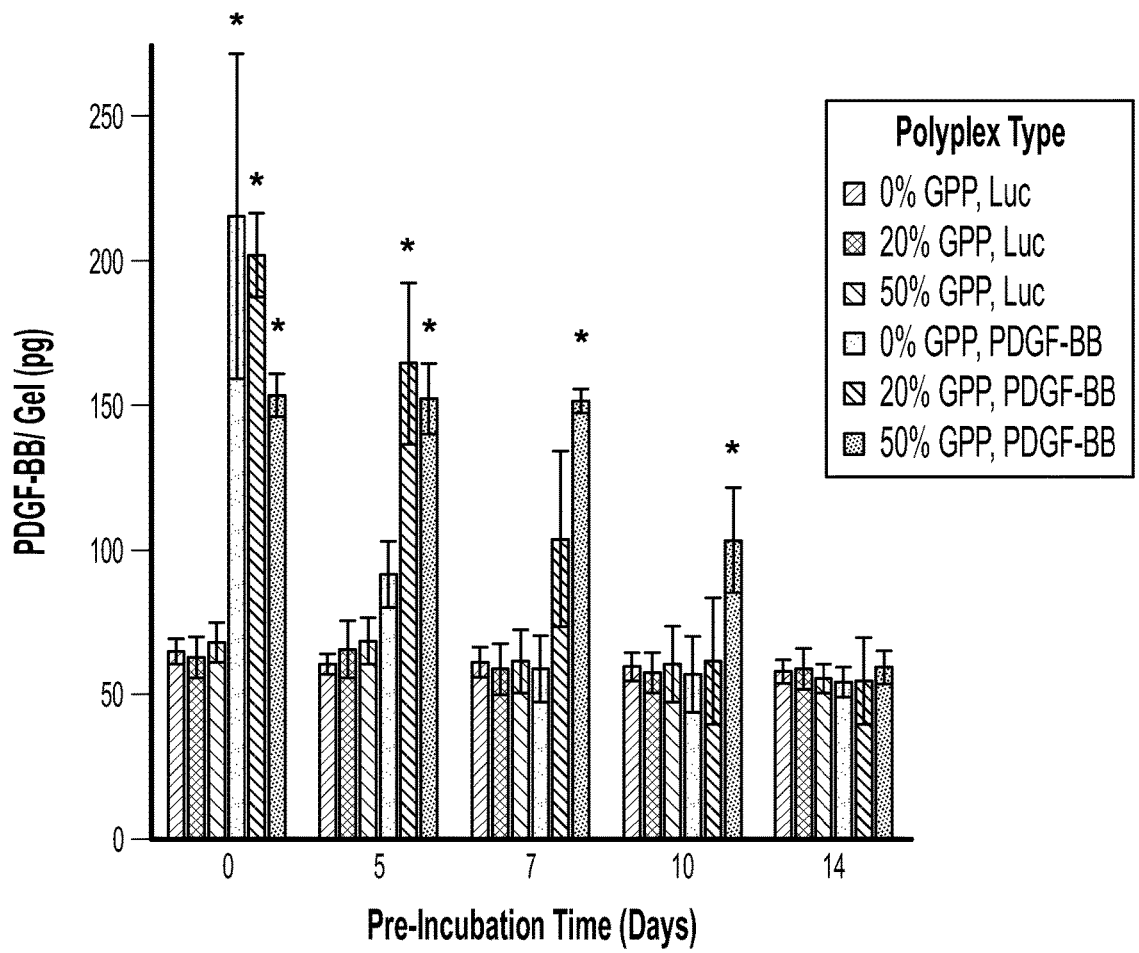
FIG. 2 shows cellular expression of PDGF-BB that was analyzed 4 days after NIH/3T3 cells were plated onto collagen gels containing polyplexes as assessed by ELISA. The data represent the mean±standard deviation (SD) in four separately prepared and analyzed samples. * denotes a statistically-significant difference ($p<0.05$) relative to the luciferase-encoding controls.

To quantify cell-expressed PDGF-BB in the modified-collagens, both direct and indirect sandwich ELISA assays were used. No significant differences in the PDGF-BB concentrations were detected in conditioned media collected from any of the samples, based upon sandwich ELISA measurements; however, significant differences between samples were detected when the levels of collagen-bound PDGF-BB were analyzed by release from collagen via extraction buffer and direct ELISA (FIG. 2). In particular, when samples were not preincubated, collagen-bound PDGF-BB levels were elevated in all samples containing polyplex encoding for PDGF-B relative to samples containing polyplex encoding for luciferase. In the non-preincubated samples, the highest levels of expression were observed in the PDGF-B-encoding samples with unmodified and 20% GPP-PEI/total PEI polyplex, which exhibited over a 4-fold increase in expression relative to the luciferase controls. Levels of expression in the 50% GPP-PEI/total PEI PDGF-BB sample were also elevated in these samples, with a nearly 3-fold increase in expression. In the unmodified polyplex samples, the level of expression rapidly decreased when the gels were exposed to wound-mimetic conditions, through preincubation of the gels with serum solutions at 37° C. PDGF-BB expression decreased by more than 60% after a 5-day serum preincubation in the unmodified polyplex samples, and at this time point, the expression levels ceased to be higher than those overserved in the luciferase controls. Expression in the GPP-modified samples also decreased as a function of preincubation time; however, the rate of decrease was substantially slower. After a 5-day preincubation, expression decreased in the 20% GPP-PEI/total PEI samples by only 20%, and the expression levels decreased 55% after a 7-day preincubation, relative to the non-preincubated samples. PDGF-BB expression in the 20% GPP-PEI/total PEI samples ceased to be greater than the luciferase-encoding control samples after preincubation periods over 7 days. The 50% GPP-PEI/total PEI samples exhibited an increased longevity in gene transfer activity when exposed to physiologically-simulating conditions. These samples maintained consistent levels of expression that were approximately 3-fold greater than the luciferase-encoding controls for up to a 7-day preincubation period. The samples exhibited significantly elevated levels of PDGF-BB relative to the controls for up to a 10-day preincubation.

Quantification of PDGF-BB-Mediated Cellular Proliferation

Figure 3:
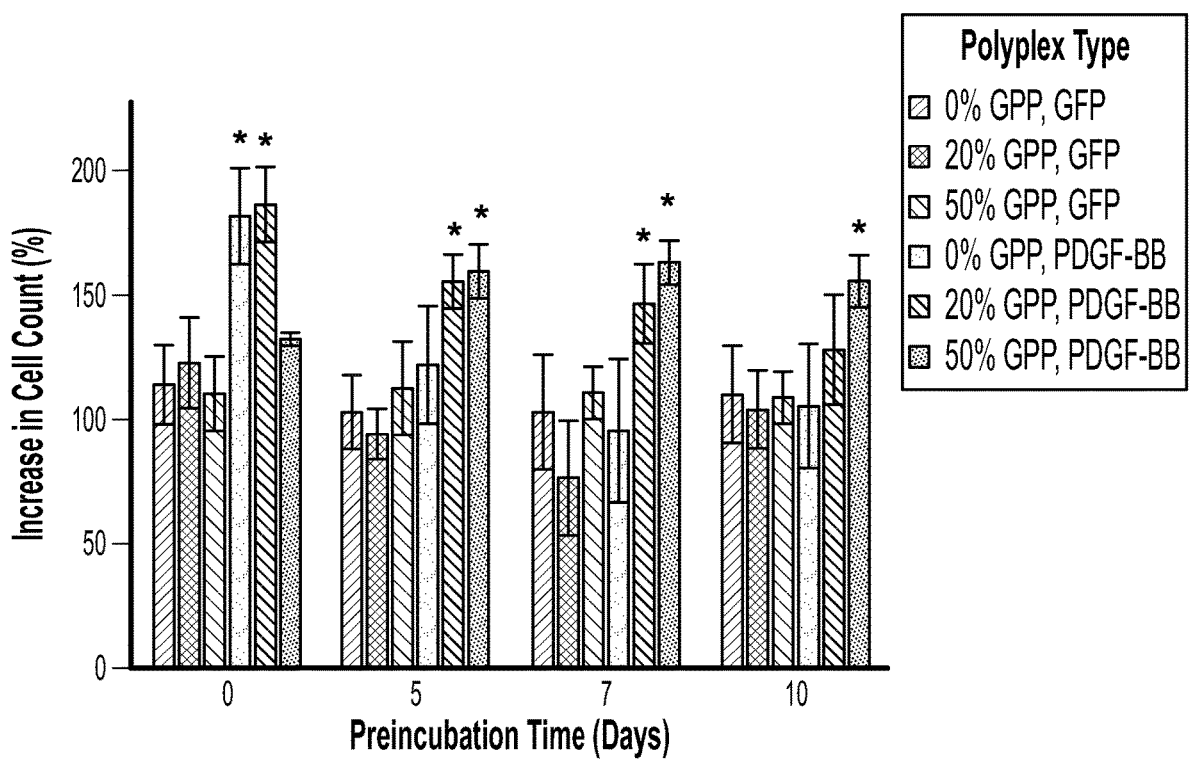
FIG. 3 shows cellular proliferation in preincubated collagen gels containing polyplexes, 4 days after NIH/3T3 cells were seeded onto the gels. Proliferation was analyzed to determine the mitogenic activity of cell-expressed PDGF-BB. The data represent the mean±SD of the increase in cell count, relative to the number of cells initially seeded, as assessed with a hemocytometer after cell recovery from the gels, in four separately prepared and analyzed samples. * denotes a statistically-significant difference ($p<0.05$) relative to the GFP-encoding controls.

To assess if cell-mediated PDGF-BB expression impacted cellular behavior after prolonged pre-incubation, cell proliferation was quantified via cell recovery from the modified collagen gels after 4 days of culture. Samples were analyzed at 4 days to exclude the effect of cellular confluency on cell behavior while determining the maximum period over which polyplex activity could be preserved in the presence of physiologically-simulating conditions. As shown in FIG. 3, the non-preincubated unmodified polyplex samples and 20% GPP-PEI/total PEI samples encoding PDGF-B exhibited elevated cell counts that were approximately 65% greater than the levels observed in the controls. After preincubation under physiologically-simulating conditions for 5 days or longer, no significant difference in cell count was found in the unmodified polyplex samples, whereas cellular proliferation in the 20% GPP-PEI/total PEI samples remained significantly elevated relative to the controls for up to a 7-day preincubation. Proliferation in the 50% GPP-PEI/total PEI samples remained elevated relative to controls for the longest period, with a significant increase of about 50% in cell counts even after a 10-day preincubation. Additionally, the cell counts recorded in the 20% GPP-PEI/total PEI were approximately 56% greater than those in the 50% GPP-PEI/total PEI when the gels were not preincubated, but the count levels between the 20% and 50% samples were determined to be statically indistinguishable after either a 5-day or a 7-day preincubation. After a 10-day preincubation, proliferation in the 50% GPP-PEI/total PEI samples surpassed that recorded in the 20% GPP-PEI/total PEI samples by approximately 23%. The cell counts recorded in the 50% GPP-PEI/total PEI samples preincubated for 5, 7, or 10 days were statistically indistinguishable from one another. 14-day preincubation studies were also conducted, however the results were not included because the samples exhibited no statistical difference from the controls and thus did not add any substantive information to the figure.

Quantification of PDGF-BB-Mediated ECM Remodeling

Figure 4:
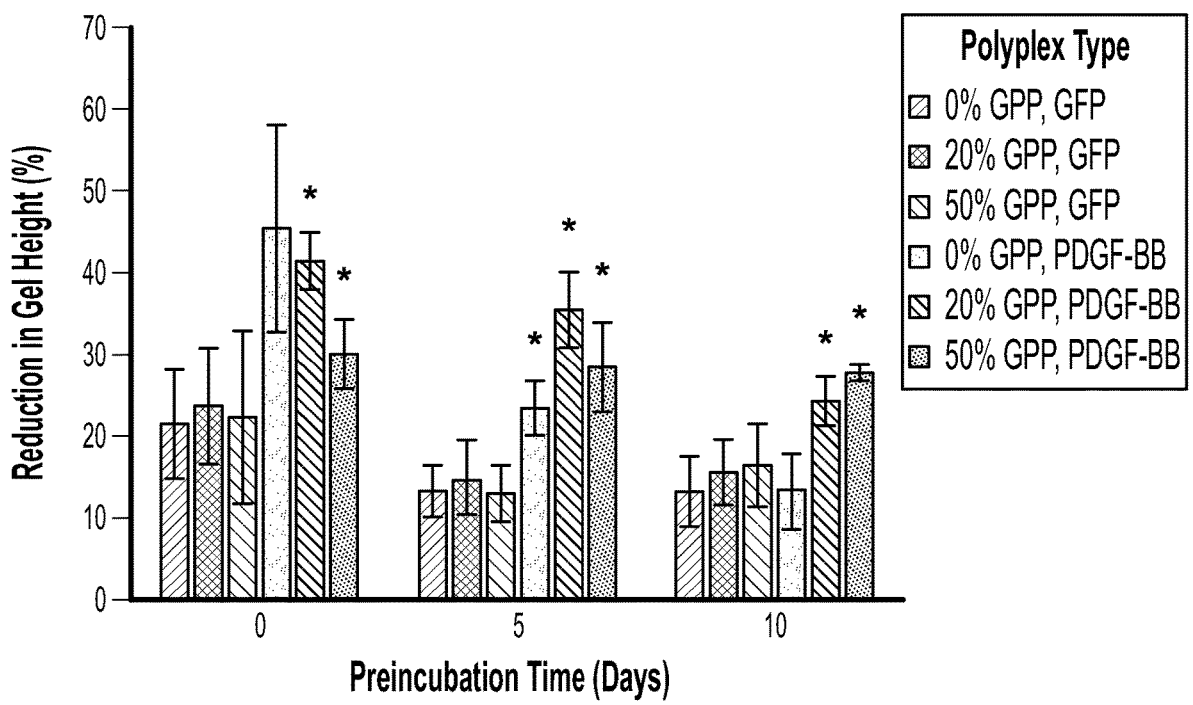
FIG. 4 shows collagen remodeling in the preincubated polyplex-containing collagen gels in response to cell-mediated expression of PDGF-BB. Remodeling was monitored by measurement of the reduction in gel height (z), relative to the initial height in each gel, using ImageJ to assess gel images, 3 days after NIH/3T3 cells were seeded onto the gels. The data represent the mean±SD of five separately prepared and analyzed samples. * denotes a statistically-significant difference ($p<0.05$) relative to the GFP-encoding controls.

A contraction assay was used to assess the level of ECM remodeling in response to cell-mediated PDGF-BB expression. As shown in FIG. 4, gel heights shrank due to contraction at a significantly greater rate in all samples containing polyplex encoding for PDGF-B. Reflecting the PBGF-BB quantification and PDGF-BB-mediated proliferation results, the non-preincubated unmodified polyplex samples and 20% GPP-PEI/total PEI samples exhibited the greatest reductions in gel height, decreasing approximately 20% more relative to the controls. After pre-incubating the samples, no significant differences in gel height were observed in the controls vs. the unmodified polyplex samples. However, the reduction in gel height remained significant in the 20% and 50% GPP-PEI/total PEI samples for up to a 10-day preincubation. Contraction was greatest in the 20% GPP-PEI/total PEI sample when the sample was not preincubated, and contraction levels in this sample were indistinguishable after preincubation for 5 vs. 10 days.

PDGF-B-Triggered Migration in Layered Collagen Gels

Figure 5:
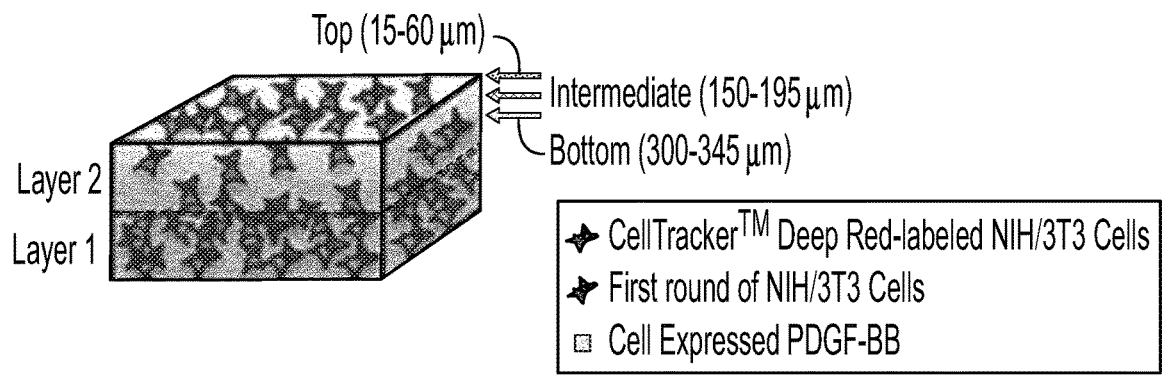
FIG. 5 shows cell migration in a collagen bi-layer model in response to cell-expressed PDGF-BB. Cell migration was tracked using microscopy. The initial collagen layer (bottom layer; layer 1) was preincubated for 3 (a, b) or 10 (c, d) days before the addition of the next layer (layer 2). The data represent the mean±SD in cell counts (left) and cell counts that were normalized by the total number of analyzed cells per gel (right) of four separately prepared and analyzed samples. Cells were allowed to migrate for 48 hours prior to analysis.
Figure 5:
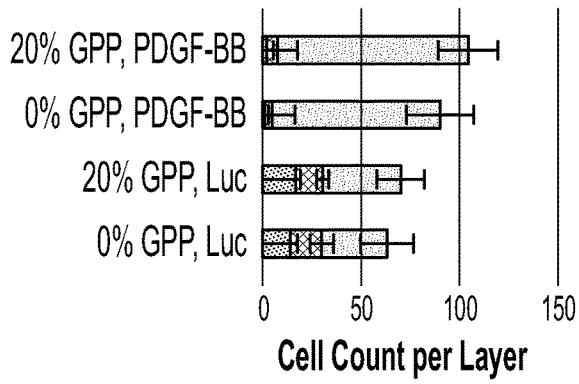
Figure 5:
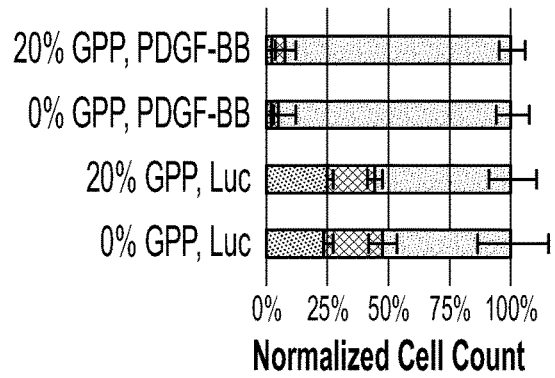
Figure 5:
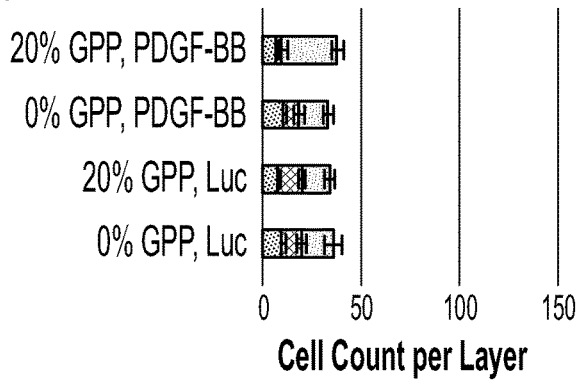
Figure 5:
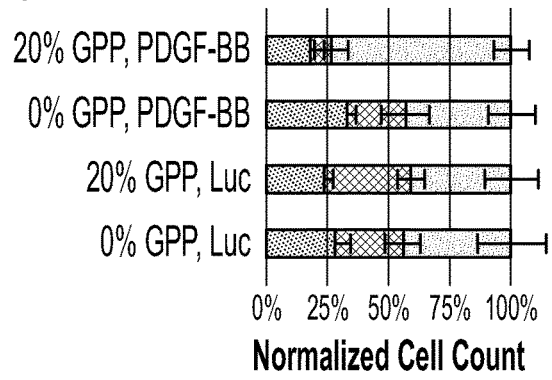

To determine if cell-mediated PDGF-BB expression triggered chemotaxis, layered collagen gels were constructed. The first layer (layer 1) contained polyplex encoding for PDGF-B (or luciferase, as a control), and cellular ingrowth and gene transfection were allowed to occur within this layer for a period of 2 d. Subsequently, a second collagen layer (layer 2) was added, and additional cells containing a tracking dye were plated atop this fresh collagen (FIG. 5a). The labeled cells in the second layer were allowed to migrate in response to PDGF-BB expressed by cells in the first layer, and the extent of cell migration towards the bottom layer was quantified via fluorescence microscopy. As shown in FIG. 5, the length of time the first layer was preincubated directly impacted cellular migration. Specifically, in samples in which the first layer was preincubated for 3 d, all samples containing the PDGF-B-encoding polyplex exhibited accelerated migration as compared to controls in which luciferase-encoding polyplexes were used. In these samples, about 90% of the analyzed cells migrated 300 μm towards the bottom layer when the first layer contained PDGF-B-encoding polyplexes, whereas only ~50% of the cells migrated as far with the luciferase-encoding polyplexes. When the first layer gel was preincubated for a 10-day period, approximately 44% of cells migrated to the bottom level in both the luciferase-encoding polyplex samples and the unmodified polyplex samples, whereas almost 75% of the analyzed cells had migrated to the bottom layer in the 20% GPP-PEI/total PEI PDGF-B-encoding samples. A significantly greater amount of cells were also observed in the intermediate level of the gel in the unmodified polyplex samples relative to the GPP-modified samples.

In Vitro Wound Model

Figure 6:
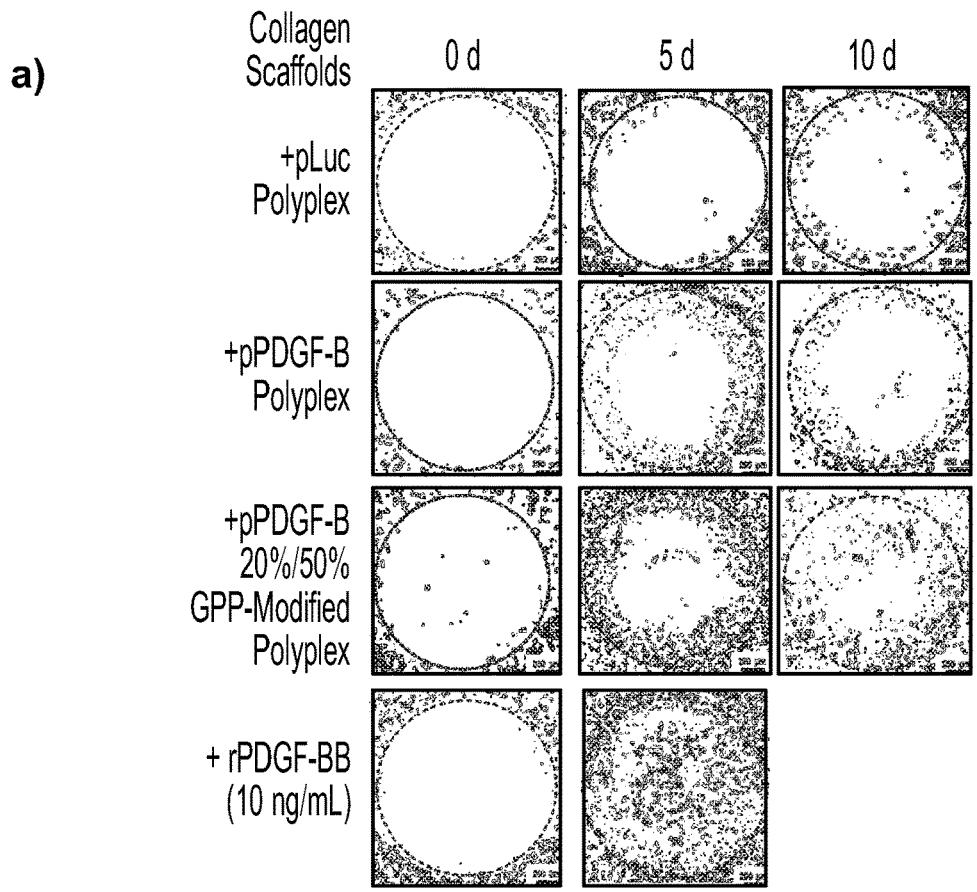
FIG. 6 shows an in vitro wound model. Defects in cell-seeded collagen gels were filled with collagen scaffolds modified with rPDGF-BB, polyplex encoding for luciferase, or polyplex encoding for PDGF-BB, and subsequent defect invasion or "wound closure" was monitored via microcopy. Representative images (a) were analyzed via ImageJ to quantify wound closure (b). The data represent the mean±SD of three separately prepared and analyzed samples. * denotes a statistically-significant difference ($p<0.05$) relative to the luciferase-encoding controls.
Figure 6:
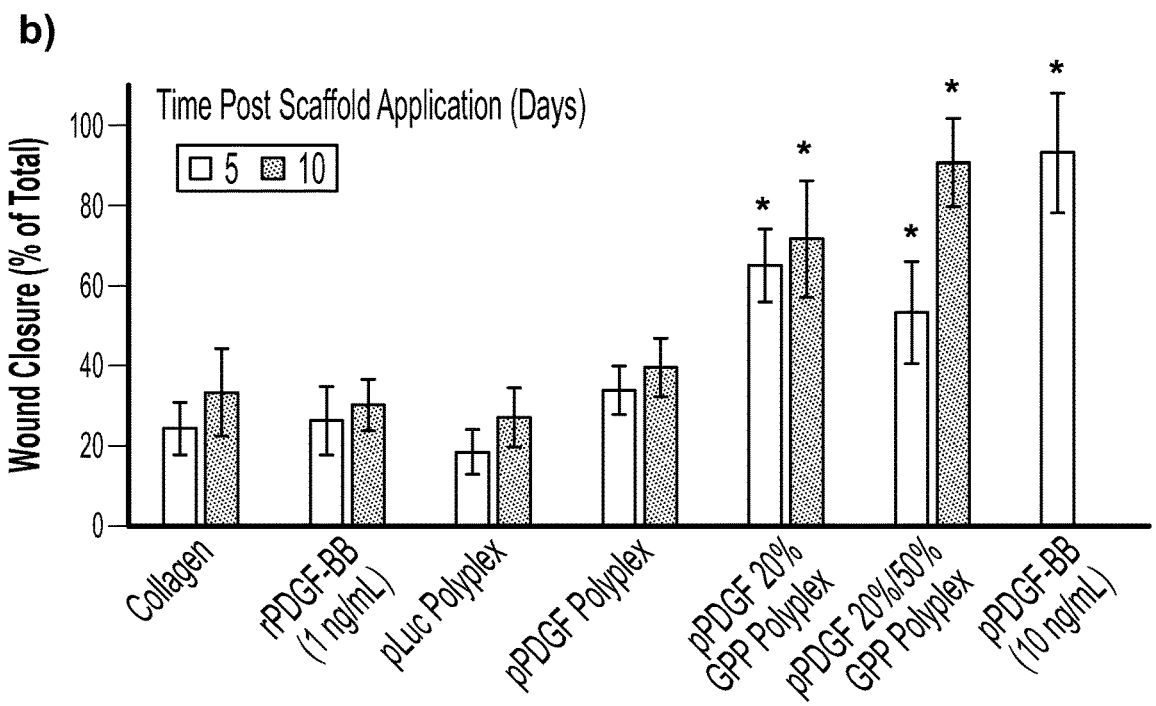

To culminate the studies, the ability to achieve enhanced wound closure via cellular responses triggered by cell-expressed PDGF-BB was examined in an in vitro wound model (FIG. 6). Cellular invasion of uniform wounds created in collagen after application of DNA-modified collagen scaffolds or collagen embedded with rPDGF-BB was monitored via calcein AM staining. In the samples in which a scaffold containing polyplex encoding PDGF-B was administered, accelerated cellular invasion was noted, particularly in the GPP-modified samples. Specifically, the wound closure in the unmodified sample encoding for PDGF-B was only statistically different from closure in the luciferase-encoding polyplex control, whereas it was not statistically distinguishable from pure collagen or low rPDGF-BB-containing controls (1 ng/mL PDGF-BB). After 5 days, the 20% and 20%/50% GPP-modified samples achieved similar levels of wound closure (approximately 65% and 53%, respectively), but these samples did not achieve the same levels of closure as the high rPDGF-BB dosage control (10 ng/mL PDGF-BB). After an additional 5 days (10 days post-defect), a significant increase in percentage of wound closure was only recorded in the GPP-modified samples, with the 20%/50% GPP-modified sample achieving the same level of wound closure as the high dosage rPDGF-BB control. Studies with 50% GPP-modified samples were also initiated, but these samples were terminated early due to the low levels of observed wound closure within the monitoring period. Additionally, a similar in vitro wound defect model employing pre-labeled cells was used to assess wound closure at early time points, and these experimental demonstrated that wound closure did not occur in any samples during the initial 3 days.

Discussion

The inherent complexity and hostility of the chronic wound environment has greatly complicated treatment, causing the failure of most monotherapies containing just GFs or biomaterial-based scaffolds. Chronic wounds exhibit a self-sustaining, hyper-inflammatory response in which excessive protease activation impairs cellular infiltration and causes the rapid degradation of GFs and other molecules essential for the reparative process. The addition of GF through topical or sustained applications has been shown to enhance repair in several human studies, demonstrating its potential for modifying the wound environment; however, the modest degree of clinical success with these approaches underscores significant deficiencies in the way GFs are presented. GF therapies are reliant on repetitive, extraphysiological doses, increasing the likelihood of off-target effects and oncogenic responses. GF gene therapies, particularly when delivered via a biomaterial, exhibit benefits in protein stability, protein bioactivity, sustained release, and cost. The potential to deliver multiple genes with relative ease and the spatiotemporal control achievable though promoter choice/vector design are also extremely advantageous. Moreover, gene delivery better mimics endogenous repair, allowing host cells to orchestrate GF production, microlocalization, and activity, which are particularly crucial in mitigating the pathophysiology of a chronic wound.

In our work, we have shown that CMP-mediated gene delivery has compelling and unanticipated advantages for overcoming the obstacles that have prevented the translation of genetic therapeutics in wound repair. CMP-based gene transfer reduces the dangers of therapeutic escape and abrogates concerns of low activity in protein/serum-rich environments. In particular, we demonstrated previously that GPP-modification of PEI polyplexes greatly enhanced control over both the extent and duration of transgene expression through utilization of the reversible, serum-stable affinity between CMPs and collagen films. Enhanced control and activity were demonstrated both in vitro (Urello et al., Journal of Materials Chemistry B. 2014; 2(46):8174-8185) and in vivo, using a murine subdermal repair model (see Example 2). Additional studies concluded that these improvements were the result of superior serum stability and endocytic trafficking driven by increases in polyplex affinity for collagen and the natural process of collagen remodeling. While other reports have utilized collagen remodeling/proteolytic sensitivity to achieve cell-triggered release, CMP modification provided a tool for direct integration of both release and endocytic uptake with collagen remodeling, while providing enhanced serum stability.

Having demonstrated the ability to integrate gene delivery with collagen remodeling, our objective in this work was to incorporate our DNA/collagen system into a wound environment and demonstrate its benefits for promoting key wound repair activities. Cell invasion, proliferation, and ECM remodeling are prerequisites for both wound healing and the initiation of gene transfer activity from the GAMs, and therefore PDGF-B, which is capable of stimulating these cellular responses, was a natural target. Through modification with a CMP containing an established, GPP-rich sequence, we were able to identify significant improvements in both PDGF-BB expression and activity. GPP modification substantially expanded the length of time the DNA/collagen gels could be exposed to physiological-simulating conditions (37° C. in serum-supplemented media), from 0 days to 10 days, and still observe enhanced PDGF-BB expression. While MMP concentrations are elevated in the wound environment, no MMPs or wound-relevant proteases were added during the pre-treatment step, based on studies showing localization of MMPs in the cellular microenvironment at the wound edge or immediate tissues. Utilizing preincubation to simulate the environment of an applied collagen-based dressing before cell invasion, this study suggests that GPP modification can be used to prolong the activity of DNA polyplexes during the process of cellular invasion, which often occurs over a period of weeks to months in chronic wounds. Varying the display of GPP on the polyplex from 20% GPP-PEI/total PEI to 50% GPP-PEI/total PEI expanded the period the gels could be exposed to physiological-simulating conditions from 5 days to 10 days, suggesting that GPP display could also be used to tailor the extent and period of PDGF-BB expression as required. Additional studies have also shown varying CMP sequence allows for further tailoring of retention/release, suggesting additional tuning could be achieved with relative ease. For example, it was demonstrated that lengthening the CMP sequence (GPO$_7$ vs. GPO$_{10}$) could be used to decrease the CMP-collagen initial dissociation index (IDI) by 1.7-fold and expand retention/release of a GPP-modified polymer from approximately 7 days to over 12 days.

Our studies also highlighted the benefits of GF gene vs. GF protein delivery, and demonstrated in particular the mechanisms by which GPP-modification of gene vectors amplifies these benefits. For instance, we demonstrated the ability to trigger cellular responses similar to those observed in rPDGF-BB/collagen systems, yet with 3 orders-of-magnitude lower levels of local PDGF-BB expression than the levels of rPDGF-BB delivered in GF-collagen therapies. DNA/collagen gels containing PDGF-B-encoding polyplex were able to trigger cellular behaviors not observed in controls with luciferase encoding polyplex. Cell proliferation was increased by up to 65%, gel contraction was increased by as much as 2-fold, and cell migration was triggered via cell-produced PDGF-BB gradients. When PDGF-B-encoding polyplexes were used in collagen bi-layer migration studies, as many as 90% of cells had migrated 300 μm into the gel within 48 h post cell seeding. Furthermore, cells were visible at this level (300 μm-345 μm) within 24 h post cell seeding, and given that the typical speed of NIH/3T3 cell migration in collagen is less than one cell diameter per hour, the determined speed of these cells (12.5 μm/h) indicates both the directionality and consistency of their migration. Our findings accentuate the importance of cell-mediated expression and micro-localization encouraged by efficient gene delivery, and show how gene delivery can be used to overcome the high costs and safety concerns associated with high doses of GFs. Consistent with the enhanced levels of PDGF-BB detected in samples containing GPP-modified, PDGF-expressing polyplex, GPP-modification was found to stabilize the systems even after prolonged periods of preincubation. For example, increases in proliferation were observed after a 10-day preincubation, whereas no increases were observed in any of the unmodified samples preincubated for this length of time. Collagen remodeling and chemotaxis were also enhanced for up to a 10-day preincubation in GPP-modified samples, vs. only a 5-day preincubation in unmodified samples. The extent of GPP-modification was also found to expand other observable cellular responses, underscoring the flexibility CMP modification provides. For example, cell counts in 20% GPP-PEI/total PEI samples were increased by up to 65% relative to luciferase controls, and these levels remained statistically greater than the controls for up to a 7-day preincubation. Alternatively, cell counts in the 50% GPP-PEI/total PEI samples preincubated for 5 or 7 days were consistently about 50% greater than those in the luciferase controls, and these counts were statistically indistinguishable from those recorded in the 20% GPP-PEI/total PEI samples. Cell counts remained significantly enhanced for up to a 10-day preincubation in the 50% GPP-PEI/total PEI samples. The fact that increased proliferation was not observed for the same times periods over which enhanced chemotaxis and remodeling were observed is consistent with the finding that higher concentrations (>5 ng/mL) are required to promoted mitosis, whereas lower concentrations (<1 ng/mL) are sufficient for migration.

The benefits of GPP-mediated PDGF-BB gene delivery also translated in a 3-D wound model where wound closure was defined as the point when the average cell density in the defect matched the average cell density in the area surrounding the defect. Collagen-based scaffolds containing PDGF-B-encoding polyplex promoted increased invasion and elevated cell densities within the defects within 3 days (unpublished data). Mirroring the results observed in the preincubation studies, GPP-modification appeared to preserve the activity of the scaffolds in environments containing nucleases and serum proteins at physiological temperatures. Scaffolds with the 20% GPP-modified polyplex had wound closure rates 2.3-fold and 1.6-fold faster than those observed in the empty collagen scaffolds and in the scaffolds containing unmodified PDGF-B-encoding polyplex, respectively, over a 5-day closure period. By day 10, wounds containing the 20% GPP-modified polyplex scaffolds had induced nearly a 2.1-fold and 2-fold increase in wound closure compared to wounds in which empty collagen and unmodified polyplex scaffolds were applied. The relative rate of closure was comparable to that achieved using in other in vitro wound models as well as in vivo models of soft tissue wounds. For example, the application of PDGF-B encoded by plasmid or adenovirus DNA vector embedded in collagen matrix induced a 2.5-fold increase in wound closure in 6-mm or 8-mm ischemic skin wounds in rabbits, relative to a negative control. To achieve the same effect in our wound model with PDGF-BB, an order of magnitude increase in rPDGF-BB exposure was required. The greater dosage not only necessitates greater treatment costs, but also increases the danger of off-target responses, as PDGF-BB leakage from collagen-gels and sponges is a major problem in protein-based delivery. Moreover, when rPDGF-BB was applied in the wound model at the same concentration as that expressed in the GPP-modified collagens (1 ng/mL), wound closure was indistinguishable from the empty collagen control, further supporting the fact that efficient gene delivery allowed dramatically reduced dosages. The identical levels of overall wound closure via gene delivery were achieved in this model through application of an 8:2 (m/m of DNA in the 20% vs. 50% GPP-modified polyplex) mixture of 20%/50% GPP-PEI/total PEI polyplex. Five days after application, the percent of wound closure was identical to that in the 20% GPP-PEI/total PEI sample, but while the 20% sample plateaued at approximately 75% wound closure, the combined polyplex sample achieved over 90% wound closure, the same as the high dosage rPDGF-BB control. These results highlight the versatility of CMP modification, where both CMP sequence and display can be used to tailor not only release, but also the extent and duration of GF expression. While these outcomes have been demonstrated here in a simplified wound model, the results support the potential utility of localized gene delivery over protein delivery in the more general context.

Conclusion

GF gene therapies may have the potential to overcome the innate incompatibility many current GF therapies have with the wound bed, through promoting on-demand GF production that better mimics endogenous repair responses by allowing host cells to orchestrate sustained GF expression, microlocalization, and activity. CMP modification of DNA carriers, particularly PEI polyplexes, has been demonstrated by our labs and shown to enable the hijacking of not only the cellular machinery needed to express GFs (or any gene of interest), but also the cellular mechanisms inherent in the natural process of collagen remodeling to achieve cell-triggered delivery and enhanced endocytic uptake. In this work, GPP-modification was shown to enhance expression of functional GF (PDGF-BB) and trigger essential cell behaviors associated with wound repair. Furthermore, CMP-mediated gene delivery achieved similar levels of wound closure as the levels reached when an order of magnitude more rPDGF-BB was applied. The fact that a combination of 20% and 50% GPP-PEI/total PEI polyplexes could be used to tailor this response highlights the versatility of this approach, and identifies additional tuning factors which have yet to be fully explored. Both the tunablity of this method and its ability to hijack collagen remodeling, a process that already occurs in excess in wounds, make this an ideal method for achieving efficient GF delivery in the wound bed.

Example 2. ECM Turnover-Stimulated Gene Delivery Through Collagen-Mimetic Peptide-Plasmid Integration in Collagen Gene therapies have great potential in regenerative medicine; however, clinical translation has been inhibited by low stability and limited transfection efficiencies. Herein, we incorporate collagen-mimetic peptide (CMP)-linked polyplexes in collagen scaffolds to increase DNA stability by up to 400% and enable tailorable in vivo transgene expression at 100-fold higher levels and 10-fold longer time periods. These improvements were directly linked to a sustained interaction between collagen and polyplexes that persisted during cellular remodeling, polyplex uptake, and intracellular trafficking. Specifically, incorporation of CMPs into polyethylenimine (PEI) polyplexes preserved serum-exposed polyplex-collagen activity over a period of 14 days, with 4 orders-of-magnitude more intact DNA present in CMP-modified polyplex-collagen relative to unmodified polyplex-collagen after a 10 day incubation under cell culture conditions. CMP modification also altered endocytic uptake, as indicated by gene silencing studies showing a nearly 50% decrease in transgene expression in response to caveolin-1 silencing in modified samples versus only 30% in unmodified samples. Furthermore, cellular internalization studies demonstrated that polyplex-collagen association persisted within cells in CMP polyplexes, but not in unmodified polyplexes, suggesting that CMP linkage to collagen regulates intracellular transport. Moreover, experiments in an in vivo repair model showed that CMP modification enabled tailoring of transgene expression from 4 to 25 days over a range of concentrations. Overall, these findings demonstrate that CMP decoration provides substantial improvements in gene retention, altered release kinetics, improved serum stability, and improved gene activity in vivo. This versatile technique has great potential for multiple applications in regenerative medicine.

Introduction

Regenerative medicine has the potential to restore function to damaged tissues or organs, and its promise has prompted the development of a wide range of biomaterials and drug delivery approaches. To guide complicated remodeling and repair processes, biomaterial-based scaffolds are commonly employed to provide a framework for cellular growth and tissue deposition. While traditional scaffolds have been engineered with emphasis on providing biocompatible, structural support, focus in recent years has shifted towards materials designs with the capacity to guide more complex aspects of reparative processes. To serve as good analogues of the extracellular matrix (ECM), scaffolds should act as cell-responsive structures capable of dynamically interacting with cells during cellular ingrowth, proliferation, and phenotypic commitment. For this purpose, the stable incorporation and controllable delivery of bioactive cues, such as therapeutic proteins or DNA, are essential.

The ECM serves as a natural reservoir for bioactive cues such as growth factors (GFs), whose release and activity are controlled by both ECM affinity and ECM turnover. ECM turnover is a tightly-regulated process that consists of two primary steps: protease-mediated ECM degradation and endocytic uptake of the resulting ECM fragments. The ECM undergoes continuous remodeling; however turnover rates are elevated during development and regeneration, and can also occur in response to signals transmitted from ECM receptors or ECM-modifying proteins such as matrix metalloproteinases (MMPs). In turn, cell-triggered, localized delivery of ECM-bound cues (e.g., GFs), with tightly regulated and distinct release kinetics, is achieved in direct coordination with other reparative processes. Similar mechanisms that exploit ECM remodeling have evolved to enable entry of other moieties and signals into cells with high efficiency. Viruses bind to ECM to enhance their cellular availability, preserve their stability, and increase the chance of internalization via interaction with specific cellular receptors, and ECM endocytic pathways are also commonly used to facilitate cellular uptake of viruses via integrin-dependent pathways, especially via collagen-binding integrins such as $\alpha_2\beta_1$. ECM components have even been found to act as bridges that directly facilitate binding and initiate viral internalization.

The ability to harness ECM turnover would also have key benefits for synthetic materials engineered to control therapeutic delivery. Enzymatically degradable polymer matrices of both synthetic and natural origin have been designed to confer proteolytic sensitivity such that tissue remodeling and scaffold degradation are synchronized, and these approaches have been shown to dramatically improve therapeutic stability and activity. For instance, matrix metalloproteinase (MMP) degradable polymers and tethers have been used to coordinate the delivery of stabilized GFs such as vascular endothelial growth factor (VEGF) and bone morphogenetic protein 2 (BMP-2) with cellular remodeling during diabetic ulcer healing and bone regeneration, respectively. Additionally, scaffolds have also been designed to achieve improved, localized gene delivery and thereby provide a compelling alternative for creating GF-rich environments; gene manipulations are less expensive, more stable, and have a proven capacity to elicit improved therapeutic effects with orders of magnitude (~2000-fold) dose reductions compared to those necessary for topical administration of GFs. Furthermore, gene delivery mimics endogenous repair, using host cells to coordinate localized, sustained GF production and in situ, on-demand delivery of nascent proteins with authentic post-translational modifications. These characteristics are of particular value in tissues such as chronic wounds due to their extended healing over months and spatiotemporal heterogeneity. For instance, in vivo studies have demonstrated that incorporation of GF-encoding DNA into both polymer-based and protein-based scaffolds can promote transgene expression over periods ranging from days to weeks, leading to essential reparative processes where no healing or minimal healing was previously observed.

Despite the potential benefits of scaffold-mediated gene transfer, existing materials have been unable to provide sufficient healing activity due to their lack of sufficient in vivo stability and prolonged delivery. Improved delivery strategies thus are vital for clinical translation. Currently, DNA is most commonly incorporated into polymer-based scaffolds (i.e., polyplexes) and protein-based scaffolds through either simple encapsulation approaches or adsorption methods employing non-covalent interactions between the substrate and the DNA or DNA carrier (e.g., electrostatic, hydrophobic, or van der Waals interactions). Such methods offer simplicity and have the capacity, as noted above, to achieve cell-triggered release through use of protease-degradable materials. However, existing methods for incorporating DNA within biomaterials often fail to retain gene carriers in the delivery site for prolonged periods in vivo and off-target delivery is problematic. For instance, collagen scaffolds containing electrostatically entrapped, PDGF-B-encoding adenovirus accelerated healing in experimental rat wound models, yet vector escape and immunogenicity were apparent and hindered clinical translation. While the use of non-viral gene delivery can potentially minimize immunogenicity concerns, non-viral approaches often fail to induce complete repair in preclinical models, and insufficient gene transfer efficacy has been identified as the major limiting factor. Furthermore, most existing technologies for sustained therapeutic delivery are not suitable for many tissue repair applications because of the complexity of the healing process, which can include extended healing periods over months and multiple out-of-phase healing cascades within repair sites. A reliable strategy to retain active gene carriers until cells initiate repair and facilitate efficient gene transfer is essential.

In this work, our goal was to demonstrate that the anchoring of polyplexes via specific interactions with collagen could be used to achieve stable gene expression in vivo by harnessing collagen turnover as a driver for not only gene release, but also enhanced activity. Our studies employ collagen-mimetic peptides (CMPs), which comprise primarily a collagen-like $(GXY)_n$ motif and have the unique capacity to stably integrate within native collagen through a reversible strand-exchange process. Our prior work was the first to demonstrate that CMP-based integration of polyplexes could be used to retain stabilized DNA on collagen with improved control over the timing and extent of gene delivery for periods of a week to over a month (2-fold longer than that of unmodified polyplexes), and the direct correlation of transgene expression with MMP concentrations. In this work, we evaluated the persistence of the collagen-polyplex interaction and the capacity to drive gene delivery via endocytic collagen turnover. CMP-modified PEI polyplexes were incorporated into collagen gels and long-term transfection studies and DNA integrity assays were employed to monitor polyplex efficacy and stability. Collagen-polyplex co-internalization studies and gene silencing experiments were used to assess mechanisms of cellular uptake, particularly via caveolar mechanisms. Additionally, extended studies in murine models were used to determine the feasibility of CMP-based mechanisms for improving gene transfer in vivo, and its potential application in regenerative medicine.

Materials and Methods

Materials

Fmoc-protected amino acids were purchased from Anaspec (Fremont, CA). H-Rink amide CHEMMATRIX resin was purchased from PCAS Biomatrix (Quebec, Canada). O-Benzotriazole-N,N,N',N'-tetramethyl-uronium-hexafluoro-phosphate (HBTU) was purchased from Novabiochem (San Diego, CA). High performance liquid chromatography (HPLC)-grade N,N-dimethyl formamide (DMF), acetonitrile, trifluoroacetic acid (TFA), LIPOFECTAMINE RNAiMAX Reagent, and cell culture reagents, including Dulbecco's modified Eagle's medium (DMEM), Opti-MEM I Reduced Serum Media (Opti-MEM), Dulbecco's phosphate buffered saline (PBS), and trypsin were purchased from Fisher Scientific (Fairlawn, NJ). Fetal bovine serum (FBS) was purchased from Corning (Manassas, MA). Piperidine, 4-methylmorpholine, all cleavage cocktail components, branched PEI (25 kDa), collagen type I-fluorescein isothiocyanate (FITC), and syringes were purchased from Sigma-Aldrich (St. Louis, MO). Type I bovine collagen was purchased from Advanced BioMatrix (San Diego, CA). DNA gel loading dye and Alexa Fluor 350 NHS ester were purchased from Thermo Fisher Scientific (Waltham, MA). pCMV-GLuc plasmid was purchased from New England Biolabs (Ipswich, MA) and pCMV-MetLuc-mem plasmid was purchased from Clontech (Mountain View, CA), and both plasmids were amplified in NEB 5-α electrocompetent E. coli purchased from New England Biolabs. The plasmids were purified from bacterial culture using a Qiagen Megaprep Kit (Valencia, CA), following the manufacturer's protocols. Caveolin-1 siRNA and caveolin-1 Antibody (N-20) was purchased from Santa Cruz Biotechnology (Dallas, Texas) and Goat Anti-Rabbit IgG (Horseradish Peroxidase (HRP)) was purchased from Abcam (Cambridge, MA). Collagenase I was purchased from Worthington Biochemical Corp (Lakewoord, NJ). Growth factor reduced (GFR) phenol red free MATRIGEL was purchased from Corning (Corning, NY), BMP-2 was purchased from GenScript (Piscataway, NJ), and coelenterazine was purchased from Clontech and GoldBio (Yorba Linda, CA).

Preparation of Modified Collagen Gels

The GPP-based CMP [GPP: $(GPP)_3$GPRGEKGERGPR $(GPP)_3$GPCCG] GPP (SEQ ID NO: 3) was synthesized via Fmoc solid phase peptide synthesis, conjugated to PEI using Michael-type addition chemistry, and subsequently, the GPP-PEI was used to prepare GPP-modified polyplexes as described by Urello et al. (Journal of Materials Chemistry B 2(46) (2014) 8174-8185). Using a variation of well-established polyplex formation protocols (Larsen et al., Molecular Pharmaceutics 9(5) (2012) 1041-1051; Reilly et al., Molecular Therapy 19(7) (2011) 1388-1389), equivolumetric solutions of PEI and DNA suspended in 20 mM HEPES buffer (pH 6.0) were combined to yield a final solution with an amine to phosphate ratio (N:P) ratio of 10. To incorporate the GPP, a specified percent of PEI was replaced with the GPP-PEI conjugate after preincubation at 50° C. for 30 minutes to prevent triple-helical hybridization of the GPP. Collagen gels with GPP-immobilized or encapsulated unmodified polyplexes were constructed by re-suspending dehydrated polyplex in neutralized type I bovine collagen-solution (4 mg/mL, pH 7.4) as described by Urello et al. (Journal of Materials Chemistry B 2(46) (2014) 8174-8185). 250 µL of this solution was added to each well of an 8-well plate (0.8 cm$^2$ surface area/well) and incubated for 3 h at 4° C. to enable CMP-collagen hybridization then overnight at 37° C. to allow for gelation. After visually confirming gelation, the gels were thoroughly washed with PBS and water.

Polyplex-Serum Activity Studies

To determine whether GPP-mediated immobilization enhanced the serum stability of the polyplexes, GPP-PEI polyplex-modified collagen gels and GPP-free PEI polyplex-encapsulating collagen gels were prepared with pCMV-Gluc plasmid. GPP-PEI polyplex-modified gels were created with polyplex containing different amounts of GPP-PEI (10, 20, or 50% GPP-PEI/Total PEI) whereas GPP-free polyplex-encapsulating gels were created similarly but with polyplex containing 0% GPP-PEI/Total PEI. These gels were preincubated under physiologically relevant conditions (37° C., 5% $CO_2$) in media containing a range of serum concentrations (0.25, 10, 20, or 50% (v/v) FBS and 1% penicillin-streptomycin (P/S) for up to 2 weeks. After the specified gel preincubation period, the gels were washed 3 times with PBS and 3 times with DMEM supplemented with 1% P/S and 10% FBS. Subsequently, NIH/3T3 cells were plated at a density of 50,000 cells/cm$^2$ in complete media (DMEM supplemented with 1% P/S and 10% FBS). The cells were allowed to adhere over a period of 6 h before treatment with tumor necrosis factor-alpha (TNF-α) (10 ng/mL), a well-known stimulator of MMP production (Zhu et al., Plos One 6(11) (2011)). Gene expression subsequently was monitored over several days after which cells were recovered by subjecting the gels to a 30 minute collagenase digestion (0.2 mg/mL in serum-free DMEM supplemented with 0.1% BSA) at 37° C. and centrifugation for 4 min at 400×g. As previously reported, elevated MMP activity was confirmed using a SENSOLYTE 520 Generic MMP Assay Kit Fluorimetric, following the manufacturer's protocol, and gene expression was monitored via detection of the luminescence of GLuc secreted into the conditioned media, via the BIO-LUX Gaussia Luciferase Assay.

DNA Stability Experiments

To assess the stability of the DNA incorporated into the collagen scaffolds, an ethidium bromide exclusion assay was performed. Polyplex-containing collagen gels were produced as previously described with 20% GPP-modified polyplex. 20% GPP-modified polyplex were further examined because 20% falls within the middle of the range of the degrees of GPP modification found to significantly enhance transfection in prior work, and could therefore provide insight on the increases in transfection efficiency observed in polyplex modified with lower (10%) and higher amounts (50%) of GPP. The gels were incubated in media (DMEM supplemented with 1% P/S and 10% FBS) under physiologically relevant conditions (37° C., 5% $CO_2$) for 2 weeks. During the incubation, media was collected from each sample 10, 12, and 14 day after starting the incubation. To examine the stability of the collected DNA, heparin was added to dissociate the polyplexes. Equal amounts of recovered DNA (0.1 μg, based on quantification using a spectrophotometric analysis) were analyzed with 1% agarose gels stained with 0.5 μg ethidium bromide per mL of TBE [tris/borate/ethylenediaminetetra-acetic acid (EDTA)] buffer. Forty μL of recovered DNA solution was added to 8 μL of 6× gel loading dye, and 40 μL of the mixture was added to each well. The gels were run at 100 V for 1 h and imaged with a BioRad Gel Doc XR (Brookhaven, CT). To analyze the gel, the ImageJ (National Institutes of Health) measurement tool was used.

Colocalization Studies

To determine if polyplexes co-internalized with collagen fragments during collagen remodeling and polyplex uptake, fluorescence-based colocalization studies were conducted. FITC-labeled collagen was incorporated into the collagen gels (25% FITC-collagen (m/m)), and 25% of the PEI used to form the polyplexes was prelabeled with Alexa Fluor 350 via Michael-type addition chemistry, according to the manufacturer's protocols. Unreacted dye was removed via dialysis (MWCO: 1000 Da). Otherwise, polyplex-modified collagen gels were prepared as previously described and subsequently preincubated in media supplemented with 10% FBS for a specified period of time ranging up to 2 weeks. NIH/3T3 cells were seeded on the surface of the gels, and after a 4 day incubation under the same conditions in the polyplex-serum activity studies, the gels were subjected to a 30 minute collagenase digestion (0.2 mg/mL in serum-free DMEM supplemented with 0.1% BSA) at 37° C. Cells were recovered by centrifugation for 4 min at 400×g. Recovered cells were replated into 24-well plates (5000 cells/cm$^2$). Six hours post-plating, the cells were fixed using 4% paraformaldehyde (PFA) for 15 min at room temperature. Additionally, the cells were treated with Trypan blue (10% v/v in PBS) to quench extracellular fluorescence. The cells were imaged using a Leica DMI6000 B inverted microscope (Wetzlar, Germany). Image analysis tools in ImageJ were used to quantify intracellular colocalization of the polyplex and collagen via Mander's Coefficient (M1) analysis.

Caveolin-1 Silencing Studies

To determine whether CMP modification encouraged cellular uptake via caveolin-1-mediated endocytosis, caveolin-1 silencing studies were conducted. Initially, NIH/3T3 cells were seeded at a density of 80,000 cells/well in 6-well tissue culture treated plates (Corning). After a 24 h recovery, cells were transfected with caveolin-1 siRNA complexes (1 μg siRNA/well) made using a commercial transfection agent (LIPOFECTAMINE RNAiMAX Reagent), according to the manufacturer's protocols. The complexes were prepared by mixing equal volumes (100 μL each) of the transfection agent solution (6 μL of LIPOFECTAMINE RNAiMAX Reagent diluted in 94 μL Opti-MEM) and siRNA solution (1 μg suspended in Opti-MEM) and allowing complexation to occur for 15 minutes. During complexation, the preplated cells were washed with Opti-MEM and covered with a fresh layer of Opti-MEM (800 μL/well). 200 μL of the siRNA complex solution was subsequently added to each well and these solutions were incubated with the cells at 37° C. for 6 h. After the incubation period, the cells were washed 3 times with PBS, and fresh DMEM (containing 1% P/S and 10% FBS) was subsequently added. After 24, 48, or 72 h, the extent of gene silencing was assessed by Western blotting using caveolin-1 antibody (N-20) (rabbit polyclonal IgG) and Goat Anti-Rabbit IgG (HRP). As a control, the same procedures were carried out using a non-coding siRNA sequence in place of the caveolin-1 siRNA.

After confirming the extent to which caveolin-1 was silenced, gene transfer studies employing caveolin-1 silencing were conducted. 24 h after transfection with the siRNA complexes, the cells were collected using standard cell recovery protocols involving treatment with trypsin (0.25% v/v). The cells were subsequently seeded onto collagen gels containing pCMV-GLuc and varying amounts of GPP-PEI, and the expression of Gaussia Luciferase was monitored after a 4 day incubation under the same conditions in the polyplex-serum activity studies via detection of luminescence using a Glomax Multimodal Plate reader (Sigma), as described by Urello et al. (Journal of Materials Chemistry B 2(46) (2014) 8174-8185).

In Vivo Gene Delivery Experiments

An Institutional Animal Care and Use Committee-approved protocol was used for all animal studies. In all studies, male, 8 week-old (CD-1) white mice (Harlan Sprague Dawley, Inc., Indianapolis, IN) were used. Lyophilized polyplex solutions were prepared as previously described using pCMV-MetLuc-mem. pCMV-MetLuc-mem encodes for a membrane-bound luciferase (MetLuc-mem) that displays on the cell surface, making it readily accessible to substrate and available for repeated in vivo imaging. To prepare the polyplexes for injection, the lyophilized polyplexes were re-suspended in MATRIGEL solution supplemented with BMP-2 (100 μg DNA/mL and 5 μg BMP-2/mL). The mixtures were vortexed and allowed to incubate on ice for approximately 1.5 h to allow bubbles formed during vortexing to disperse and for strand invasion to occur. A 1 mL sterile syringe was then used to draw up the solutions and the filled syringes were kept on ice to prevent gelation. Mice were then anesthetized using isoflurane and once under anesthesia, the abdomen of the mice were shaven and disinfected with isopropanol. Immediately before injection, the syringes containing the MATRIGEL solution were briefly warmed at room temperature and mice were injected subcutaneously with 300 μL of solution into each of four different locations on the abdomen using an 18-gauge needle. A visible pellet immediately formed at each site of injection. Each polyplex-containing pellet contained equal concentrations of MATRIGEL, BMP-2, and polyplex, while control solutions included only MATRIGEL and BMP-2. To visualize MetLuc-mem expression, images of the mice were obtained using a Caliper In vivo Imaging System Lumina (IVIS) (Perkin Elmer, Waltham, MA), after the mice were injected subcutaneously in the vicinity of each pellet with 50 µL of luciferase substrate (coelenterazine). To prepare the substrate solutions, lyophilized coelenterazine was suspended in ethanol (5 mg/mL), and the substrate stock solution was diluted into PBS to a concentration of 0.5 µg/µL immediately before injection. Images of the mice were obtained every minute following substrate injection over a period of 45 minutes until MetLuc-mem expression was no longer detectable. The LIVING IMAGE software region-of-interest (ROI) tool was subsequently used to analyze the images and determine when total luminescence within uniform areas surrounding the injection sites plateaued. Total luminescence within the areas surrounding the control pellet with no polyplex was subtracted as background within each mouse. Alternatively, the area of expression was defined as the sum of pixels within the uniform areas or ROI. The study was replicated in a total of 4 mice.

Data Processing and Statistical Analysis

All studies were performed at least in triplicate. Statistical analysis was carried out using ANOVA with a pairwise comparisons post hoc test (Tukey Test) with statistical significance accepted at $p<0.05$. Significant differences were shown by asterisks in the figures.

Results

Polyplex Activity under Physiological Relevant Conditions

A series of transfection experiments was conducted to determine whether using GPPs to immobilize polyplexes in collagen would impart stability under physiologically relevant conditions over extended periods of time. To simulate the in vivo wound environment, GPP-PEI polyplex-modified collagen gels and GPP-free PEI polyplex-encapsulating collagen gels were prepared and preincubated in media containing increasing amounts of serum for 1, 7, or 14 d. Subsequent to this preincubation, NIH/3T3 cells were plated on the modified collagen gels, treated with TNF-α to induce MMP expression, and allowed to grow for 4 days before reporter protein expression (GLuc) was monitored by analyzing luminescence in conditioned media. The luminescence detected 4 days post-plating is reported in FIG. 7. Maximum expression was detected in samples containing unmodified polyplex (0% GPP-PEI/Total PEI) after a 1 day preincubation period with 0.25% (v/v) FBS. However, the level of expression in the 0% GPP-PEI samples rapidly decreased when the samples were preincubated with higher concentrations of FBS, with a 44% decrease in luminescence when the FBS concentration increased from 0.25% to 10%, an additional 58% decrease when the FBS was increased from 10% to 20%, and a further 75% decrease when the FBS was increased from 20% to 50%. Levels of expression in samples containing unmodified polyplex became undetectable at all preincubation times longer than 1 d.

Levels of expression in the GPP-PEI polyplex-modified gels were maintained more consistently in the presence of serum (FBS). In the samples preincubated for 1 d, all of the GPP-modified samples had higher expression levels than the corresponding 0% GPP-PEI/Total PEI samples, with the exception of the samples preincubated in 0.25% FBS; under these conditions, expression in the 0% GPP-PEI samples was approximately 43% greater than the expression levels in any of the GPP-modified samples. After 1 day of preincubation, the 10% GPP-PEI/Total PEI polyplexes had the highest levels of expression when preincubated with either 0.25 or 10% FBS, and expression levels decreased by approximately 33% when these samples were preincubated in media containing either 20% or 50% FBS. The opposite trend was noted in the more extensively modified polyplexes, with the 20% and 50% GPP-PEI/Total PEI polyplexes exhibiting the lowest levels of expression after preincubation with 0.25% (v/v) FBS. The luminescence detected in the 20% and 50% GPP-PEI samples increased approximately 120% and 320%, respectively, when these samples were preincubated with any of the higher concentrations of serum (10%, 20%, or 50%) versus preincubation with 0.25% (v/v) FBS.

After longer preincubation periods, the differences in the levels of expression in samples containing unmodified polyplex (0% GPP-PEI) vs. GPP-modified polyplex became more pronounced. When samples were preincubated for 1 week, expression levels in the unmodified samples were undetectable, whereas in the 10% GPP-PEI/Total PEI polyplex samples, the levels of luminescence remained detectable but decreased approximately 34%, 35%, 50%, and 85% for the 0.25%, 10%, 20%, and 50% FBS (v/v) samples, respectively, as compared with the luminescence in 1 day preincubated samples. In the 0.25% FBS samples modified with 20% and 50% GPP-PEI polyplexes, the levels of expression increased by approximately 51% and 65%, respectively, compared to the corresponding 1 day preincubated samples. Levels of expression were higher when the 20% and 50% GPP-PEI samples were preincubated for 1 week with 10% and 20% FBS, as compared with 0.25% or 50% FBS, and the overall level of expression significantly increased in the 20% GPP-PEI/Total PEI samples when these samples were incubated for 7 days vs. 1 day at these FBS concentrations. After a 14 day preincubation, significant expression was only detected in the 50% GPP-PEI/Total PEI modified gels that were preincubated with 10% and 20% FBS.

DNA Integrity Under Physiologically Relevant Conditions

Figure 8:
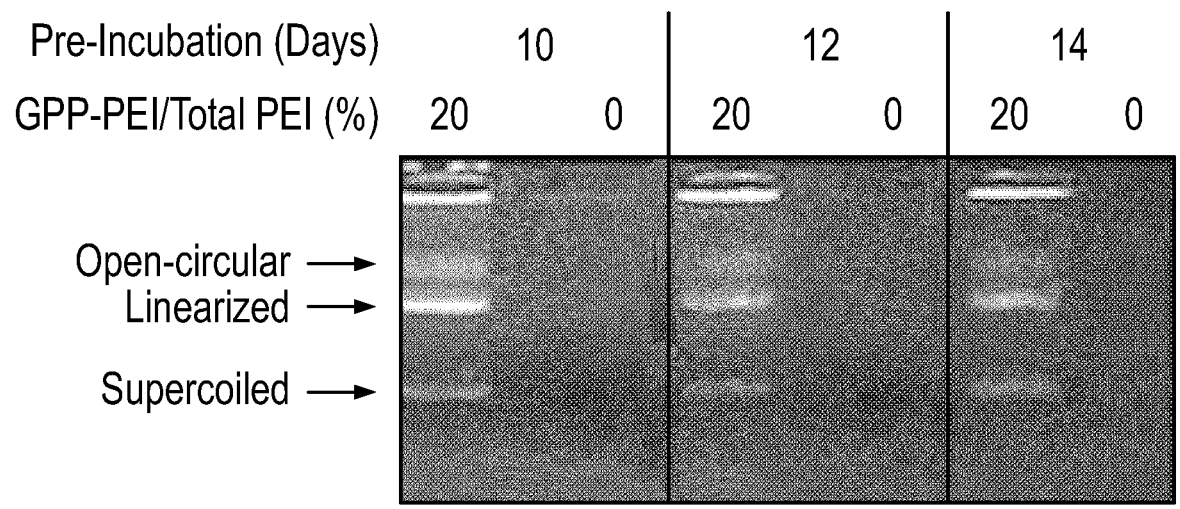
FIG. 8 shows DNA stability analyses. a) A representative agarose gel showing the integrity of DNA recovered from 20% and 0% GPP-PEI/Total PEI polyplex-containing collagen gels after various preincubation time periods in media (DMEM supplemented with 10% FBS). b) Quantification of gel fluorescence observed in GPP-modified samples where the mean+/−standard deviation is for a total of three separately prepared and analyzed samples run within the same gel.
Figure 8:
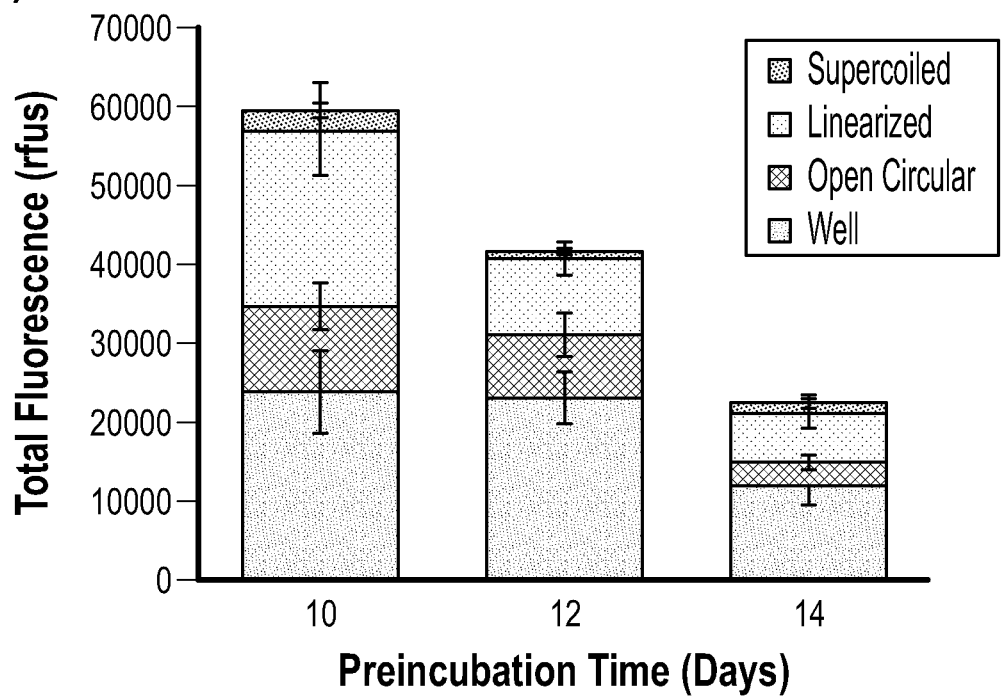

To determine if the integrity of the DNA was preserved under physiologically relevant conditions that would be encountered by the scaffold in vivo pre-cellular invasion, DNA was recovered from the media collected from polyplex-containing collagen gels after various serum preincubation periods. The integrity of the DNA was assessed by agarose gel electrophoresis (FIG. 8). The three bands characteristic of plasmid DNA (open circular, linearized, and supercoiled) were visible in each sample collected from the GPP-PEI polyplex-modified gels. These three bands notably faded in intensity when samples were collected from gels that were preincubated for longer time periods. For example, there was a 37% decrease in the plasmid band intensity observed in the 20% GPP-PEI polyplex-modified sample collected after a 12 day incubation, and a 53% decrease in the plasmid band intensity in the sample collected after 14 d, as compared to those in the 10 day sample. Fluorescence was also observed in the wells for each preincubated 20% GPP-PEI sample. In comparison, fluorescence from the three plasmid bands was difficult to detect with the naked eye in the samples collected from collagen gels containing 0% GPP-PEI polyplex, even though the same quantity of DNA was employed in the polyplexes as indicated by spectrophotometric analysis. Based upon image analysis of the bands, the 0% GPP-PEI sample band intensities exhibited decreases of 22% and 53%, respectively, for samples collected after 12 day and 14 day vs. 10 d. Fluorescence/DNA was also observed in the wells of samples collected from the GPP-PEI polyplex-modified gels. DNA immobilization in the wells suggested that complexation of DNA with PEI remained intact despite the addition of heparin, a method commonly used to completely dissociate DNA polyplexes (Urello et al., Journal of Materials Chemistry B 2(46) (2014) 8174-8185).

Collagen-Polyplex Co-Internalization Study

Cell-triggered release and efficient cell-uptake are essential for high efficiency expression in vivo. To determine the extent to which endocytic collagen remodeling was able to drive the gene delivery process in the GPP-PEI polyplex-modified collagen versus the GPP-free polyplex-encapsulated collagen, confocal microscopy was used to examine the cellular co-internalization of polyplex and collagen for 20% GPP-PEI/collagen samples. 20% GPP-PEI/collagen samples were analyzed because the highest levels of transfection were observed within these samples post incubation in 10% FBS supplemented media for up to a 10 day preincubation period. In order to study co-localization of the two materials, FITC-labeled collagen was incorporated into the collagen gels (25% (m/m) FITC-collagen) and 25% of the PEI (m/m) used in the polyplexes was labeled with Alexa Fluor 350. Gels were preincubated in media supplemented with 10% FBS for a specified period of time ranging from 5 days up to 2 weeks; subsequently, NIH/3T3 cells were plated on the preincubated gels, and after a 4 day incubation, the cells were recovered and replated for imaging. Intracellular colocalization of the polyplex and collagen was quantified via Mander's Coefficient (M1) analysis where M1 ranges from 0 to 1 and is defined as the ratio of the summed intensities of pixels from the blue image (polyplex) for which the intensity in the green channel (collagen) is over zero to the total intensity in the blue channel (polyplex). Therefore, M1 is a good indicator of the share of the blue signal (polyplex) corresponding with a signal in the green channel (collagen) over its total intensity.

Figure 9:
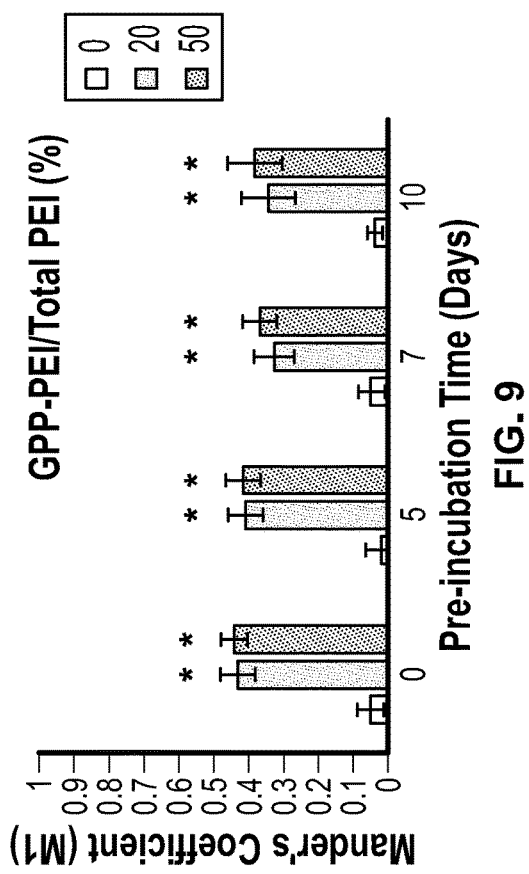
FIG. 9 shows the collagen-polyplex colocalization study. Quantitative analysis of intracellular collagen-polyplex association by calculation of Mander's coefficients for colocalization of FITC-collagen with Alexa Fluor 350-polyplexes in NIH/3T3 cells. For GPP-PEI/total PEI=0 and 20, the data for the 0, 5, and 7 day pre-incubations represent the mean+/−standard deviation of 10 separately analyzed cells. For the 10 day preincubation, 5 separately analyzed cells were analyzed. For the 50% GPP-PEI, the data represent the mean+/−standard deviation of 5 separately analyzed cells. * denotes a statistically-significant difference ($p<0.05$) relative to the unmodified polyplex samples.

As shown in FIG. 9, the Mander's Coefficient was an order of magnitude greater in samples modified with GPP as compared to the unmodified samples. In the samples containing unmodified polyplex, the Mander's coefficient indicated insignificant colocalization between the polyplex and collagen after each incubation period, whereas in the samples modified with 20% GPP-PEI polyplex, the Mander's Coefficient was approximately 0.4 after each incubation period. The Mander's Coefficient for each sample remained constant, independent of preincubation time. Notably, less polyplex uptake was detected in the unmodified samples versus the GPP-modified samples, particularly after longer preincubation periods. These findings are consistent with previous data confirming that the unmodified polyplexes were retained for shorter periods, and therefore less polyplex was available for uptake after longer preincubations.

Intracellular Trafficking Study

Figure 10:
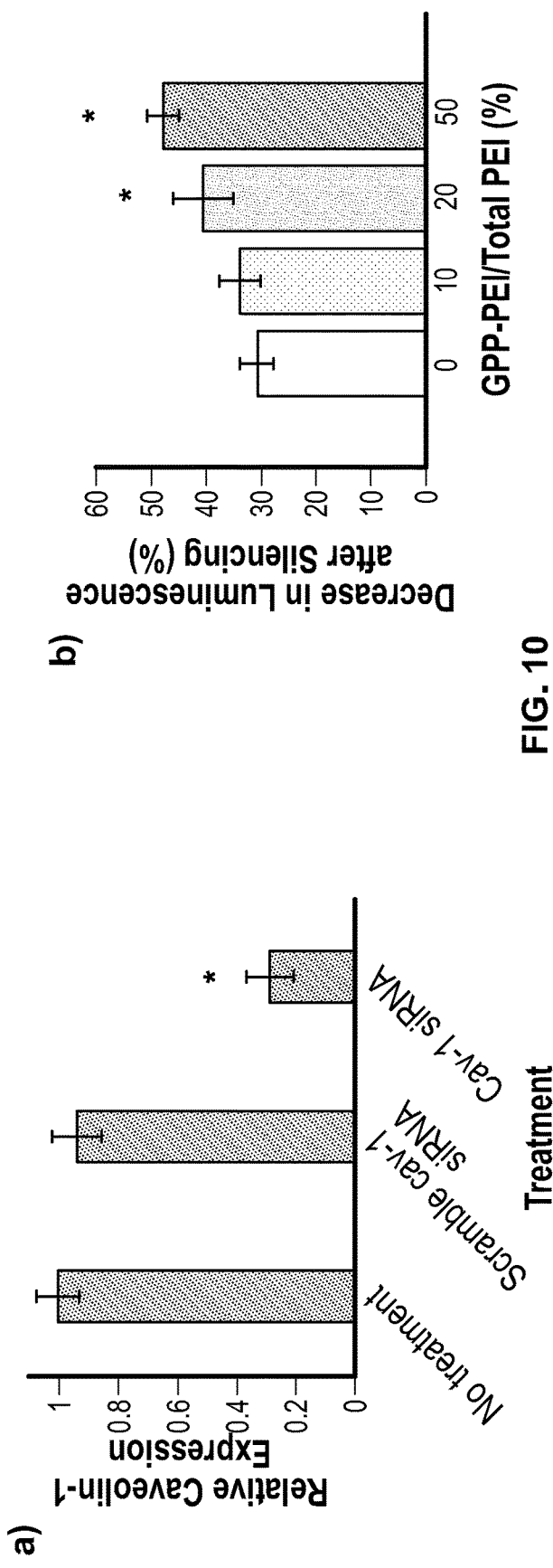
FIG. 10 shows cellular uptake of GPP-modified polyplex after caveolin-1 silencing, a) Caveolin-1 (cav-1) silencing efficiencies were determined 2 days post-treatment via Western blots. Expression levels relative to a non-treated control also were examined 1 day and 3 days post treatment (FIG. 12). * denotes a statistically-significant difference ($p<0.05$) relative to the non-treated control controls. b) Changes in polyplex endocytic pathways mediated by GPP-modification and continued association with collagen fragments were elucidated in caveolin-1 silencing transfection experiments. Each data point represents the mean+/−standard deviation for a total of six separately prepared and analyzed samples.

Collagen endocytosis occurs naturally during tissue remodeling through a mechanism involving MMP-mediated release of collagen fragments followed by $\alpha_2\beta_1$-integrin and caveolin-1-regulated uptake. To examine whether GPP-modification and collagen association affected the endocytic uptake of polyplexes, transfection experiments were conducted as previously described, but using NIH/3T3 cells with silenced caveolin-1 expression cultured in media supplemented with collagenase (FIG. 10). Significant reductions in gene expression were observed following caveolin-1 suppression in all samples, suggesting that both the unmodified and GPP-modified polyplexes were internalized via caveolar endocytosis. Notably, the decrease in expression with caveolin-1 silencing was directly dependent upon the amount of GPP-PEI/total PEI incorporated into the polyplex. In both the 20% and 50% GPP-PEI/total PEI polyplex samples, the changes in luminescence after silencing were significantly greater (30% and 53% greater, respectively) than that observed in the unmodified sample.

Expression in an In Vivo Model

A simple in vivo model was used to test the efficacy of the CMP-based gene transfer approach during tissue repair, using subcutaneous ECM depots to mimic the wound environment (FIG. 11). 10% and 50% GPP modified polyplex were employed to determine the impact of varying the degree of CMP modification on expression within an in vivo model over the range of GPP modifications determined to impact transgene expression in the previous in vitro studies. The lack of an excision simplified the model while allowing for the examination of gene expression in a similar environment, containing the same cell types/tissues, and conceivably a minor inflammatory response triggered by the foreign body injection (unmeasured). MATRIGEL was employed as the delivery substrate due to its prior successful implementation in both wound and bone healing studies and its potential to hybridize with CMPs due to its high collagen content. As observed in FIG. 11b-c, insignificant levels of luminescence were detected, at each of the time points, in the pellets devoid of polyplex within the representative mouse. Meanwhile, in the samples containing unmodified polyplex, only short periods (2-3 d) of low-level luminescence were detected at 2 to 4 days post-injection. Prolonged, localized expression was observed only in pellets containing GPP-modified polyplex. Expression was observed within the pellets for periods of 16 days and 20 days in the 10% and 50% GPP-modified polyplex samples, respectively. Furthermore, the initial area over which expression was observed at 4 days post-injection was approximately 70% smaller in the 50% versus the 10% GPP-PEI polyplex sample. In addition to being smaller, the expression in the 50% GPP-PEI sample remained consistently localized over the entire time period over which expression was detectable. While the observed expression appeared markedly more localized and of longer duration in the 50% GPP-PEI polyplex samples as compared to the 10% samples, the overall expression levels were significantly higher in the 10% GPP-PEI polyplex. For instance, in the representative mouse, expression was first detected in the 10% GPP-PEI sample on the same day the maximum level of expression was detected, e.g., 4 days post-injection. A week after injection, the levels of expression in the 10% GPP-PEI samples had decreased by more than 75% and expression levels became insignificant by day 16. In the 50% GPP-PEI samples, expression was overall more consistent from day to day. Expression was first detected on day 3 and remained relatively consistent until day 10 before reaching a maximum level of expression on day 11 and then decreasing. The maximum luminescence detected in the 50% GPP-PEI sample was approximately half that detected in the 10% GPP-PEI sample. In FIG. 11d, the replicates are reported as a median value in order to clearly demonstrate the spread of replicates, while highlighting the consistent capacity of CMP modification to achieve tailorable, sustained expression within a collagen-based scaffold. Maximum transgene expression was similar detected within the 10% GPP-PEI polyplex samples within the first week post injection and determined to be approximately 80% that detected in the 50% GPP-PEI polyplex sample. Expression in the rapidly decreased within the 10% sample after a week period, decreasing by nearly 70% by day 14, while maximum expression was not achieved in the 50% sample until day 12. Additionally, the area in which expression was observed (FIG. 11c-d), was determined to be overall smaller and more consistent in the 50% GPP modified polyplex samples versus the 10% modified polyplex over the duration of the work. For instance, within the representative mouse, the maximum area of expression in the 50% sample was over 3.1-fold greater than that observed in the 10% sample. The 0% areas of expression were not included due to their much lower values relative to the GPP modified samples.

Discussion

Tissue repair is a complicated process largely driven by dynamic ECM remodeling. In localized delivery applications, particularly those aimed at tissue repair, substrate-mediated DNA delivery offers many advantages through its improved capacity to control retention/release of gene cargoes both spatially and temporally, as well as to increase serum stability through steric inhibition. Furthermore, delivery systems can be purposefully engineered to synchronize cell-mediated production of healing factors with natural tissue remodeling/healing via design/application of cell responsive-materials. Accordingly, the properties of many native, dynamic ECM proteins, such as collagen, make them attractive delivery substrates; however, substrate-mediated gene delivery approaches continue to face major obstacles when applied in healing tissues due to the exceptionally harsh, nuclease-rich environment and prolonged repair periods, which can extend over weeks to months. To address these issues, we sought to use triple-helix strand invasion to integrate gene cargoes into collagen matrices to both abrogate DNA losses due to nuclease degradation, and directly harness native endocytic repair processes for improved gene localization, optimal release kinetics, and efficient intracellular trafficking. Our previous experiments demonstrated the ability to tailor the release/retention of PEI polyplex from collagen, one of the most well-established, natural biomaterials, through the incorporation of different amounts of adjustable CMP-linkers into the polyplex, and also showed enhancements in transfection efficiency of GPP-PEI polyplexes delivered from collagen. In this work, we demonstrate the utility of the CMP materials in vivo to harness the tissue remodeling process to trigger gene stabilization and delivery. Our results indicate the benefits of the CMP approach for producing enhanced, prolonged, and better localized gene expression in an in vivo model.

Figure 7:
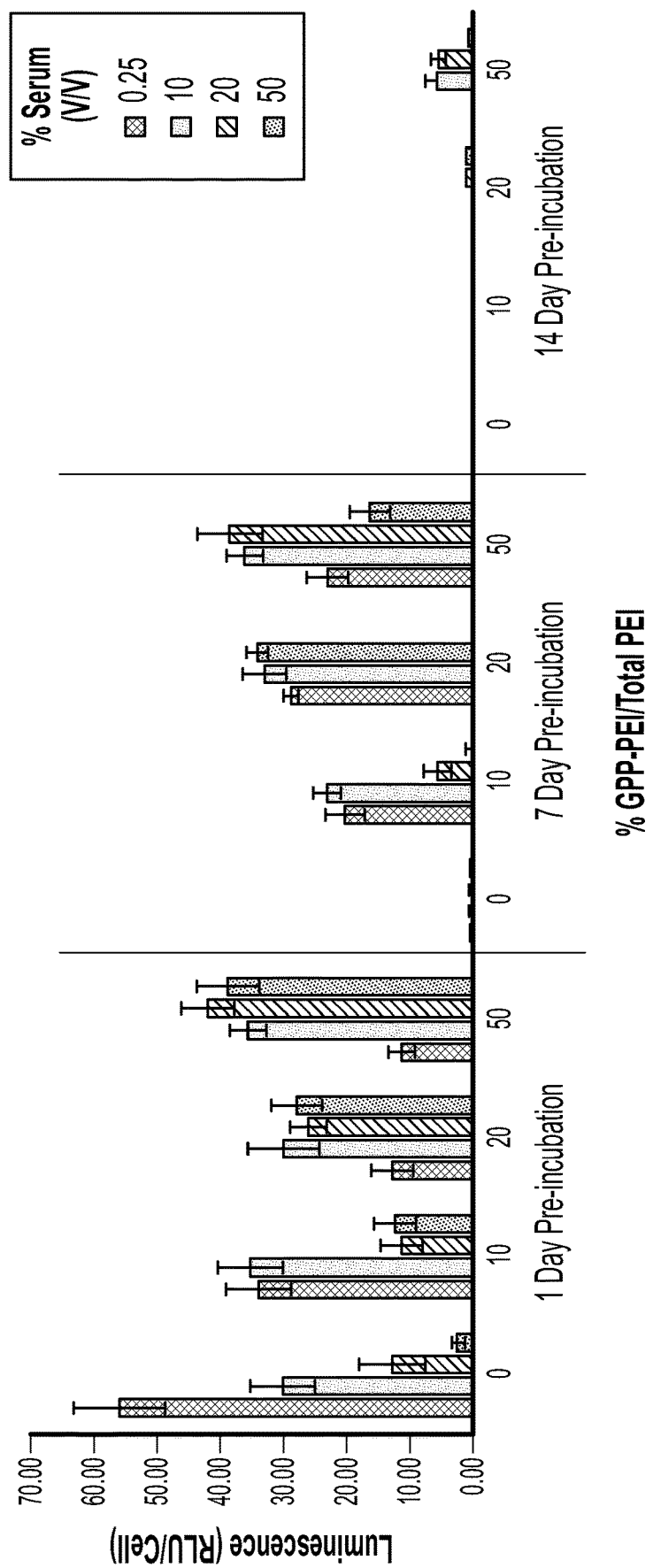
FIG. 7 shows polyplex activity studies. Polyplex-containing collagen gels were preincubated at 37° C. in media containing a range of serum concentrations (0.25%-50% (v/v)) for up to 2 weeks. NIH/3T3 cells were plated onto the preincubated gels and treated with TNF-α to stimulate MMP expression. The data represent the luminescence in the media due to luciferase expression by the cells after 4 d on the gels. Each data point represents the mean+/−standard deviation for a total of eight separately prepared and analyzed samples.

During tissue repair, collagen remodeling proceeds through processes regulated by MMP-1, $\alpha_2\beta_1$ integrin, and caveolin-1. Our prior studies showed that significant transfection was contingent on the stimulation of MMP expression, providing the first evidence of cell-responsive delivery via collagen remodeling mechanisms. Furthermore, the improvement in transfection efficiency in the GPP-PEI polyplex-modified gels compared to the unmodified polyplex gels was vastly enhanced when gels were preincubated under physiologically relevant conditions in the presence of serum over long periods of time, indicating fundamental differences in the surface properties and stability of the polyplexes by virtue of their interactions with collagen. In particular, transfection studies with gels preincubated in serum concentrations of 0.25-50% (v/v) FBS over time periods ranging from 1 day up to 2 weeks demonstrated that GPP-PEI incorporation had a significant effect on gene expression as a function of both time and serum concentration (FIG. 7). For example, expression levels rapidly decreased when the unmodified structures were incubated with higher serum concentrations and for longer periods, and for preincubation periods over a week, no significant expression was detected. In contrast, significant levels of expression were observed in the GPP-PEI polyplex samples even after a week-long preincubation period when the polyplex contained 10%-50% GPP/Total PEI, and the 50% GPP-PEI/Total PEI samples exhibited marked expression even after a 2-week long preincubation with serum. Other matrix-mediated gene delivery approaches have demonstrated the capacity to facilitate expression for similar periods, however the capacity to preserve polyplex activity under physiologically relevant conditions (high serum concentrations at 37° C.) before cell invasion as demonstrated by our preincubation studies, has largely been unstudied. Similar studies may serve as a useful predictor of gene-activated matrix stability in applications in which cells are not initially encapsulated within the matrix and cellular invasion is delayed such as wound repair or tissue engineering.

Differences in gene expression levels are likely due to differences in both polyplex retention/release kinetics as well as differences in gene stability/processing associated with collagen linkage. As previously observed, approximately 20% less DNA was initially retained in the unmodified polyplex samples as compared with the GPP-PEI polyplex samples, and the DNA that was retained was released approximately 1.63×, 2.10×, and 3.25× faster than the DNA in the 10, 20, and 50% GPP-PEI polyplexes, respectively, over 15 days in PBS. While the release kinetics were likely not identical in the media containing serum, our current study suggests that GPP modification and multivalency still improve polyplex retention relative to unmodified polyplex retention on collagen even during preincubation with a range of serum concentrations for up to 2-weeks. In the unmodified polyplex samples, upon release into the serum-supplemented media, the unmodified polyplex's high density of positive surface charges likely led to many interactions with negatively charged serum proteins such as albumin, leading to rapid aggregation and loss of viability within an hour. Due to the faster release kinetics of the gel containing the unmodified polyplex, compounded by the fact it initially held less polyplex, the collagen's concentration of viable polyplex decreased at a significantly faster rate leading to lower levels of gene expression, which would also be exacerbated by the higher concentrations of serum expediting the aggregation of released polyplex. Differences in expression levels as a function of time were also observed for polyplex containing different amounts of GPP-PEI/Total PEI, with samples containing higher amounts of GPP-PEI/Total PEI (10%, 20%, and 50%) exhibiting higher expression levels particularly after longer time periods of preincubation in serum.

The increase in expression observed in the more extensively modified polyplexes at higher serum concentrations was also likely due to a combination of effects stemming from scaffold and/or polyplex interactions with serum proteins. While collagen encourages cellular adhesion, serum gradients have been shown to encourage cellular in-growth, enhanced mobility, and increased proliferation. In substrate-mediated delivery, cellular access to DNA, which is determined by cell mobility and DNA scaffold concentration, is one of the largest determinants of gene expression. Preincubation of the gels with serum likely leads to the absorption of serum proteins onto the scaffold, making the environment more hospitable to the cells. In unpublished observations, cells plated on these samples appeared more likely enter the scaffold and remain in the scaffold, unlike in the scaffolds preincubated in lower levels of serum, where it was observed cells were predominantly located in the top layers of the gels or adhered to the bottom of the polystyrene plate.

We also postulate that increased association with collagen may have encouraged favorable interaction between the polyplexes and serum proteins, leading to alterations in the cellular uptake and subsequent intracellular trafficking of the released gene-containing structures. FBS contains a myriad of proteins, including adhesion mediators as well as signaling and transport proteins. One possibility is pre-exposure to serum allowed the positively charged polyplexes to interact with negatively charged serum proteins while still remaining stably bound to collagen. This interaction would decrease the charge of the polyplex, diminishing the tendency for polyplexes to aggregate or be degraded post release. Pre-exposure of PEI polyplex and other positively charged nanoparticles to serum has previously been documented to have this effect.

The integration of polyplex in collagen, along with serum protein adsorption, has also been shown to affect cellular uptake mechanisms, with these interactions suggested to lead to greater endocytic uptake and/or more efficient intracellular trafficking to the nucleus. In fact, our studies supported the existence of these effects in the CMP-polyplex materials, showing that the higher amounts of GPP peptide affected not only polyplex release kinetics, but the polyplex's final composition. In addition to mediating affinity with the collagen scaffold, the GPP peptide encouraged the polyplex to associate with the collagen fragments post-release, as shown in the colocalization study (FIG. 9). The consistent and significant differences between the Mander's overlap coefficient (M1) for collagen association with the GPP polyplex, versus the unmodified polyplex, even after extended preincubation periods, indicated a continued GPP-mediated association of GPP-PEI polyplex with collagen following liberation and cellular uptake. Moreover, M1 values range between 0 to 1, therefore the mean M1 value of 0.38 for the 20% GPP modified samples at the different time points is indicative of significant overlap between the two components comparable to those recorded for labeled components initially incorporated into polyplex during formulation. The continued CMP-collagen interaction is consistent with previous studies that have shown that the serum stability of the almost-neutral CMPs allows them to associate with remodeling collagen in highly complex environments including in vivo murine tumor, bone abnormality, and wound models. Continued association of the polyplex with collagen fragments has many potential benefits. It may further reduce the surface charge of the polyplex, reducing interaction with serum proteins and aggregation. In other works, neutral, hydrophilic polymers, such as poly(ethylene glycol) (PEG), or anionic polymers, such as alginate or hyaluronic acid, are used to help shield the high density of positive charges of the PEI. In our system, collagen fragments may play a similar role and afford the released polyplex with both increased serum stability and resistance to aggregation and dissociation. Increased plasmid stability in GPP-PEI polyplex-modified gels was confirmed using gel electrophoresis. As shown in FIG. 8, intact plasmid DNA was present in the media collected from all GPP-PEI polyplex-modified samples, even after a 14 day preincubation, indicating that the DNA was at least partially protected. After longer preincubation, the plasmid bands were reduced in intensity, indicating a degree of degradation, but the fluorescence intensity still remained significantly higher than the levels observed in the unmodified polyplex samples. Because equal amounts of DNA were loaded into each well, the result suggests that CMP-mediated DNA incorporation into the collagen gel protected the DNA more effectively than DNA retained through non-specific interactions. We hypothesize that GPP-PEI polyplexes were able to better preserve the integrity of the DNA because of their slower release kinetics, causing DNA to remain bound for longer periods, and because of the continued association of polyplex with collagen fragments post-release from the scaffold. The fluorescence observed in the wells of the samples collected from the GPP-PEI polyplex-modified gels suggests that complexes of the DNA with either PEI, a serum protein, and/or collagen, are present, and these structures were not dissembled with heparin as readily as those collected in our previous, serum-free study.

The collagen fragments may also impart other collagen-specific benefits. Collagen has been used to mediate gene delivery in various forms, ranging from macroscopic porous sponges to nanoparticles (100-300 nm in diameter). Atelocollagen-mediated delivery has been shown to increase cellular uptake and nuclease resistance when compared to typical polycation transfer methods and is capable of transferring genes into both dividing and non-dividing cells. While the majority of current studies utilize atelocollagen for localized delivery, previous works have shown atelocollagen-nucleic acid nanoparticles could be successfully implemented for systemic delivery, lengthening circulation time and increasing treatment efficiency. The collagen fragments also have a series of integrin binding sites, which may aid in encouraging cellular internalization. To better understand the impact of the GPP peptide on polyplex uptake mechanisms, transfection experiments were conducted in which the caveolar endocytosis pathway was blocked. The caveolar endocytic pathway was chosen because previous studies with PEI polyplex have shown that this pathway initiates high efficiency intracellular trafficking to the nucleus and expression, and therefore targeting this pathway is desirable. The GPP peptide, as well as endogenous collagen, contains an $\alpha_2\beta_1$-integrin binding site, which is known to mediate caveolar endocytosis by collagen fragments. We discovered a direct correlation between the percent of GPP-PEI/Total PEI incorporated into the polyplex and the impact caveolin-1 silencing had on transfection. The decrease in transfection between the unmodified polyplex vs. the 20% and 50% GPP-PEI/Total PEI polyplexes (30% and 53%, respectively), was significant (p-value<0.05). The results confirm that the GPP peptide acts not only as a tether to control release, but also as a ligand, providing a better-defined, efficient pathway way into the cells. The change in cellular uptake was likely due to the synergistic effects of the proline-rich CMP and collagen fragments. Further experimentation would be necessary to elucidate which effect was prevalent.

Animal models have demonstrated that CMPs can be used to detect areas of excessive collagen remodeling, such as tumors and joints, and CMPs can anchor cytoactive factors and collagen in wound beds to improve wound closure and granulation. Utilizing a mouse model, in vivo gene expression in polyplex encapsulating or GPP-PEI polyplex-modified subcutaneous MATRIGEL pellets was monitored. MATRIGEL is a widely used, commercially available substrate that consists of basement membrane ECM components such as type IV collagen. While type IV collagen has a lower triple helical content than type I collagen, significant CMP-type IV collagen interactions have been documented, albeit with lower efficiency than CMP-type I collagen interactions. Type IV collagen has also been successfully employed in wound and bone in past studies. Through GPP modification of the polyplex, we demonstrated the ability to enhance, extend, and localize expression, even from the type IV collagen-rich pellets. Levels of expression in the pellets with GPP-PEI polyplex were higher and the duration of expression was directly dependent on the amount of GPP-PEI/Total PEI in the polyplex. For instance, maximum expression in the 10% GPP-PEI/Total PEI pellet is 100-fold greater than in the unmodified polyplex pellet and significant expression is observed for approximately 20 days versus less than a week in the unmodified samples. Alternatively, expression in the 50% GPP-PEI/Total PEI pellet was observed for up to 25 days. This relationship was likely due to a difference in release kinetics, stability, and cellular internalization and is supported by the observation that level of expression in the 50% GPP-PEI/Total PEI pellet was generally lower than that observed in the 10% GPP-PEI/Total PEI pellet, but was more localized and occurred over a longer duration. Our work, as well as other works with CMPs, have demonstrated that the incorporation of multiple CMPs onto a nanostructure/polymers dramatically affects mobility in collagen-based scaffolds due to the affinity CMPs have, particularly for remodeled collagen. The reversible, serum-stable reaction prevents CMP-modified materials from leaving the delivery site, and as demonstrated here, can be used to both control and localize release. Other matrix-mediated gene delivery approaches have achieved similar expression periods as achieved in this work ranging from days to a month within similar subcutaneous animal implants, while some have achieved multi-month expression periods. However, our in vivo results demonstrate the ease in which expression can be tailored via variation of DNA carrier GPP composition and the potential benefits of promoting localized delivery post carrier release through GPP targeting of remodeled collagen. These unique characteristics make CMP-mediated delivery both innovative and of great value in complicated applications like wound repair which benefit from controlled multi-therapeutic delivery and avoidance off-target delivery.

Additionally, while other matrix-mediated gene delivery approaches have demonstrated similar duration of expression to that we report, our work differs substantially in that most approaches rely solely on scaffold degradation to mediate DNA delivery, limiting localized responsiveness and enhancing the danger of off-target delivery. The application of protease-sensitive scaffolds has provided a means of engineering localized, cell-triggered gene transfer activity, but has not eliminated the danger of vector escape or addressed potential issues associated with achieving gene delivery tailored to the irregular environments common in wound repair. CMP modification of non-viral vectors has provided a method for tailoring release/retention from collagen, and additional studies strongly suggest the reversible nature of CMP/collagen hybridization synergistically prevent vector escape from the delivery site through re-association with the collagen scaffold and surrounding remodeled collagen. Furthermore, unlike most matrix-mediated approaches, CMP modification directly addresses obstacles associated with both the extra- and intracellular environments. CMP modification has been demonstrated to not only enhance vector availability/stability in the delivery site, but also to provide a ligand promoting cellular uptake through endocytic pathways linked to high efficiency expression. Additional studies have demonstrated that the CMPs' unique triple helical structure is integral in achieving enhanced cellular binding and cell penetration. For instance, CMPs were successfully used to enhance liposome targeting of melanoma cells through specific ligand/receptor interactions, whereas no binding to non-targeted cells was recorded. Given the many obstacles that inhibit gene delivery, the introduction of a novel multifunctional peptide has enormous potential for accelerating vector optimization required for pragmatic/clinical application. While multifunctional peptide vectors have been developed, typically through the fusion of peptide moieties known to overcome a particular barriers (ex: DNA condensation, cellular internalization/targeting, nuclear localization), only a small fraction have demonstrated utility in vivo, suggesting that the practice of studying the effects of these moieties individually is not sufficient. The continued development of multifunctional CMPs and continued studies examining the impact of CMP modification on different aspects of vector efficiency has enormous potential in advancing gene delivery applications.

Conclusion

Protease-sensitive biomaterials, including collagen, have been employed to synchronize the delivery of cues with tissue remodeling and the reparative process. The availability and biocompatibility of collagen have secured its place as a versatile biomaterial, both as a bioactive scaffold and as a cell-responsive reservoir for additional therapeutics. While many techniques for modifying collagen with therapeutics have been developed, the biomimetic approach utilizing CMPs has many advantages including its highly specific yet physical nature and its versatility in regards to tuning release/retention. In this work, CMP modification was shown to modulate and enhance delivery of PEI polyplex from collagen-based scaffolds both in vitro and in vivo. Variation of the amount of GPP-PEI/Total PEI in PEI polyplexes demonstrated the capacity to control release and stabilize polyplex, even in the presence of high concentrations of serum under physiologically relevant conditions for up to 2 weeks. The cell-responsive nature of the GPP-polyplex-modified collagen substrates was clearly indicated by the fact that significant transfection was only observed in the presence of MMPs/collagen remodeling. Furthermore, the colocalization of the GPP-PEI polyplex with collagen following polyplex release from the scaffold improved DNA structural integrity and enhanced the targeting of the polyplexes into a high efficiency endocytic pathway leading to gene expression. The unique properties of the GPP peptide allowed for its use as both an adjustable tether, via CMP-collagen hybridization, and as an endocytic ligand. This method allowed for the "hijacking" of the natural process of collagen remodeling to overcome major obstacles in gene delivery, such as improving vector activity in the presence of serum and providing a well-defined intracellular pathway, in addition to serving as a cell-responsive trigger for release. As suggested by our in vivo work, these properties can translate to even more complex systems and have great potential in the treatment of sites in which excessive collagen remodeling occurs.

Example 3. Collagen-Mimetic Peptides as Tools for Prolonged, Multigene Expression Conducive for GF Delivery in Wounds Wound healing is a complex process governed by intricate cellular signaling mediated by numerous components including GFs. To promote healing in nonhealing, chronic wounds, in which healing has become uncoordinated and GF activity is compromised, the topical and sustained delivery of vital GF proteins and GF genes has aided in promoting healing; however, clinical translation has stagnated due to delivery obstacles, validated safety concerns with oncogenic and off-target effects, and an overall lack of efficacy. Recent studies have suggested clinical failure may be due to the focus of most current delivery systems on single GF or dual GF protein/gene delivery without controlled release. A CMP-based strategy for mimicking endogenous healing via controlled delivery of multiple GFs is demonstrated. Specifically, the capacity to tailor the delivery of multiple proteins, including both reporter proteins and functional proteins, was demonstrated within the same system over periods of nearly a month, a relevant time frame in chronic wound repair. The expression profiles of two GFs integral for different stages of healing, PDGF-BB and KGF, were individually tailored within the same collagen-based scaffolds, and these GFs were expressed at levels capable of triggering desirable cell behaviors. Moreover, the observed capacity to alter expression of multiple genes suggests that the CMP/collagen system may be used to tailor the expression of a plethora of additional GFs and signaling molecules for different regenerative medicine applications.

Introduction

Wound healing is a complex process consisting of several integrated stages, including inflammation, granulation/neoangiogenesis, re-epithelization, and tissue remodeling/maturation. Each stage is governed by intricate cellular signaling orchestrated by reciprocal ECM-cell interactions and a plethora of cytokines, chemokines, growth factors (GFs), and nuclear receptors facilitating pro-mitogenic gene expression and cell division (FIG. 14). Coordination of these processes is vital in wound repair, and disruption of these processes, most commonly as the result of ischemia, compromises cellular functions and compromises GF activity, resulting in chronic nonhealing wounds.

As summarized in FIG. 14, a multitude of signaling molecules, cell types, and ECM components are required for each process underlying repair, such as ECM regeneration and angiogenesis, to facilitate complete healing. For instance, many GFs are required for different time periods during the stages of healing. Platelet-derived growth factor (PDGF), transforming growth factor (TGF), epidermal growth factor (EGF), and insulin-like growth factor (IGF) mitigate cell recruitment and activation during the early stages of wound repair; TGF, EGF, and PDGF are vital for matrix synthesis throughout healing; and fibroblast growth factor (FGF), PDGF, and vascular endothelial growth factor (VEGF) mediate angiogenesis and tissue maturation. Understandably, recognition of the integral roles of GFs has led to the development of GF-based therapies in chronic wound repair. However, as previously discussed, clinical translation of both topical and sustained release therapies of GF proteins and GF genes has been limited. Clinical failure has largely been blamed on insufficient delivery and oncogenic and immunogenic concerns, yet emerging results strongly suggest insufficiencies in clinical outcomes also are exasperated by a lack of control of synergistic behaviors of multiple GFs, and the focus on the delivery of only a single factor or component as opposed to combinations of factors. For instance, as previously discussed, the only GF treatment approved for treatment of diabetic foot ulcers (DFUs), Becaplermin (REGRANEX), consists of repetitive, extra-physiological doses of a single GF, PDGF-BB, and boasts only modest improvements in the number of healed DFUs (<10%) due in part to the PDGF-BB-stimulated hyper-granulation which impedes epithelization and progression of the reparative process. The simultaneous or sequential delivery of additional GFs has the potential to trigger progression through the orderly reparative process.

Acknowledgement that the complex cellular processes of cell migration, differentiation, and proliferation require specific GFs with time-dependent and spatial distributions has led to the development of multiple GF delivery strategies. Composite polymer systems have been engineered for spatio-temporal delivery of multiple GFs with specific release kinetics. For instance, the early stages of angiogenesis require VEGF, FGF, and angiopoietin-1 to disrupt the structure of existing blood vessels, followed by the release of angiopoietin-1 and PDGF-BB to stabilize newly formed blood vessels. In turn, the sequential and simultaneous delivery of these GFs has been demonstrated to enhance vascularization compared to when solely VEGF is delivered. In a similar manner, proteolytic degradation has been used to mediate sequential delivery of BMP-2 and IGF-1 from a degradable layered structure, or trigger BMP-2 and TGF-$\beta$3 delivery from degradable alginate hydrogels, or stimulate VEGF and BMP-2 delivery from gelatin microparticles; dual GF delivery promoted enhanced healing compared to the delivery of a single GF. Additionally, the inherently different affinities that VEGF, PDGF-BB and TGF-$\beta$1 have for alginate have been utilized to govern release kinetics and promote enhanced vascularization compared to when only basic fibroblast growth factor (bFGF) was delivered. Delivery systems that chemical immobilize or physically encapsulate GFs in delivery systems have been similarly employed to govern delivery; however, the obstacles that inhibit the delivery of single factors via these techniques, namely off-target delivery and oncogenic concerns, further complicate the delivery of multiple factors.

Multi-growth factor gene delivery strategies also have garnered interest due to the potential benefits of GF gene vs. GF protein therapies such as reduced costs and GF micro-localization and improved bioactivity. To mediate sequential delivery, polymer systems similar to those engineered for protein delivery have been utilized. For instance, tailorable delivery of multiple genes, such as those encoding for BMP-2, VEGF, EGF-1, and TGF-$\beta$1, has been achieved through encapsulating genes into biodegradable polymeric microspheres with different degradation rates that were subsequently bound to biomaterials. Gene delivery is then dependent on a combination of polymeric delivery and DNA diffusion, and sequential delivery could be tailored via choice of polymer; for instance, poly(L-lactic-glycolic acid) is a suitable candidate owing to its degradation rate that may be tailored via manipulating its molecular weight and copolymer ratios. Additional strategies involving the encapsulation and chemical binding of viral and non-viral DNA have been attempted, however safety concerns with off-target delivery and inefficiencies with gene transfer inhibit their development.

In prior work, we introduced a new approach for achieving tailorable delivery through both CMP-mediated DNA polyplex release and a viral-like uptake. Specifically, CMP modification of polyplexes was previously demonstrated to stably integrate polyplexes into collagen scaffolds, the most common biomaterial, in a tailorable manner for periods of up to a month, and CMP immobilization also preserved polyplex activity in the presence of serum for 2 weeks. Transfection studies demonstrated release to be protease-mediated. Use of CMPs also facilitated polyplex interactions with collagen fragments even after the polyplexes were released from the scaffolds, and CMPs promoted polyplex uptake into cells through an endocytic uptake process that was previously linked to high efficiency gene expression. Furthermore, CMP/collagen delivery systems were observed to enable tailoring of the extent and length of transgene expression in murine ECM depot models, and the expression kinetics were directly dependent on CMP modification. The CMP/collagen delivery system promoted enhanced wound closure in in vitro wound models through mediating PDGF-BB expression. Notably, in order to promote healing in the wound model, collagens with mixtures of polyplexes containing different amounts of CMP were applied to expand the PDGF-BB expression time periods. Specifically, polyplexes with relatively fast and slow release kinetic (e.g., 10% GPP-PEI and 50% GPP-PEI, respectively) were used to facilitate both faster and more sustained expression.

In this study, the ease of varying CMP display on polyplexes, and in turn, the release kinetics and activity of CMP polyplexes modified with different amounts of CMPs, were utilized to manipulate the expression of multiple proteins within the same system. Mechanistic studies expressing reporter proteins GFP and GLuc demonstrated a high degree of tailorability and subsequent studies with genes encoding for PDGF-BB and KGF demonstrated a similar capacity to tune expression via CMP modification of functional proteins. Additionally, the capacity to further expand expression time periods via the establishment of highly stable collagen-based scaffolds through fibrin incorporation is discussed. The ability to encourage tailorable expression of multiple factors for prolonged periods via a method that also encourages improved gene transfer has widespread potential in regenerative medicine applications.

Materials and Methods

Materials

Type I bovine collagen was purchased from Advanced BioMatrix (San Diego, CA) and pCMV-PDGF-B and pCMV-KGF plasmids were purchased from Origene Technologies, Inc. (Rockville, MD). pDNA was amplified in NEB 5-α electrocompetent *E. coli* purchased from New England Biolabs and purified from bacterial culture using a Qiagen Megaprep Kit (Valencia, CA), following the manufacturer's protocols. The Mouse/Rat PDGF-BB and KGF Quantikine enzyme-linked immunosorbent assay (ELISA) kits were purchased from R&D Systems (Minneapolis, MN). Fmoc-protected amino acids were purchased from Anaspec (Fremont, CA). H-Rink amide CHEMMATRIX resin was purchased from PCAS Biomatrix (Quebec, Canada). O-Benzotriazole-N,N,N',N'-tetramethyl-uronium-hexafluoro-phosphate (HBTU) was purchased from Novabiochem (San Diego, CA). High performance liquid chromatography (HPLC)-grade N,N-dimethyl formamide (DMF), acetonitrile, trifluoroacetic acid (TFA), CELL-TRACKER Deep Red, and cell culture reagents, including Dulbecco's modified Eagle's medium (DMEM), Dulbecco's phosphate buffered saline (PBS), penicillin-streptomycin (P/S), and trypsin were purchased from Fisher Scientific (Fairlawn, NJ). Fetal bovine serum (FBS) was purchased from Corning (Manassas, MA). Collagenase I was purchased from Worthington Biochemical Corp (Lakewoord, NJ). Piperidine, 4-methylmorpholine, all cleavage cocktail components, branched PEI (25 kDa), calcium chloride, thrombin, and fibrinogen were purchased from Sigma-Aldrich (St. Louis, MO). SG-PEG-SG was purchased from NOF America (White Plains, NY).

Methods

Multi-Gene Modified Collagen/Fibrin Co-Gel Preparation

The CMP [GPP: (GPP)$_3$GPRGEKGERGPR(GPP)$_3$ (SEQ ID NO: 3)] used in prior studies was synthesized using Fmoc solid phase peptide synthesis and purified using reverse phase-HPLC. GPP was conjugated to PEI using Michael-type addition chemistry and the conjugate (GPP-PEI) was used to prepare GPP-modified polyplexes as previously described. Using a variation of well-established polyplex formation protocols, equivolumetric solutions of PEI and DNA in 20 mM HEPES buffer (pH 6.0) were mixed to produce a final solution with an amine to phosphate ratio (N:P) ratio of 10. To incorporate GPP, the GPP-PEI conjugate was preincubated at 50° C. for 30 minutes to prevent triple-helical hybridization of GPP, and a specified percent of PEI used to create the polyplex was replaced with the GPP-PEI.

To prepare the collagen/fibrin co-gels, lyophilized polyplexes were mixed with neutralized bovine collagen solution (8:1:1=NUTRAGEN: 10×PBS: 0.1M NaOH; final collagen concentration: 4 mg/mL) in a pre-chilled container and subsequently placed on ice. A pre-chilled thrombin/Ca$^{2+}$ solution (DMEM supplemented with thrombin and 0.2% 2N Ca$^{2+}$) and fibrinogen solution (in 20 mM HEPES buffered saline) were then added to the collagen/polyplex solution with thorough mixing in between each addition, resulting in a final solution of 2 mg/mL of collagen, 2-5 mg/mL fibrinogen, 0.2 U of thrombin per mg of fibrinogen, and 50 μg/mL of DNA. Mixtures were then immediately plated and incubated overnight at 37° C. to allow gelation.

Detection of GLuc and GFP Expression in Multigene Fibrin Co-Gels

DNA/collagen/fibrin co-gels were prepared as described above with 250 μL of DNA/collagen solution in 8 well plates (0.8 cm$^2$ surface area/well). Gels were incubated at 37° C. overnight to allow gelation, after which gels were washed three times with 200 μL each of PBS and complete medium (DMEM with 10% FBS and 1% P/S). Subsequently, an additional 200 μL of complete medium was added 1 h post cell-plating to allow rehydration. 50,000 NIH/3T3 cells were seeded per well and cells were cultured under standard conditions (37° C., 5% CO$^2$). The cells were allowed to adhere over a period of 6 h before treatment with tumor necrosis factor-alpha (TNF-α) (10 ng/mL), a well-known stimulator of MMP production. To account for the long half-life of secreted GLuc protein (almost 7 days) and the need to replenish culture medium to prevent cell death, kinetic GLuc expression also was analyzed in this study. Specifically, every 2 days, conditioned medium was collected from the samples and stored at −20° C., and an equal volume of fresh medium was subsequently replaced in the samples, after which the samples continued to be cultured under standard conditions. GLuc expression was quantified through detection of luminescence in 10 μL of the media collected from each sample using a BIOLUX Gaussia Luciferase Assay (NE BIOLAB; Ipswich, MA), according to the manufacturer's protocol. The resulting luminescence readings indicated the level of expression over the previous 2 days.

GFP is not secreted and has a half-life of about 26 h. Levels of GFP were therefore examined using fluorescence readings of the cell lysate; the majority of fluorescence in these samples was thus the result of GFP expressed over the preceding 2 days. Specifically, to quantify GFP expression, cells were recovered from gels incubated for 4, 8, 12, or 16 days through use of a collagenase (0.1 U/mL PBS)/dispase (0.8 U/mL PBS) digestion solution, accompanied with gentle pipetting to break the gel apart. After a 45-minute digestion at 37° C., cells were pelleted via centrifugation at 21,000 g for 5 minutes. The cell pellet was re-suspended in 200 μl of non-denaturing lysis buffer (1% w/v Triton X-100; 50 mM TrisCl, pH=7.4, 300 mM NaCl, 5 mM EDTA, and protease inhibitor) for 5 minutes on ice and the cell lysate solution fluorescence was immediately quantified using a Glomax Multimodal Plate reader. To compare expression, luminescence and fluorescence readings were normalized by their respective highest readings.

Detection of Functional Protein Expression

DNA/collagen/fibrin co-gels were prepared with 250 μL of DNA/collagen solution in 8 well plates (0.8 cm$^2$ surface area/well). Gels were incubated at 37° C. overnight to allow gelation, after which gels were washed three times with 200 μL each of PBS and complete medium (DMEM with 10% FBS and 1% P/S); 200 μL of complete medium was added 1 h post cell-plating to allow rehydration. 50,000 NIH/3T3 cells were seeded per well and cells were cultured under standard conditions (37° C., 5% CO$^2$). Every 4 days, 100 μL of cultured media was carefully collected from each sample, and the same volume of fresh media was replaced in the sample. Medium samples were stores at ~20° C. A sandwich ELISA was used to determine PDGF-BB and KGF concentrations in the conditioned media. PDGF-BB and KGF were both quantified using commercially available Quantikine ELISA kits in a 96-well plate format, according to the manufacturer's instructions. A seven-point standard curve was used to quantify the concentrations, spanning a range from 0 to 2000 ng/mL PDGF-BB or KGF. Each sample was read twice with a Glomax Multimodal Plate reader (Sigma), and the average of the two readings was used to calculate the concentration of PDGF-BB or KGF in the sample.

Results

Enhanced Stability of Collagen-Fibrin Co-Gels Extends CMP-mediated Expression

To achieve the prolonged DNA delivery vital for regenerative medicine applications like chronic wound repair, a scaffold stable for the required duration is required. To expand the periods of expression previously observed in collagen gels, CMP-mediated gene expression and cell behavior were studied in collagen/fibrin co-gels previously shown to have enhanced stability relative to collagen gels. Polyplex retention experiments revealed a profound enhancement in initial DNA retention in the collagen/fibrin co-gels compared to the collagen gels. When 20-100 μg of DNA-containing polyplexes were incorporated into gels comprised of 2 mg/mL of collagen and 5-10 mg/mL of fibrin, the initial DNA retention efficiency was approximately 100%, regardless of the level of CMP incorporation in the polyplex. On the other hand, the maximum DNA retention in co-gels containing 2 mg/mL of collagen and 2.5 mg/mL of fibrin was significantly reduced, at 86 μg/mL, relative to the compositions with high fibrin concentrations; however, even in these gels, initial DNA retention was still greatly enhanced compared to collagen gels (5.8- and 4-fold for 0% and 50% GPP-PEI modified polyplexes, respectively).

In subsequent studies, co-gels comprised of 2 mg/mL of collagen, 2.5 mg/mL of fibrin, and 50 μg of complexed DNA were prepared for analysis of gene expression. This composition was chosen based on preliminary cell behavioral studies, which showed impaired cellular invasion of matrices with higher fibrin concentrations (5 and 10 mg/mL). A 50 μg/mL DNA concentration was selected because the addition of larger amounts (e.g., 100 μg/mL) of DNA polyplexes had observable effects on gelation, resulting in decreased overall collagen retention in the scaffold.

Studies of the kinetics of Gluc expression were subsequently conducted to confirm the expected increase in gene expression in the co-gels, and to determine the effect of CMP modification (FIG. 15). Gluc was analyzed via detection of luminescence in conditioned medium that was replaced fully at each collection point; therefore, the reported luminescence values indicate freshly expressed luciferase subsequent to the previous collection time point (3 or 4 days prior). Incorporation of fibrin into the collagen gels was confirmed to expand the time period in which GLuc expression was detected. Specifically, increased expression was observed for an extended time period in both unmodified polyplex gels (4 days vs. 9 days post cell seeding) and 50% GPP-PEI modified polyplex gels (5 days vs. 17 days post cell seeding) when fibrin was incorporated into the gels. The overall expression levels also were approximately an order of magnitude greater compared to that observed in collagen-only gels. Additionally, CMP modification had a direct impact on polyplex activity within the co-gel, indicated by significant luciferase expression for up to 17 days in the 50% GPP-PEI polyplex sample, vs. 14 days for the 20% GPP-PEI polyplex sample and 10 days for the unmodified polyplex sample. Cumulative expression was also greater in both GPP-modified samples (approximately 19% and 30% greater in 20% and 50% GPP-PEI samples respectively, relative to the unmodified sample). Furthermore, 50% GPP modification promoted significantly more consistent expression over the 7 to 14 day time period post cell seeding, suggesting that sustained release was promoted by the GPP-PEI modification.

CMP Display on Polyplexes Enables Manipulation of Reporter Protein Expression

The ability to achieve controlled multigene delivery has tremendous benefits in the intricate process of wound repair. Through incorporation of polyplexes encoding GFP or GLuc and manipulations of CMP display, the ability to tailor expression within collagen/fibrin co-gels was examined. As shown in FIG. 16, the activity of both reporter proteins was normalized by the maximum luminescence or fluorescence detected for GLuc and GFP, respectively, to enable comparison of gene expression kinetics. The results of these studies demonstrated that in unmodified polyplex samples, both proteins achieved maximal expression at approximately day 6-8. By comparison, maximal expression was observed at day 14-16 for GLuc and day 10-12 for GFP in samples where both reporter plasmids were delivered in polyplexes with 50% GPP-PEI modification. Moreover, when the pGFP polyplex was unmodified but the pLuc polyplex had 50% GPP-PEI modification, maximum expression of GFP occurred earlier, at day 6-8, whereas maximum GLuc expression occurred at day 14-16. Furthermore, when unmodified pLuc polyplex and 50% GPP-PEI GFP polyplex were employed, maximum expression of Gluc and GFP were detected at day 6-8 and day 10-12, respectively. Other samples that were modified to various degrees demonstrated similar trends, with a direct correlation between the maximum expression times and the extent of CMP modification.

Functional Protein (GF) Expression Profiles can be Tailored Via CMP Display

Given the therapeutic value of multi-protein delivery, the capacity of the CMP/DNA/collagen system to tailor the expression of two GFs, PDGF-BB and KGF, was explored through incorporation of polyplexes encoding for the two GFs and modified with different amounts of GPP. As demonstrated in FIG. 17 and FIG. 18, GPP-modification caused significant alterations in expression profiles. Maximal expression levels for both proteins when expression was mediated by unmodified polyplex occurred during day 0-4, with KGF concentrations 2.9-fold high then PDGF-BB concentrations. By day 8, PDGF-BB and KGF expression had decreased by 23% and 34%, respectively, and by day 12, KGF expression has decreased a further 63% while levels of PDGF-BB levels were negligible. By comparison, when both the PDGF-BB- and KGF-encoding polyplexes were 50% GPP-PEI modified, expression levels of both proteins were significantly lower than in the unmodified sample (expression decreased by 88% and 31% for KGF and PDGF-BB, respectively). Maximum expression was not achieved until day 4-8, and protein expression overall remained relatively constant for the 12-day duration of the study. In samples in which pKGF polyplex was GPP-PEI modified and pPDGF-B polyplex was not, PDGF-BB expression remained almost identical to that observed in samples in which neither was modified; however, KGF expression was decreased by approximately 28% over day 0-4 relative to the unmodified sample. In samples in which only pPDGF-B was GPP-modified, the overall levels of expression for both proteins were reduced when compared to the results when neither was modified.

Discussion

Prolonged multi-GF gene expression has been demonstrated to have utility in wound care. The ability to tailor the expression of both the reporter proteins GFP and GLuc, and the GFs PDGF-BB and KGF, was demonstrated. Sustained delivery requires the application of a stable scaffold, and therefore the first part of this work explored the utility of incorporating fibrin into our CMP/DNA/collagen system based on studies demonstrating enhanced stability of collagen/fibrin co-gels. A composition comprised of 2.5 mg/mL of fibrin and 2 mg/mL of collagen with 50 μg/mL of DNA polyplexes was chosen based on the observation that higher fibrin concentrations greatly impeded cellular invasion and higher DNA concentrations affected gelation. The co-gel retained the capacity to incorporate approximately 2.5-fold more DNA then collagen-gels alone, and the co-gels also exhibited longer expression periods (e.g., less than a week vs. 2 weeks).

The length of time polyplex activity was observed in the co-gel was similar to that achieved by another system in which NIH/3T3 cells were co-encapsulated into fibrin gels with PEI polyplexes encoding for reporter protein (secreted alkaline phosphatase). In these studies, the same concentration of DNA was used (50 μg/mL) and a similar protein content was employed. However, while the length of time gene expression occurred in this system was similar to that which occurred in our co-gels in the case of the unmodified polyplex, GPP-PEI modification altered gene expression kinetics significantly by greatly extending the duration over which increases in expression were observed to 17 days. Significantly, at this composition, both the initial DNA retention efficiency and release/retention rates were not GPP dependent, and transfection studies further suggested that GPP-modification may aid in achieving sustained release in the presence of cellular components and proteolytic degradation. The results suggest that the new scaffold may aid in the prevention of off-target responses while still providing a stable scaffold to mediate release.

The ability to simultaneously tailor release of both GFP/GLuc and KGF/PDGF-BB was also demonstrated. Studies with the reporter proteins provided solid evidence of the ability to tailor the expression of two proteins within the same system using GPP-modification, yet the GF tailoring results were harder to predict. In general, the levels of expression were highest at earlier time periods when unmodified polyplexes were employed, and the levels of expression were quickly reduced at longer time points. In the GF expression studies, our results showed that KGF concentrations were dependent on PDGF-BB concentrations. For example, KGF expression was delayed and reduced regardless of GPP-modification when co-delivered with 50% GPP-PEI pPDGF-BB polyplex. This finding is likely because PDGF-BB triggers NIH/3T3 proliferation and migration, which are both behaviors known to promote increased polyplex uptake, and in turn, transfection. On the other hand, KGF is not recognized to trigger any behaviors in NIH/3T3 cells. Co-culture experiments with cells responsive to KGF, such as keratinocytes, may provide more insight on the potential of CMP/DNA/collagen systems to tailor both multi-gene expression and behaviors in various cell types relevant to wound repair applications including keratinocytes and macrophages.

Conclusions/Future Work

CMP-mediated delivery in collagen/fibrin co-gels enabled the tailoring of both reporter proteins and GFs. The incorporation of fibrin greatly reduced non-cell mediated release of polyplexes independently of CMP modification; however, CMP modification was observed to preserve polyplex activity. These findings suggest that the fibrin/collagen composition could be used to prevent vector escape, while still providing a stable scaffold to facilitate CMP-mediated release. Meanwhile, high levels of transfection were observed in the co-gels, yet expression was delayed relative to that observed in collagen gels, likely due in part to slower matrix invasion. Overall, this approach shows great promise and a method for promoting prolonged expression and cellular invasion would be compelling in wound care.

All documents, books, manuals, papers, patents, published patent applications, guides, abstracts, and/or other references cited herein are incorporated by reference in their entirety. Other embodiments of the invention will be apparent to those skilled in the art from consideration of the specification and practice of the invention disclosed herein. It is intended that the specification and examples be considered as exemplary only, with the true scope and spirit of the invention being indicated by the following claims.

What is claimed:

1. A method comprising:
   (a) administering an effective amount of a composition to cells in a subject, wherein the composition comprises
      (i) at least one collagen-mimetic peptide (CMP),
      (ii) a polyplex, wherein the polyplex comprises at least one polymer and at least one polynucleotide encoding a protein, and the at least one CMP is bound to the polyplex, wherein the protein is a healing factor selected from the group consisting of a growth factor, an anti-inflammatory cytokine, and a combination thereof, and
      (iii) collagen or fragments thereof, wherein the at least one CMP is bound to the collagen or fragments thereof;
   (b) expressing the protein by the cells in the subject; and
   (c) enhancing migration, proliferation and/or differentiation of the cells in the subject.

2. The method of claim 1, wherein the at least one polynucleotide comprises DNA.

3. The method of claim 1, wherein the at least one polynucleotide comprises RNA.

4. The method of claim 1, wherein the at least one CMP is bound to the polyplex via a covalent linkage.

5. The method of claim 1, wherein the at least one CMP is bound to the polyplex via a noncovalent linkage.

6. The method of claim 1, wherein the at least one polynucleotide further encodes at least one silencing RNA capable of suppressing expression of the protein, the method further comprising suppressing the expression of the protein by the cells.

7. The method of claim 1, wherein the cells are at a wound in the subject.

8. The method of claim 1, wherein step (c) comprises enhancing proliferation of the cells.

9. The method of claim 1, further comprising enhancing production of extracellular matrix by the cells.

10. The method of claim 1, wherein step (c) comprises enhancing migration of the cells.

11. The method of claim 7, wherein the wound is a chronic wound.

12. The method of claim 1, wherein the protein is a growth factor.

13. The method of claim 1, wherein the protein is an anti-inflammatory cytokine.

14. The method of claim 1, wherein the composition further comprises an extracellular matrix (ECM) component selected from the group consisting of fibrin, fibronectin, laminins, ECM proteoglycans, ECM glycosaminoglycans and combinations thereof.

15. A method comprising:
   (a) administering an effective amount of a composition to cells in a subject, wherein the composition comprises
      (i) at least one collagen-mimetic peptide (CMP),
      (ii) a polyplex, wherein the polyplex comprises at least one polymer and at least one polynucleotide encoding a protein, and the at least one CMP is bound to the polyplex,
      (iii) collagen or fragments thereof, wherein the at least one CMP is bound to the collagen or fragments thereof, and
      (iv) a matrix metalloproteinase (MMP); and
   (b) expressing the protein by the cells in the subject.

16. The method of claim 1, wherein the at least one CMP is (GPP)3GPRGEKGERGPR(GPP)3GPCCG (SEQ ID NO: 3) or (GPO)4GEKGER(GPO)4GGCG (SEQ ID NO: 4).

17. The method of claim 1, wherein step (c) comprises enhancing differentiation of the cells in the subject.

* * * * *

SEQUENCE LISTING

<160> NUMBER OF SEQ ID NOS: 6

<210> SEQ ID NO 1
<211> LENGTH: 23
<212> TYPE: PRT
<213> ORGANISM: Artificial Sequence
<220> FEATURE:
<223> OTHER INFORMATION: Synthetic
<220> FEATURE:
<221> NAME/KEY: REPEAT
<222> LOCATION: (1)..(3)
<220> FEATURE:
<221> NAME/KEY: REPEAT
<222> LOCATION: (16)..(18)

```
<400> SEQUENCE: 1

Gly Pro Pro Gly Pro Arg Gly Glu Lys Gly Glu Arg Gly Pro Arg Gly
1               5                   10                  15

Pro Pro Gly Pro Cys Cys Gly
            20

<210> SEQ ID NO 2
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: REPEAT
<222> LOCATION: (1)..(3)
<220> FEATURE:
<221> NAME/KEY: MISC_FEATURE
<222> LOCATION: (3)..(3)
<223> OTHER INFORMATION: Xaa is hydroxyproline
<220> FEATURE:
<221> NAME/KEY: REPEAT
<222> LOCATION: (10)..(12)
<220> FEATURE:
<221> NAME/KEY: MISC_FEATURE
<222> LOCATION: (12)..(12)
<223> OTHER INFORMATION: Xaa is hydroxyproline

<400> SEQUENCE: 2

Gly Pro Xaa Gly Glu Lys Gly Glu Arg Gly Pro Xaa Gly Gly Cys Gly
1               5                   10                  15

<210> SEQ ID NO 3
<211> LENGTH: 35
<212> TYPE: PRT
<213> ORGANISM: Artificial Sequence
<220> FEATURE:
<223> OTHER INFORMATION: Synthetic

<400> SEQUENCE: 3

Gly Pro Pro Gly Pro Pro Gly Pro Pro Gly Pro Arg Gly Glu Lys Gly
1               5                   10                  15

Glu Arg Gly Pro Arg Gly Pro Pro Gly Pro Pro Gly Pro Pro Gly Pro
            20                  25                  30

Cys Cys Gly
        35

<210> SEQ ID NO 4
<211> LENGTH: 34
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: X is hydroxyproline.
<220> FEATURE:
<221> NAME/KEY: MISC_FEATURE
<222> LOCATION: (6)..(6)
<223> OTHER INFORMATION: X is hydroxyproline
<220> FEATURE:
<221> NAME/KEY: MISC_FEATURE
<222> LOCATION: (9)..(9)
<223> OTHER INFORMATION: X is hydroxyproline
<220> FEATURE:
<221> NAME/KEY: MISC_FEATURE
<222> LOCATION: (12)..(12)
<223> OTHER INFORMATION: X is hydroxyproline
<220> FEATURE:
```

```
<221> NAME/KEY: MISC_FEATURE
<222> LOCATION: (21)..(21)
<223> OTHER INFORMATION: X is hydroxyproline
<220> FEATURE:
<221> NAME/KEY: MISC_FEATURE
<222> LOCATION: (24)..(24)
<223> OTHER INFORMATION: X is hydroxyproline
<220> FEATURE:
<221> NAME/KEY: MISC_FEATURE
<222> LOCATION: (27)..(27)
<223> OTHER INFORMATION: X is hydroxyproline
<220> FEATURE:
<221> NAME/KEY: MISC_FEATURE
<222> LOCATION: (30)..(30)
<223> OTHER INFORMATION: X is hydroxyproline

<400> SEQUENCE: 4

Gly Pro Xaa Gly Pro Xaa Gly Pro Xaa Gly Pro Xaa Gly Glu Lys Gly
1               5                   10                  15

Glu Arg Gly Pro Xaa Gly Pro Xaa Gly Pro Xaa Gly Pro Xaa Gly Gly
            20                  25                  30

Cys Gly

<210> SEQ ID NO 5
<211> LENGTH: 6
<212> TYPE: PRT
<213> ORGANISM: Artificial Sequence
<220> FEATURE:
<223> OTHER INFORMATION: Synthetic

<400> SEQUENCE: 5

Gly Glu Lys Gly Glu Arg
1               5

<210> SEQ ID NO 6
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: X is hydroxyproline

<400> SEQUENCE: 6

Gly Phe Xaa Gly Glu Arg
1               5
```